(12) United States Patent
Koo et al.

(10) Patent No.: US 10,862,044 B2
(45) Date of Patent: Dec. 8, 2020

(54) ORGANIC COMPOUND AND LIGHT EMITTING DIODE AND ORGANIC LIGHT EMITTING DIODE DISPLAY DEVICE USING THE SAME

(71) Applicant: LG DISPLAY CO., LTD., Seoul (KR)

(72) Inventors: Ki-Dong Koo, Daejeon (KR); Jung-Keun Kim, Seoul (KR); Do-Han Kim, Goyang-si (KR); Jeong-Dae Seo, Incheon (KR); Seon-Keun Yoo, Gunpo-si (KR); Seung-Hee Yoon, Seoul (KR); Ji-Cheol Shin, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 488 days.

(21) Appl. No.: 15/606,679

(22) Filed: May 26, 2017

(65) Prior Publication Data

US 2017/0346012 A1   Nov. 30, 2017

(30) Foreign Application Priority Data

May 27, 2016   (KR) .................. 10-2016-0065806

(51) Int. Cl.
| | | |
|---|---|---|
| *H01L 51/50* | (2006.01) | |
| *H01L 51/54* | (2006.01) | |
| *H01L 51/00* | (2006.01) | |
| *C07C 211/61* | (2006.01) | |
| *C07D 495/10* | (2006.01) | |
| *C07D 491/107* | (2006.01) | |

(Continued)

(52) U.S. Cl.
CPC ........ *H01L 51/0061* (2013.01); *C07C 211/61* (2013.01); *C07D 209/96* (2013.01); *C07D 307/94* (2013.01); *C07D 333/78* (2013.01); *C07D 405/14* (2013.01); *C07D 471/10* (2013.01); *C07D 491/107* (2013.01); *C07D 491/20* (2013.01); *C07D 491/22* (2013.01); *C07D 495/10* (2013.01); *C07D 521/00* (2013.01); *C07F 7/0812* (2013.01); *H01L 51/0072* (2013.01); *H01L 51/0073* (2013.01); *H01L 51/0074* (2013.01); *H01L 51/0094* (2013.01); *H01L 51/5012* (2013.01); *H01L 51/5056* (2013.01); *H01L 51/5088* (2013.01); *H01L 51/5096* (2013.01); *C07C 2603/94* (2017.05); *H01L 27/3244* (2013.01); *H01L 51/506* (2013.01); *H01L 51/5064* (2013.01)

(58) Field of Classification Search
CPC . C07C 211/61; C07C 2603/94; C07D 209/96; C07D 307/94; C07D 333/78; C07D 405/14; C07D 471/10; C07D 491/107; C07D 491/20; C07D 491/22; C07D 495/10; C07D 521/00; C07F 7/0812; H01L 27/3244; H01L 51/0061; H01L 51/0072; H01L 51/0073; H01L 51/0074; H01L 51/0094; H01L 51/5012; H01L 51/5056; H01L 51/5088; H01L 51/5096; H01L 51/506; H01L 51/5064

See application file for complete search history.

(56) References Cited

U.S. PATENT DOCUMENTS 5,998,805 A  * 12/1999  Shi ..................... H01L 51/5092
                                              257/103
2002/0121860 A1 * 9/2002  Seo .................... H01L 51/5012
                                              313/506

(Continued)

FOREIGN PATENT DOCUMENTS

| CN | 104024373 A | 9/2014 |
|---|---|---|
| CN | 105321984 A | 2/2016 |

(Continued)

OTHER PUBLICATIONS

Kageyama et al., Machine translation of JP-2007119454-A (2007) pp. 1-67. (Year: 2007).*

(Continued)

*Primary Examiner* — Dylan C Kershner
(74) *Attorney, Agent, or Firm* — Birch, Stewart, Kolasch & Birch, LLP

(57) ABSTRACT

The present disclosure relates to an organic compound, a light emitting diode and an organic light emitting diode display device using the same. The organic compound is represented by a following chemical formula 1.

Chemical Formula 1

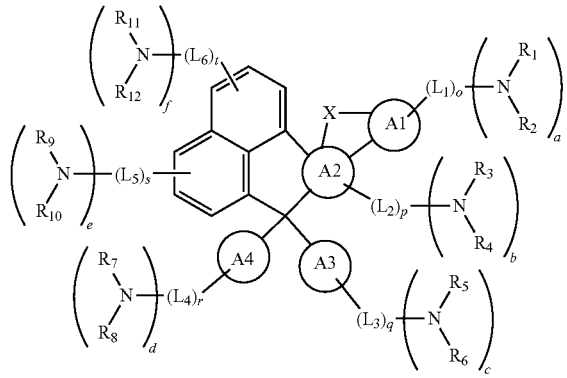

This organic compound has the advantages in the thermal stability, the emission property, the color purity, the hole transport property and the hole movement property, and thus the lifetime, the emission efficiency and the emission property of the LED using the same are improved.

13 Claims, 3 Drawing Sheets

(51) Int. Cl.
*C07D 471/10* (2006.01)
*C07D 333/78* (2006.01)
*C07D 307/94* (2006.01)
*C07D 491/20* (2006.01)
*C07F 7/08* (2006.01)
*C07D 209/96* (2006.01)
*C07D 405/14* (2006.01)
*C07D 491/22* (2006.01)
*C07D 521/00* (2006.01)
*H01L 27/32* (2006.01)

(56) References Cited

U.S. PATENT DOCUMENTS

2009/0261717 A1* 10/2009 Buesing ................ C07C 13/62
313/504

2019/0348616 A1* 11/2019 Parham ................ C07D 409/14

FOREIGN PATENT DOCUMENTS

| EP | 2799515 A1 | | 11/2014 |
|---|---|---|---|
| JP | 2007-123863 A | | 5/2007 |
| JP | 2007119454 A | * | 5/2007 |
| KR | 10-2007-0037340 A | | 4/2007 |
| KR | 10-2008-0109000 A | | 12/2008 |
| WO | WO 2016/013184 A1 | | 1/2016 |

OTHER PUBLICATIONS

Kimura et al., "Spirocycle-Incorporated Triphenylamine Derivatives as an Advanced Organic Electroluminescent Material" Chemistry Letters (2000) vol. 29, pp. 192-193. (Year: 2000).*

* cited by examiner

ORGANIC COMPOUND AND LIGHT EMITTING DIODE AND ORGANIC LIGHT EMITTING DIODE DISPLAY DEVICE USING THE SAME

CROSS-REFERENCE TO RELATED APPLICATIONS

This application claims the benefit under 35 U.S.C. § 119(a) of Korean Patent Application No. 10-2016-0065806, filed on May 27, 2016, in the Korean Intellectual Property Office, which is incorporated herein by reference in its entirety into the present application.

BACKGROUND

1. Technical Field

The present disclosure relates to an organic compound, and more particularly, to an organic compound where a thermal stability and an emission property are improved and a light emitting diode and an organic light emitting diode display device using the organic compound where an emission efficiency and a lifetime are improved.

2. Discussion of the Related Art

As a display device is enlarged, a request for a flat panel display of a small space possession increases. Among various flat panel displays, an organic light emitting diode (OLED) display device, which may be referred to as an organic electroluminescent display (OELD) device, including a light emitting diode has been the subject of recent research.

A backlight unit required for a liquid crystal display (LCD) device is not necessary for the OLED display device. As a result, the OLED display device has an emissive type where an emitting pixel of a light emitting diode (LED) emits a light. Since a fabrication process of the OLED display device is simplified, a light weight and a thin profile are obtained. In addition, a low driving voltage (lower than about 10V), a low power consumption and an excellent color purity are obtained. The OLED display device has advantages in a viewing angle and a contrast ratio as compared with the LCD device. Since elements of the OLED display device are capable of be formed on a flexible transparent substrate, the OLED display device has been researched as a next generation display device after the LCD device.

The LED of the OLED display device is an element where a light is emitted due to extinction of an exciton in an emitting layer. When an electron and a hole are injected into the emitting layer of an organic material between an electron injecting electrode (cathode) and a hole injecting electrode (anode), a pair of the electron and the hole form the exciton and the light is emitted from the emitting layer while the exciton transitions to a ground state.

The emitting layer of the LED may have a single layered structure or a multiple layered structure for improving an emission efficiency and a lifetime. For example, the emitting layer of the LED may have a multiple layered structure including a hole injecting layer (HIL), a hole transporting layer (HTL), an emitting material layer (EML), an electron transporting layer (ETL) and an electron injecting layer (EIL).

The OLED display device may be fabricated through a following process.

(1) An anode is formed on a transparent substrate by depositing a transparent conductive material such as indium tin oxide (ITO).

(2) A HIL is formed on the anode. The HIL includes an organic material such as Dipyrazino[2,3-f:2',3'-h]quinoxaline-2,3,6,7,10,11-hexacarbonitrile (HATCN) and has a thickness of about 10 nm to about 60 nm.

(3) A HTL is formed on the HIL. The HTL include an organic material such as 4,4'-bis[N-(1-naphtyl)-N-phenylamino]-biphenyl (NPB) and has a thickness of about 20 nm to about 60 nm. For confining a triplet exciton in an EML of a phosphorous element, an exciton blocking layer such as an electron blocking layer (EBL) may be formed between the HTL and the EML.

(4) An EML, which is referred to as an organic emitting layer, is formed on the HTL. The EML includes a host and a dopant. For a blue fluorescent element, the host may include 9,10-Bis(1-naphtyl)anthracene (α-ADN) and the dopant may include 4,4'-bis[2-(4-(N,N-diphenylamino)phenyl)vinyl]biphenyl(DPAVBi) or diphenyl-[4-(2-[1,1;4,1]terphenyl-4-yl-vinyl)-phenyl]-amine (BD-1). The host may be doped with the dopant by about 1 weight percent (wt %) to about 50 wt %, for example, about 1 wt % to about 10 wt %. The EML has a thickness of about 20 nm to about 60 nm.

(5) An ETL and an EIL are formed on the EML. For example, the ETL may include tris(8-hydroxy-quinolate) aluminum (Alq3) and the EIL may include LiF. For confining the triplet exciton in the EML of a phosphorous element, an exciton blocking layer such as a hole blocking layer (HBL) may be formed between the EML and the ETL.

(6) A cathode is formed on the EIL.

A polymer or a monomer may be used as an organic material for the EML of the LED. For example, Korean Patent No. 10-0525408 and Korean Patent No. 10-1217979 suggest that an amine derivative where an aromatic group or an aliphatic amine group of a pyrene ring is substituted may be used as a dopant for a blue EML.

In the LED, the hole and the electron injected from the anode and the cathode, respectively, form the exciton to emit the light. When a single material is used for the EML, the color purity, the emission efficiency and the lifetime may be deteriorated. To improve the color purity, the emission efficiency and the lifetime, the EML may include the host and the dopant. In the host-dopant system, the host generates the exciton and transmits an energy to the dopant so that the dopant can emit a light of a high emission efficiency. Accordingly, an emission wavelength is determined according to an energy band of the dopant, and a structure of the dopant influence the emission efficiency, the electrical property and the lifetime of the LED.

Specifically, although a material having a relatively wide energy band is required for the blue emission, the material having a relatively wide energy band does not satisfy the lifetime, the electrical property and the emission efficiency. For example, when BD-1 is used as a blue dopant, the lifetime and the emission efficiency of the LED are deteriorated.

SUMMARY

Embodiments relate to an organic compound represented by a following chemical formula 1.

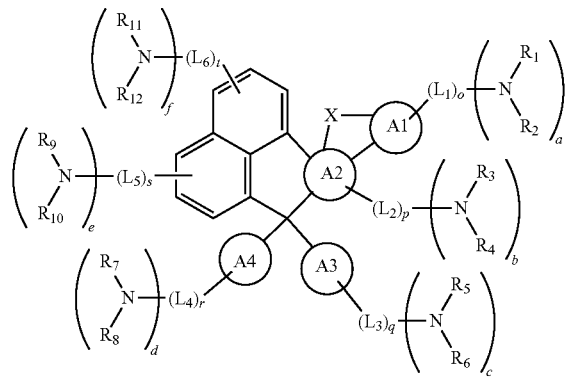

In the chemical formula 1, each of A1, A2, A3 and A4 is independently one of a non-substituted or substituted aromatic ring of C5 to C30 and a non-substituted or substituted hetero aromatic ring of C4 to C30. Each of A3 and A4 independently forms an aromatic ring or a hetero aromatic ring. Alternatively, an atom of the aromatic ring or the hetero aromatic ring of A3 and an atom of the aromatic ring or the hetero aromatic ring of A4 are combined with each other to form a fused ring. Each of L1 to L6 is independently selected from the group including a non-substituted or substituted alkylene group of C1 to C20, a non-substituted or substituted alkenylene group of C2 to C20, a non-substituted or substituted alkynylene group of C2 to C20, a non-substituted or substituted cycloalkylene group of C3 to C30, a non-substituted or substituted hetero cycloalkylene group of C3 to C30, a non-substituted or substituted arylene group of C5 to C30, a non-substituted or substituted hetero arylene group of C4 to C30, a non-substituted or substituted arylalkylene group of C6 to C30, a non-substituted or substituted hetero arylalkylene group of C6 to C30, a non-substituted or substituted aryloxylene group of C6 to C30, and a non-substituted or substituted hetero aryloxylene group of C6 to C30. Each of o, p, q, r, s and t is independently 0 or 1. Each of R1 to R12 is independently selected from the group including a hydrogen atom, a non-substituted or substituted alkyl group of C1 to C20, a non-substituted or substituted alkenyl group of C2 to C20, a non-substituted or substituted alkynyl group of C2 to C20, a non-substituted or substituted alkoxy group of C1 to C20, a non-substituted or substituted cycloalkyl group of C3 to C30, a non-substituted or substituted hetero cycloalkyl group of C3 to C30, a non-substituted or substituted of aryl group of C5 to C30, a non-substituted or substituted hetero aryl group of C4 to C30, a non-substituted or substituted arylalkyl group of C6 to C30, a non-substituted or substituted hetero arylalkyl group of C6 to C30, a non-substituted or substituted aryloxyl group of C6 to C30, a non-substituted or substituted hetero aryloxyl group of C6 to C30, alkylamine group of C1 to C20, a non-substituted or substituted aryl amine group of C5 to C30, and a non-substituted or substituted hetero aryl amine group of C5 to C30. x is selected from the group including S, O, NR13, CR14R15 and SiR16R17. Each of R13 to R17 is independently selected from the group including a hydrogen atom, a non-substituted or substituted alkyl group of C1 to C20, a non-substituted or substituted alkenyl group of C2 to C20, a non-substituted or substituted alkynyl group of C2 to C20, a non-substituted or substituted alkoxy group of C1 to C20, a non-substituted or substituted cycloalkyl group of C3 to C30, a non-substituted or substituted hetero cycloalkyl group of C3 to C30, a non-substituted or substituted of aryl group of C5 to C30, a non-substituted or substituted hetero aryl group of C4 to C30, a non-substituted or substituted arylalkyl group of C6 to C30, a non-substituted or substituted hetero arylalkyl group of C6 to C30, a non-substituted or substituted aryloxyl group of C6 to C30, a non-substituted or substituted hetero aryloxyl group of C6 to C30, alkylamine group of C1 to C20, a non-substituted or substituted aryl amine group of C5 to C30, and a non-substituted or substituted hetero aryl amine group of C5 to C30. Each of a, b, c, d, e and f is independently 0 or 1, and at least one of a, b, c, d, e and f is 1.

One or more embodiments relate to a light emitting diode includes: a first electrode; a second electrode facing into the first electrode; and at least one organic material layer between the first and second electrodes, wherein the at least one organic material layer includes an organic compound represented by a following chemical formula 1.

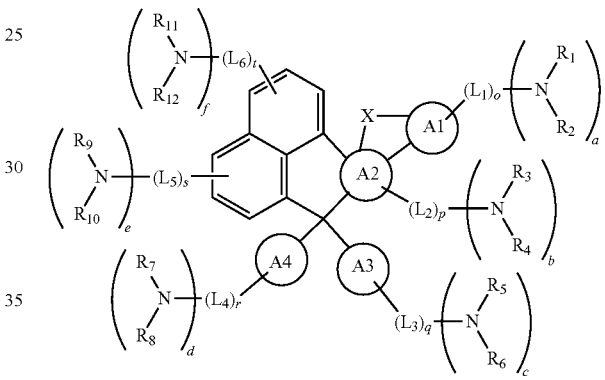

In the chemical formula 1, each of A1, A2, A3 and A4 is independently one of a non-substituted or substituted aromatic ring of C5 to C30 and a non-substituted or substituted hetero aromatic ring of C4 to C30. Each of A3 and A4 independently forms an aromatic ring or a hetero aromatic ring. Alternatively, an atom of the aromatic ring or the hetero aromatic ring of A3 and an atom of the aromatic ring or the hetero aromatic ring of A4 are combined with each other to form a fused ring. Each of L1 to L6 is independently selected from the group including a non-substituted or substituted alkylene group of C1 to C20, a non-substituted or substituted alkenylene group of C2 to C20, a non-substituted or substituted alkynylene group of C2 to C20, a non-substituted or substituted cycloalkylene group of C3 to C30, a non-substituted or substituted hetero cycloalkylene group of C3 to C30, a non-substituted or substituted arylene group of C5 to C30, a non-substituted or substituted hetero arylene group of C4 to C30, a non-substituted or substituted arylalkylene group of C6 to C30, a non-substituted or substituted hetero arylalkylene group of C6 to C30, a non-substituted or substituted aryloxylene group of C6 to C30, and a non-substituted or substituted hetero aryloxylene group of C6 to C30. Each of o, p, q, r, s and t is independently 0 or 1. Each of R1 to R12 is independently selected from the group including a hydrogen atom, a non-substituted or substituted alkyl group of C1 to C20, a non-substituted or substituted alkenyl group of C2 to C20, a non-substituted or substituted alkynyl group of C2 to C20, a non-substituted or substituted alkoxy group of C1 to C20, a non-substituted or substituted cycloalkyl group of C3 to C30, a non-substituted or substituted hetero cycloalkyl group of C3 to C30, a non-substituted or substituted of aryl group of C5 to C30, a non-substituted or substituted hetero aryl group of C4 to C30, a non-substituted or substituted arylalkyl group of C6 to C30, a non-substituted or substituted hetero arylalkyl group of C6 to C30, a non-substituted or substituted aryloxyl group of C6 to C30, a non-substituted or substituted hetero aryloxyl group of C6 to C30, alkylamine group of C1 to C20, a non-substituted or substituted aryl amine group of C5 to C30, and a non-substituted or substituted hetero aryl amine group of C5 to C30. And x is selected from the group including S, O, NR13, CR14R15 and SiR16R17. Each of R13 to R17 is independently selected from the group including a hydrogen atom, a non-substituted or substituted alkyl group of C1 to C20, a non-substituted or substituted alkenyl group of C2 to C20, a non-substituted or substituted alkynyl group of C2 to C20, a non-substituted or substituted alkoxy group of C1 to C20, a non-substituted or substituted cycloalkyl group of C3 to C30, a non-substituted or substituted hetero cycloalkyl group of C3 to C30, a non-substituted or substituted of aryl group of C5 to C30, a non-substituted or substituted hetero aryl group of C4 to C30, a non-substituted or substituted arylalkyl group of C6 to C30, a non-substituted or substituted hetero arylalkyl group of C6 to C30, a non-substituted or substituted aryloxyl group of C6 to C30, a non-substituted or substituted hetero aryloxyl group of C6 to C30, alkylamine group of C1 to C20, a non-substituted or substituted aryl amine group of C5 to C30, and a non-substituted or substituted hetero aryl amine group of C5 to C30. Each of a, b, c, d, e and f is independently 0 or 1, and at least one of a, b, c, d, e and f is 1.

One or more embodiments relate to an organic light emitting diode display device including: a first substrate; a driving thin film transistor on the first substrate; a light emitting diode connected to the driving thin film transistor, wherein the light emitting diode comprises: a first electrode; a second electrode facing into the first electrode; and at least one organic material layer between the first and second electrodes, wherein the at least one organic material layer includes an organic compound represented by a following chemical formula 1; and a second substrate covering the light emitting diode and attached to the first substrate.

Chemical Formula 1

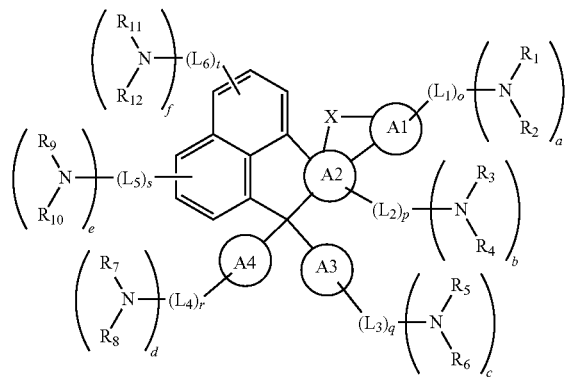

In the chemical formula 1, each of A1, A2, A3 and A4 is independently one of a non-substituted or substituted aromatic ring of C5 to C30 and a non-substituted or substituted hetero aromatic ring of C4 to C30. Each of A3 and A4 independently forms an aromatic ring or a hetero aromatic ring. Alternatively, an atom of the aromatic ring or the hetero aromatic ring of A3 and an atom of the aromatic ring or the hetero aromatic ring of A4 are combined with each other to form a fused ring. Each of L1 to L6 is independently selected from the group including a non-substituted or substituted alkylene group of C1 to C20, a non-substituted or substituted alkenylene group of C2 to C20, a non-substituted or substituted alkynylene group of C2 to C20, a non-substituted or substituted cycloalkylene group of C3 to C30, a non-substituted or substituted hetero cycloalkylene group of C3 to C30, a non-substituted or substituted arylene group of C5 to C30, a non-substituted or substituted hetero arylene group of C4 to C30, a non-substituted or substituted arylalkylene group of C6 to C30, a non-substituted or substituted hetero arylalkylene group of C6 to C30, a non-substituted or substituted aryloxylene group of C6 to C30, and a non-substituted or substituted hetero aryloxylene group of C6 to C30. Each of o, p, q, r, s and t is independently 0 or 1. Each of R1 to R12 is independently selected from the group including a hydrogen atom, a non-substituted or substituted alkyl group of C1 to C20, a non-substituted or substituted alkenyl group of C2 to C20, a non-substituted or substituted alkynyl group of C2 to C20, a non-substituted or substituted alkoxy group of C1 to C20, a non-substituted or substituted cycloalkyl group of C3 to C30, a non-substituted or substituted hetero cycloalkyl group of C3 to C30, a non-substituted or substituted of aryl group of C5 to C30, a non-substituted or substituted hetero aryl group of C4 to C30, a non-substituted or substituted arylalkyl group of C6 to C30, a non-substituted or substituted hetero arylalkyl group of C6 to C30, a non-substituted or substituted aryloxyl group of C6 to C30, a non-substituted or substituted hetero aryloxyl group of C6 to C30, alkylamine group of C1 to C20, a non-substituted or substituted aryl amine group of C5 to C30, and a non-substituted or substituted hetero aryl amine group of C5 to C30. x is selected from the group including S, O, NR13, CR14R15 and SiR16R17. Each of R13 to R17 is independently selected from the group including a hydrogen atom, a non-substituted or substituted alkyl group of C1 to C20, a non-substituted or substituted alkenyl group of C2 to C20, a non-substituted or substituted alkynyl group of C2 to C20, a non-substituted or substituted alkoxy group of C1 to C20, a non-substituted or substituted cycloalkyl group of C3 to C30, a non-substituted or substituted hetero cycloalkyl group of C3 to C30, a non-substituted or substituted of aryl group of C5 to C30, a non-substituted or substituted hetero aryl group of C4 to C30, a non-substituted or substituted arylalkyl group of C6 to C30, a non-substituted or substituted hetero arylalkyl group of C6 to C30, a non-substituted or substituted aryloxyl group of C6 to C30, a non-substituted or substituted hetero aryloxyl group of C6 to C30, alkylamine group of C1 to C20, a non-substituted or substituted aryl amine group of C5 to C30, and a non-substituted or substituted hetero aryl amine group of C5 to C30. Each of a, b, c, d, e and f is independently 0 or 1, and at least one of a, b, c, d, e and f is 1.

Advantages and features of the disclosure will be set forth in part in the description, which follows and in part will become apparent to those having ordinary skill in the art upon examination of the following or may be learned from practice of the disclosure. Other advantages and features of the embodiments herein may be realized and attained by the structure particularly pointed out in the written description and claims hereof as well as the appended drawings.

It is to be understood that both the foregoing general description and the following detailed description are explanatory, and are intended to provide further explanation of the embodiments as claimed.

BRIEF DESCRIPTION OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Figure 1:
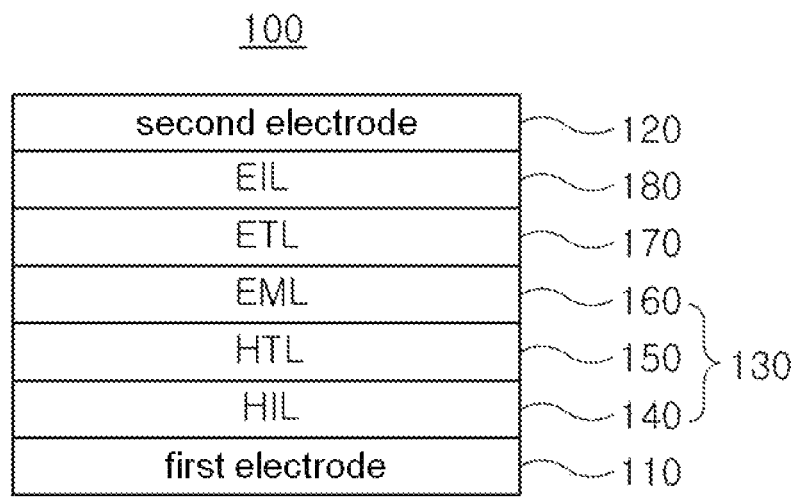
FIG. 1 is a cross-sectional view showing a light emitting diode according to a first embodiment of the present disclosure.

Reference will now be made in detail to embodiments of the present disclosure, examples of which are illustrated in the accompanying drawings. In the following description, when a detailed description of well-known functions or configurations related to this document is determined to unnecessarily cloud a gist of an embodiment of the disclosure, the detailed description thereof will be omitted. The progression of processing steps and/or operations described is an example; however, the sequence of steps and/or operations is not limited to that set forth herein and may be changed as is known in the art, with the exception of steps and/or operations necessarily occurring in a certain order. Like reference numerals designate like elements throughout. Names of the respective elements used in the following explanations are selected only for convenience of writing the specification and may be thus different from those used in actual products.

In an organic light emitting diode (OLED) display device according to an embodiment of the present disclosure, an emission efficiency and a lifetime are improved by applying an organic compound having an excellent thermal stability and an excellent material stability to an organic material layer of a light emitting diode (LED).

In the organic compound according to an embodiment of the present disclosure, an aromatic ring capable of having a spiro structure is selectively connected to an aromatic core having a fused structure, and an amine group is directly or indirectly connected to the fused aromatic core and/or the aromatic ring.

In the LED according to an embodiment of the present disclosure, the organic compound is applied to at least one organic layer between facing two electrodes.

In the OLED display device according to an embodiment of the present disclosure, the organic compound is applied to at least one organic layer between facing two electrodes of the LED.

[Organic Compound]

In an organic compound according to an embodiment of the present disclosure, an aromatic core includes an aromatic ring or a hetero aromatic ring of a fused structure, another aromatic ring is connected to the aromatic core through a spiro structure or a chain structure, and an amine group is directly or indirectly connected to the aromatic core of a fused structure and/or another aromatic ring. The organic compound has an excellent thermal stability, an excellent emission property and an excellent hole transport property.

For example, the organic compound may be represented by a following chemical formula 1.

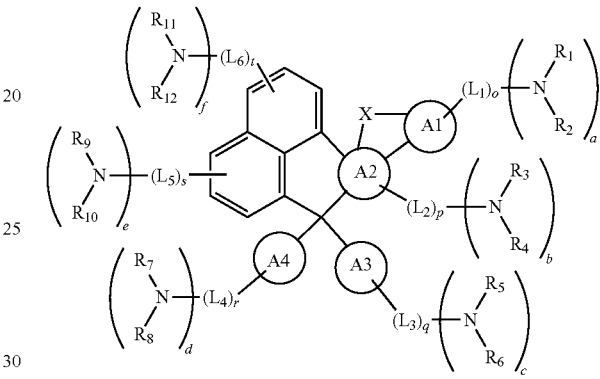

Chemial Formula 1

In the chemical formula 1, each of A1, A2, A3 and A4 is independently one of a non-substituted or substituted aromatic ring of C5 to C30 and a non-substituted or substituted hetero aromatic ring of C4 to C30. Each of A3 and A4 independently forms an aromatic ring or a hetero aromatic ring. Alternatively, an atom of the aromatic ring or the hetero aromatic ring of A3 and an atom of the aromatic ring or the hetero aromatic ring of A4 are combined with each other to form a fused ring. Each of L1 to L6 is independently selected from the group including a non-substituted or substituted alkylene group of C1 to C20, a non-substituted or substituted alkenylene group of C2 to C20, a non-substituted or substituted alkynylene group of C2 to C20, a non-substituted or substituted cycloalkylene group of C3 to C30, a non-substituted or substituted hetero cycloalkylene group of C3 to C30, a non-substituted or substituted arylene group of C5 to C30, a non-substituted or substituted hetero arylene group of C4 to C30, a non-substituted or substituted arylalkylene group of C6 to C30, a non-substituted or substituted hetero arylalkylene group of C6 to C30, a non-substituted or substituted aryloxylene group of C6 to C30, and a non-substituted or substituted hetero aryloxylene group of C6 to C30. Each of o, p, q, r, s and t is independently 0 or 1. Each of R1 to R12 is independently selected from the group including a hydrogen atom, a non-substituted or substituted alkyl group of C1 to C20, a non-substituted or substituted alkenyl group of C2 to C20, a non-substituted or substituted alkynyl group of C2 to C20, a non-substituted or substituted alkoxy group of C1 to C20, a non-substituted or substituted cycloalkyl group of C3 to C30, a non-substituted or substituted hetero cycloalkyl group of C3 to C30, a non-substituted or substituted of aryl group of C5 to C30, a non-substituted or substituted hetero aryl group of C4 to C30, a non-substituted or substituted arylalkyl group of C6 to C30, a non-substituted or substituted hetero arylalkyl group of C6 to C30, a non-substituted or substituted aryloxyl group of C6 to C30, a non-substituted or substituted hetero aryloxyl group of C6 to C30, alkylamine group of C1 to C20, a non-substituted or substituted aryl amine group of C5 to C30, and a non-substituted or substituted hetero aryl amine group of C5 to C30. And x is selected from the group including S, O, NR13, CR14R15 and SiR16R17. Each of R13 to R17 is independently selected from the group including a hydrogen atom, a non-substituted or substituted alkyl group of C1 to C20, a non-substituted or substituted alkenyl group of C2 to C20, a non-substituted or substituted alkynyl group of C2 to C20, a non-substituted or substituted alkoxy group of C1 to C20, a non-substituted or substituted cycloalkyl group of C3 to C30, a non-substituted or substituted hetero cycloalkyl group of C3 to C30, a non-substituted or substituted of aryl group of C5 to C30, a non-substituted or substituted hetero aryl group of C4 to C30, a non-substituted or substituted arylalkyl group of C6 to C30, a non-substituted or substituted hetero arylalkyl group of C6 to C30, a non-substituted or substituted aryloxyl group of C6 to C30, a non-substituted or substituted hetero aryloxyl group of C6 to C30, alkylamine group of C1 to C20, a non-substituted or substituted aryl amine group of C5 to C30, and a non-substituted or substituted hetero aryl amine group of C5 to C30. Each of a, b, c, d, e and f is independently 0 or 1, and at least one of a, b, c, d, e and f is 1.

The word of 'non-substituted' preferably means that a hydrogen atom is substituted, and the hydrogen atom includes protium, deuterium and tritium.

A substituent for the word of 'substituted' includes one of a non-substituted or substituted with halogen alkyl group, a non-substituted or substituted with halogen alkoxy group, halogen, a cyano group, a carboxyl group, a carbonyl group, an amine group, an alkylamine group, a nitro group, a hydrazyl group, a sulfonyl group, an alkyl silyl group, an alkoxy silyl group, a cycloalkyl silyl group and an aryl silyl group.

The word of 'hetero' in 'a hetero aromatic ring,' 'a hetero cycloalkylene group,' 'a hetero arylene group,' 'a hetero arylalkylene group,' 'a hetero aryloxylene group,' 'a hetero cycloalkyl group,' 'a hetero aryl group,' 'a hetero arylalkyl group,' 'a hetero aryloxyl group' and 'a hetero aryl amine group' means that at least one, for example, one to four, of carbon atoms constituting an aromatic ring or an aliphatic ring is substituted with at least one hetero atom selected from the group including N, O, P, Si, S and a combination thereof.

According to an exemplary embodiment, each of A1, A2, A3 and A4 in the chemical formula 1, may be independently one of a non-fused or fused aromatic ring such as a non-substituted or substituted phenyl, biphenyl, terphenyl, tetraphenyl, naphthalene, anthracene, indene, phenalene, phenanthrene, azulene, pyrene, fluorene, tetraphen, tetracene and spiro fluorene and a non-fused or fused hetero aromatic ring such as pyrrole, pyridine, pyrazine, pyrimidine, pyridazine, triazine, tetrazine, imidazole, pyrazole, carbazole, indole, quinoline, acridine, phenanthroline, furan, pyran, oxazine, oxazole, oxadiazole, triazole, dioxin, benzofuran, dibenzofuran, thiopyran, thiazine, thiophene, phosphine and N-substituted spiro fluorene.

L1 to L6 as a linker connecting a homo or hetero aromatic ring (A1 to A4) and a nitrogen atom of an amine group disposed at a terminal may be selected from the group including a non-substituted or substituted alkylene group of C1 to C20, a non-substituted or substituted arylene group of C5 to C30, a non-substituted or substituted hetero arylene group of C4 to C30, a non-substituted or substituted arylalkylene group of C6 to C30, a non-substituted or substituted hetero arylalkylene group of C6 to C30, a non-substituted or substituted aryloxylene group of C6 to C30 and a non-substituted or substituted hetero aryloxylene group of C6 to C30.

Specifically, each of L1 to L6 may be an aromatic linker such as a non-substituted or substituted arylene group of C5 to C30, a non-substituted or substituted hetero arylene group of C4 to C30, a non-substituted or substituted arylalkylene group of C6 to C30, a non-substituted or substituted hetero arylalkylene group of C6 to C30, a non-substituted or substituted aryloxylene group of C6 to C30 or a non-substituted or substituted hetero aryloxylene group of C6 to C30.

For example, an arylene group, a hetero arylene group, an aryl alkylene group, a hetero arylalkylene group, an aryloxylene group and a hetero aryloxylene group constituting L1 to L6 of a linker in the chemical formula 1 may be selected from the group including a non-substituted or substituted phenylene, naphthylene, fluorenylene, biphenylene, terphenylene and/or non-substituted or N-substituted spiro-fluorenylene. For example, L1 to L6 of a linker in the chemical formula 1 may be an aromatic linker connecting A1 to A4 of an aromatic ring or a hetero aromatic ring and a nitrogen atom capable of being substituted with R1 to R12 at a meta position or a para position.

According to an exemplary embodiment, each of R1 to R12 capable of substituting a nitrogen atom at a terminal of an organic compound represented by the chemical formula 1 and R13 to R17 constituting x of the chemical formula 1 may be independently selected from the group including a non-substituted or substituted alkyl group of C1 to C20, a non-substituted or substituted aryl group of C5 to C30, a non-substituted or substituted hetero aryl group of C4 to C30, a non-substituted or substituted arylalkyl group of C6 to C30, a non-substituted or substituted hetero arylalkyl group of C6 to C30, a non-substituted or substituted aryloxyl group of C6 to C30, a non-substituted or substituted hetero aryloxyl group of C6 to C30, an alkylamine group of C1 to C20, a non-substituted or substituted aryl amine group of C5 to C30 and a non-substituted or substituted hetero aryl amine group of C5 to C30.

Specifically, each of R1 to R17 may be independently a homo or hetero aromatic substitute such as a non-substituted or substituted aryl group of C5 to C30, a non-substituted or substituted hetero aryl group of C4 to C30, a non-substituted or substituted arylalkyl group of C6 to C30, a non-substituted or substituted hetero arylalkyl group of C6 to C30, a non-substituted or substituted aryloxyl group of C6 to C30, a non-substituted or substituted hetero aryloxyl group of C6 to C30, a non-substituted or substituted aryl amine group of C5 to C30 and a non-substituted or substituted hetero aryl amine group of C5 to C30.

For example, when R1 to R17 of the chemical formula 1 are a homo aromatic substituent, the homo aromatic substituent may be selected from the group including phenyl, biphenyl, terphenyl, tetraphenyl, naphthyl, anthracenyl, indenyl, phenalenyl, phenanthrenyl, azulenyl, pyrenyl, tetracenyl, fluorenyl, spiro-fluorenyl, phenoxyl and naphthlenoxyl. However, the homo aromatic substituent is not limited to that set forth herein.

In addition, when R1 to R17 of the chemical formula 1 are a hetero aromatic substituent, the hetero aromatic substituent may be selected from the group including pyrolyl, pyridyl, pyrazinyl, pyrimidyl, pyridazinyl, triazinyl, tetrazinyl, imidazolyl, pyrazolyl, carbazolyl, indolyl, quinolinyl, acridinyl, furanyl, pyrenyl, oxazinyl, oxazolyl, oxadizaolyl, triazolyl, dioxinyl, benzofuranyl, dibenzofuranyl, thiopyranyl, thiazinyl, thiophenyl, phosphinyl and N-substituted spiro-fluorenyl. However, the hetero aromatic substituent is not limited to that set forth herein.

According to an exemplary embodiment, L1 to L6 of a linker in the chemical formula 1 may be an aromatic linker, and R1 to R17 of a substituent in the chemical formula 1 may be an aromatic substituent. An amine group at a terminal of a chemical compound represented by the chemical formula 1 may function as an electron donor. When a substituent (R1 to R12) of an amine group is an aromatic substituent, the amine group may function as an effective electron donor. As a result, the substituent of the amine group may be used as a material for an organic material layer such as a HIL and/or a HTL of the LED.

When a linker (L1 to L6) connecting an aromatic ring (A1 to A4) and a nitrogen atom constituting the amine group at a terminal is an aromatic linker and R13 to R17 defining a substituent (R1 to R12) connected to a nitrogen atom at a terminal and x is an aromatic substituent, the linker and the substituent have a conjugated structure. As a result, the function of the amine group at a terminal of an organic compound of the chemical formula 1 as an electron donor is improved, and an emission property and an emission efficiency are improved. Accordingly, the organic compound may be used as a host or a dopant of an emitting material layer of the LED.

In an organic compound represented by the chemical formula 1, a core includes an aromatic ring moiety of a fused structure (a moiety where A1, A2 and x are connected), another aromatic ring (A3, A4) of a conjugated structure is connected to the core, and an amine group capable of being substituted with various functional groups is directly or indirectly connected to the aromatic ring moiety of a fused structure and another aromatic ring. Since the organic compound of the chemical formula 1 includes the aromatic core of a fused structure, a material stability such as a thermal stability is improved. When the organic compound is applied to the LED, an emission efficiency and a lifetime are improved. Since the organic compound has an excellent hole transport property, an excellent hole move property and an excellent emission efficiency, the organic compound is applied to an organic material layer of the LED.

In an organic compound according to an exemplary embodiment, A3 and A4 of the chemical formula 1 may form a fused structure together, and an aromatic ring core moiety of a fused structure and another aromatic ring moiety where A3 and A4 are fused together may have spiro structure. In an organic compound according to another exemplary embodiment, A3 and A4 of the chemical formula 1 may form individual and independent aromatic rings, and an aromatic ring core moiety of a fused structure is connected to A3 and A4, respectively, in a chain structure. For example, the organic compound where an aromatic ring core moiety of a fused structure and another fused aromatic ring moiety are connected to each other in a spiro structure may be represented by a following chemical formula 2. In addition, the organic compound where an aromatic ring core moiety of a fused structure is connected to A3 and A4 in a chain structure may be represented by a following chemical formula 3.

Chemical Formula 2

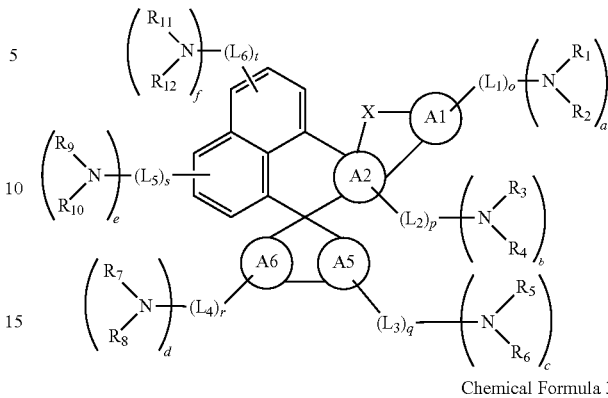

Chemical Formula 3

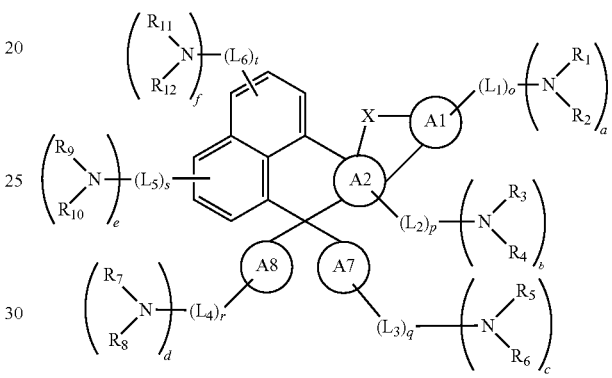

In the chemical formula 2 and the chemical formula 3, definitions of A1, A2, L1 to L6, o, p, q, r, s, t, R1 to R12, x, a, b, c, d, e and f are the same as those in the chemical formula 1. In the chemical formula 2, each of A5 and A6 is independently one of a non-substituted or substituted aromatic ring of C5 to C30 and a non-substituted or substituted hetero aromatic ring of C4 to C30. An atom of the aromatic ring or the hetero aromatic ring of A5 and an atom of the aromatic ring or the hetero aromatic ring of A6 are combined with each other to form a fused ring. In the chemical formula 3, each of A7 and A8 is independently one of a non-substituted or substituted aromatic ring of C5 to C30 and a non-substituted or substituted hetero aromatic ring of C4 to C30.

For example, each of A5 to A8 of the chemical formula 2 or the chemical formula 3 may be independently one of a non-fused or fused aromatic ring such as a non-substituted or substituted phenyl, biphenyl, terphenyl, tetraphenyl, naphthalene, anthracene, indene, phenalene, phenanthrene, azulene, pyrene, fluorene, tetrapen, tetracene and spiro fluorene and a non-fused or fused hetero aromatic ring such as pyrrole, pyridine, pyrazine, pyrimidine, pyridazine, triazine, tetrazine, imidazole, pyrazole, carbazole, indole, quinoline, acridine, phenanthroline, furan, pyran, oxazine, oxazole, oxadiazole, triazole, dioxin, benzofuran, dibenzofuran, thiopyran, thiazine, thiophene, phosphine and N-substituted spiro fluorene.

Since the organic compound of the chemical formula 2 or the chemical formula 3 includes a core of an aromatic ring of a fused structure, the organic compound has an excellent thermal stability. Since the organic compound of the chemical formula 2 or the chemical formula 3 includes a plurality of aromatic rings having a conjugated structure and an amine group functioning as an electron donor and connected thereto at a terminal, the organic compound of the chemical formula 2 or 3 has an excellent emission property, an excellent hole transport property and an excellent hole move property. As a result, the organic compound of the chemical formula 2 or 3 may be used for an organic material layer such as an EML, a HTL and/or a HIL of the LED.

According to an exemplary embodiment, an organic compound may be applied to an organic material layer of the LED even when an aromatic ring and/or a hetero aromatic ring (A1 to A8), a linker (L1 to L6), a functional group (R1 to R12) connected to a nitrogen atom at a terminal and a functional group (R13 to R17) defining x of the chemical formulas 1 to 3 are not substituted (e.g., even when a substituent is a hydrogen atom, a deuterium atom and/or a tritium atom). According to another exemplary embodiment, at least one of an aromatic ring and/or a hetero aromatic ring (A1 to A8), a linker (L1 to L6), a functional group (R1 to R12) connected to a nitrogen atom at a terminal and a functional group (R13 to R17) defining x of the chemical formulas 1 to 3 may be substituted with an electron withdrawing group and/or an electron donor group.

As an unlimited embodiment, the electron withdrawing group and/or the electron donor group capable of substituting A1 to A8, L1 to L6 and R1 to R17 of the chemical formulas 1 to 3 may be selected from the group including a non-substituted or substituted alkyl group of C1 to C20, a non-substituted or substituted with halogen alkoxy group of C1 to C20, halogen, a cyano group, a carboxyl group, a carbonyl group, an amine group, an alkylamine group of C1 to C10, a nitro group, a hydrazyl group, a sulfonyl group, a non-substituted or substituted aryl group of C5 to C30, a non-substituted or substituted hetero aryl group of C4 to C30, a non-substituted or substituted alkyl silyl group of C1 to C10, a non-substituted or substituted alkoxy silyl group of C1 to C10, a non-substituted or substituted cycloalkyl silyl group of C4 to C20 and a non-substituted or substituted aryl silyl group of C5 to C20.

An example of an alkyl group is one of methyl, ethyl, propyl, isopropyl, isobutyl, sec-butyl, tert-butyl, pentyl, iso-amyl and hexyl, and at least one hydrogen atom of the alkyl group may be substituted with a halogen atom such as fluorine.

An example of an alkoxy group is one of methoxy, ethoxy, propoxy, isobutyloxy, sec-butyloxy, pentyloxy, iso-amyloxy and hexyloxy, and at least one hydrogen atom of the alkoxy group may be substituted with a halogen atom such as fluorine.

An example of an alkyl silyl group, an alkoxy silyl group and an aryl silyl group is one of trimethylsilyl, triethylsilyl, triphenylsilyl, trimethoxysilyl, dimethoxyphenylsilyl, diphenylmethylsilyl, silyl, diphenylvinylsilyl, methylcyclobutylsilyl and dimethylpurinylsilyl, and at least one hydrogen atom of the silyl group may be substituted with another atom.

For example, when at least one of an aromatic ring and/or a hetero aromatic ring (A1 to A8), a linker (L1 to L6), a functional group (R1 to R12) connected to a nitrogen atom at a terminal and a functional group (R13 to R17) defining x of the chemical formulas 1 to 3 is substituted with an electron withdrawing group and/or an electron donor, the organic compound may be used as a host or a dopant of an emitting material layer of the LED having various purities (from a high color purity of blue to a low color purity of green). Accordingly, the organic compound may be applied to an EML, a HTL and/or a HIL of the LED.

An organic compound according to an embodiment of the present disclosure may be one of materials represented by a following chemical formula 4.

Chemical Formula 4

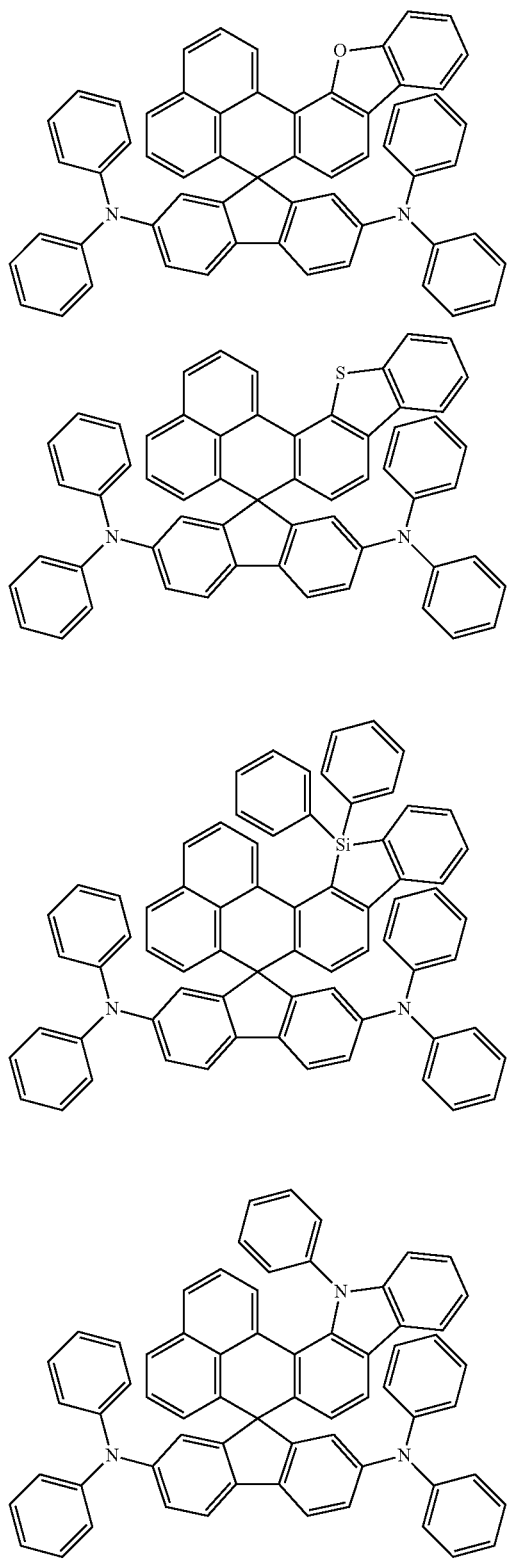

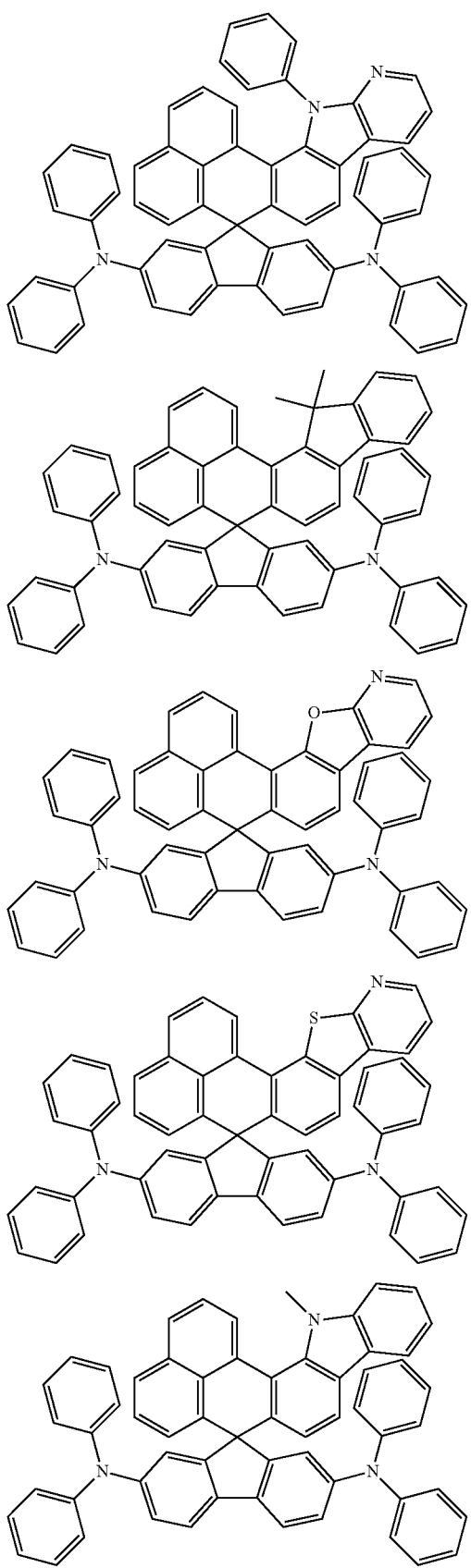
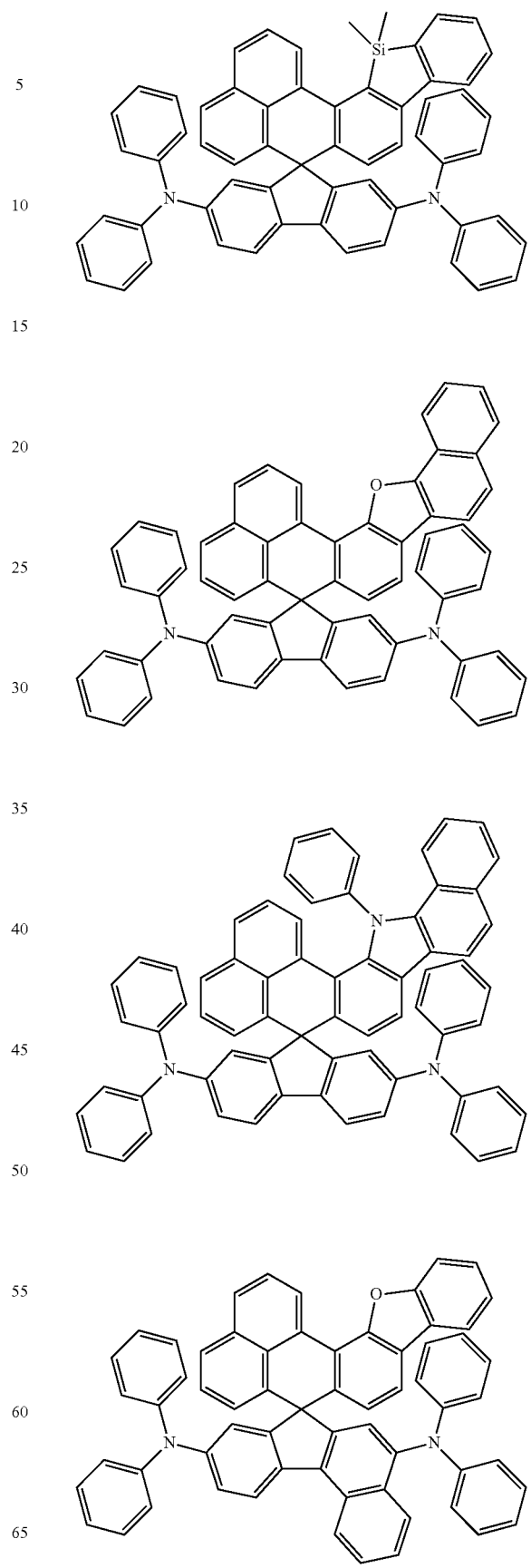

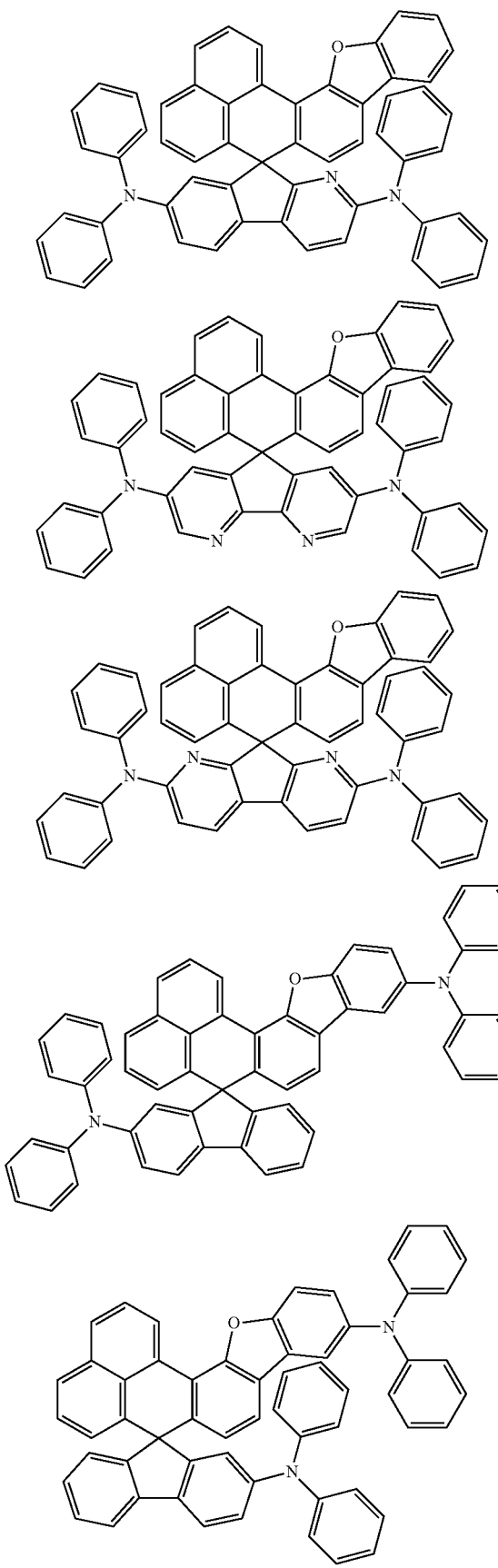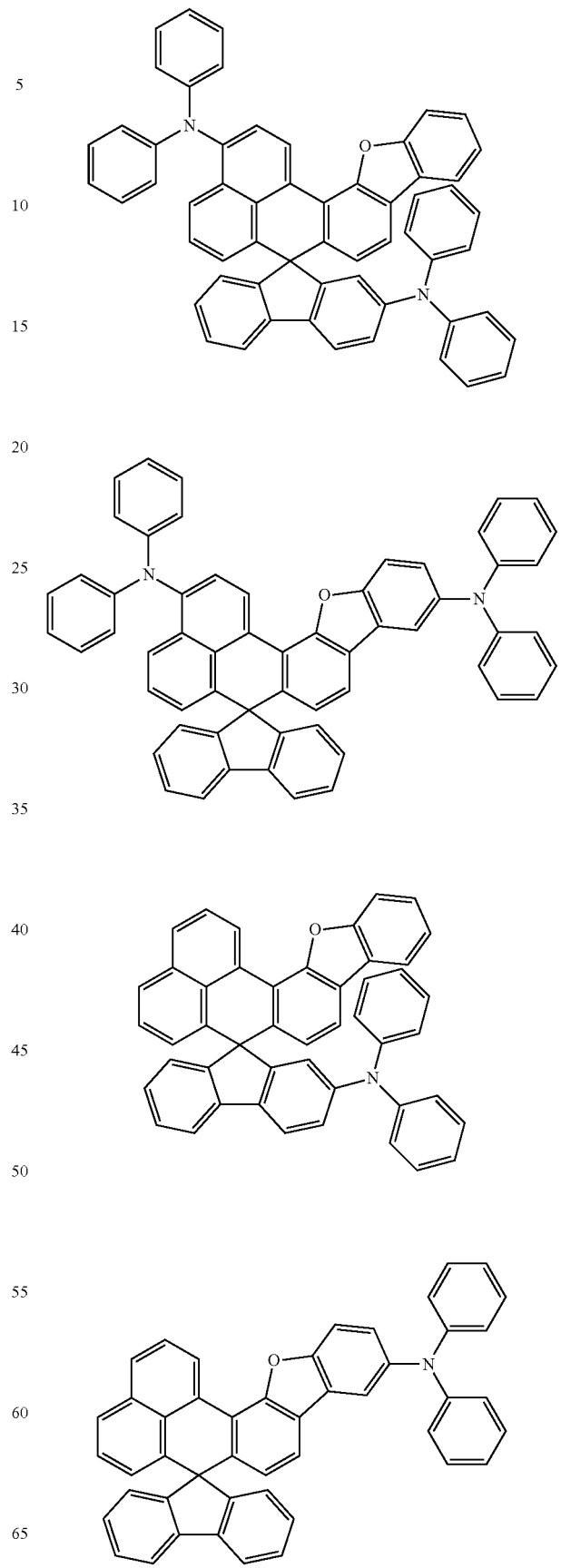

-continued
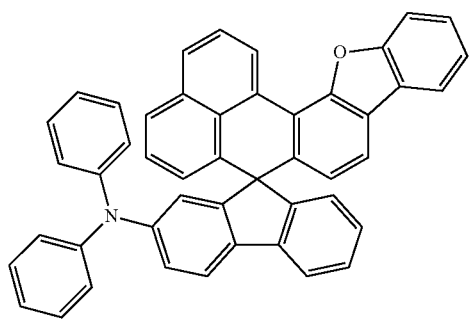
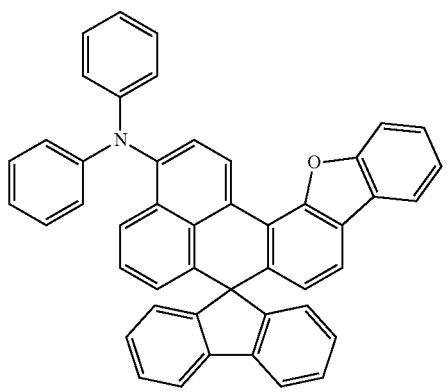
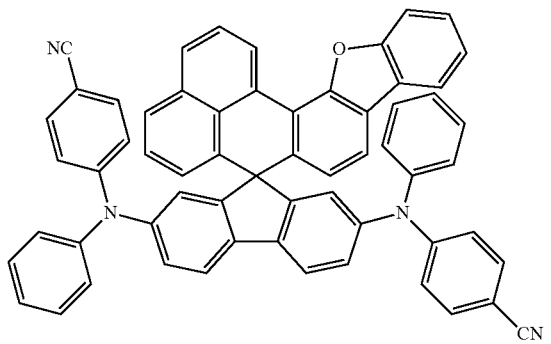
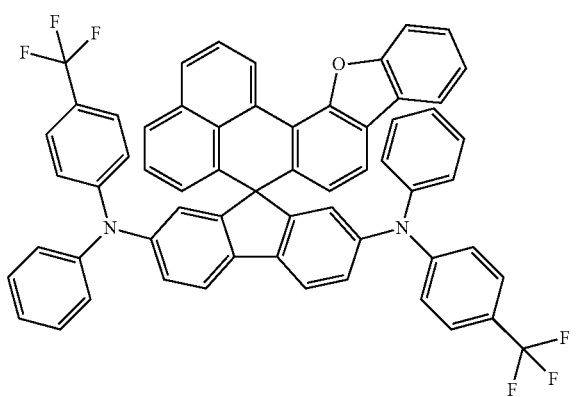
-continued
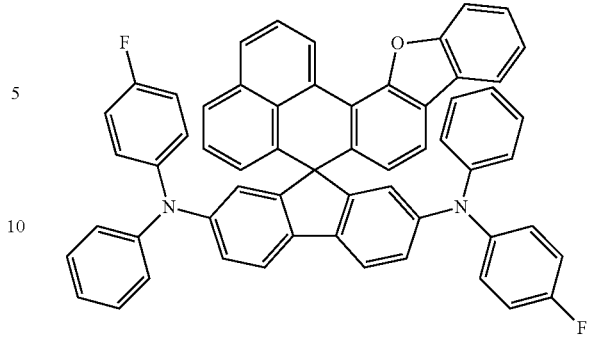
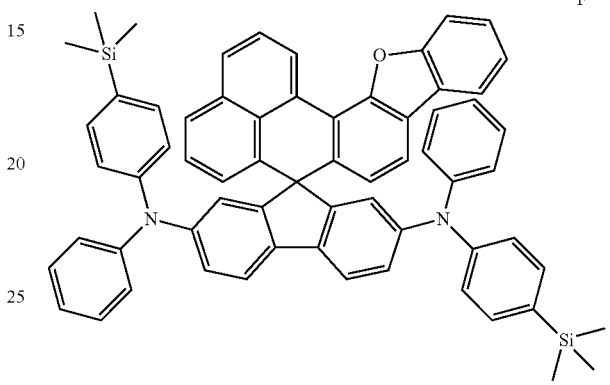
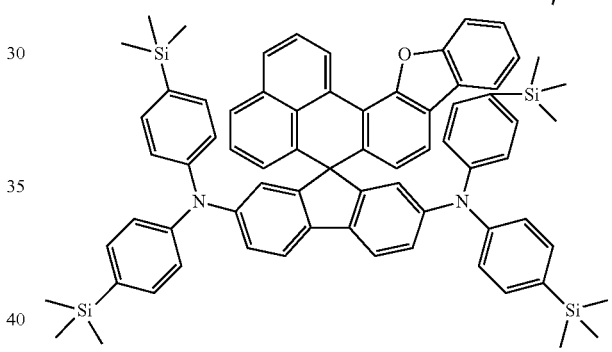
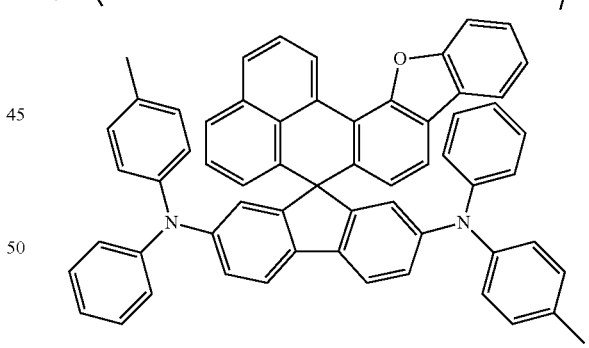
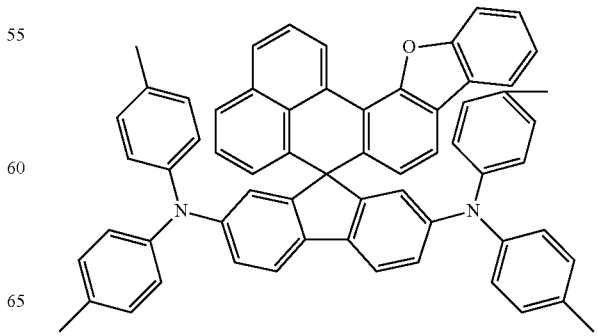

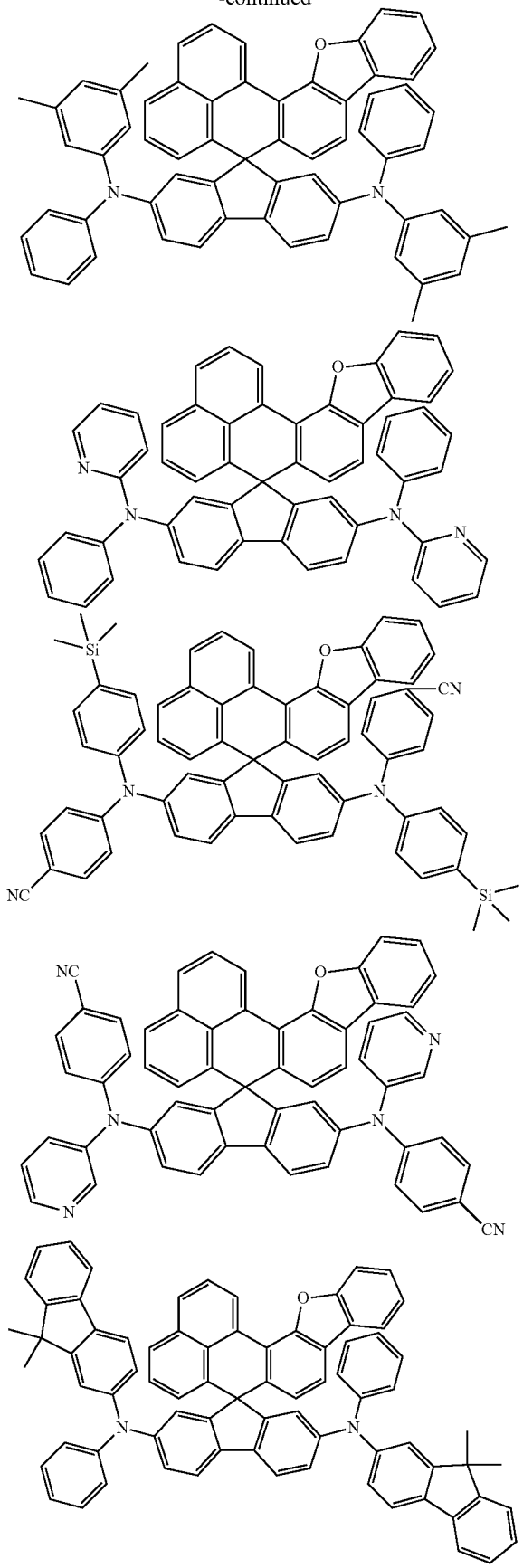
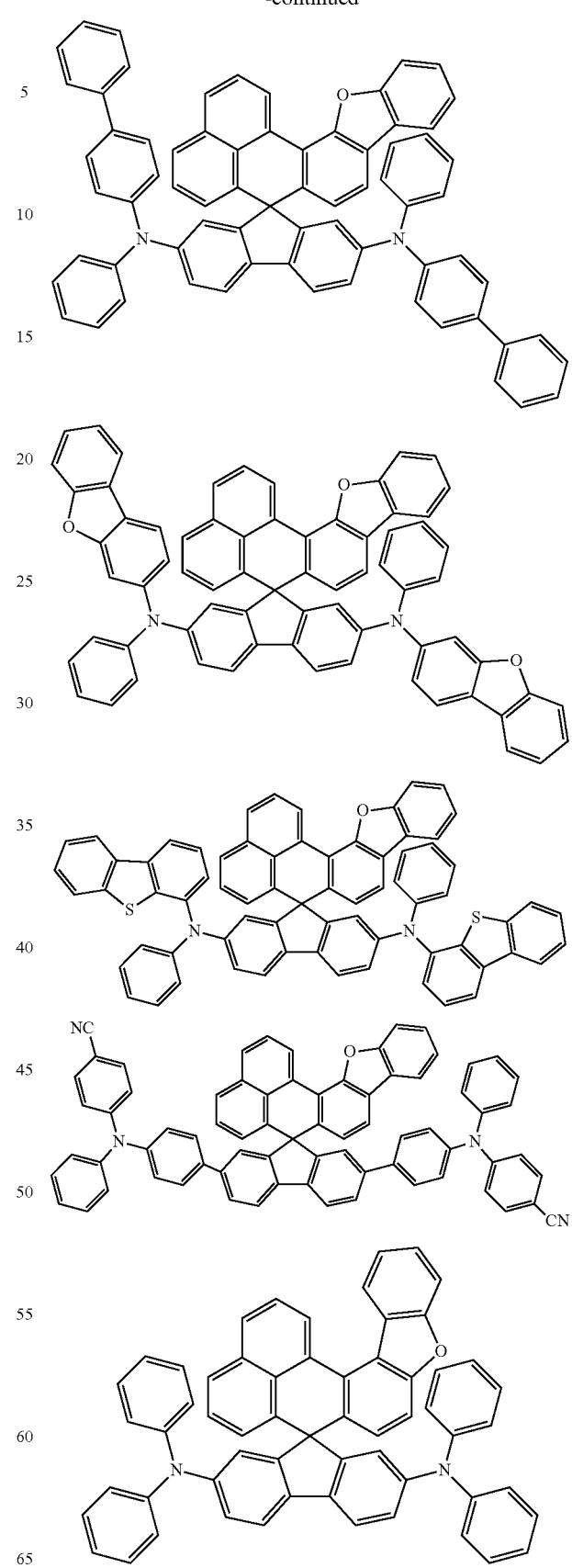

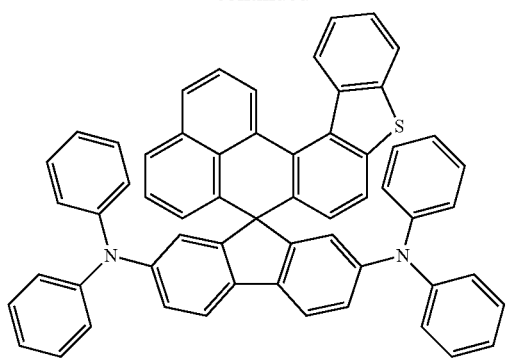
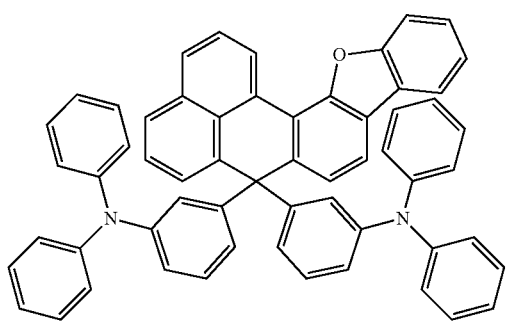
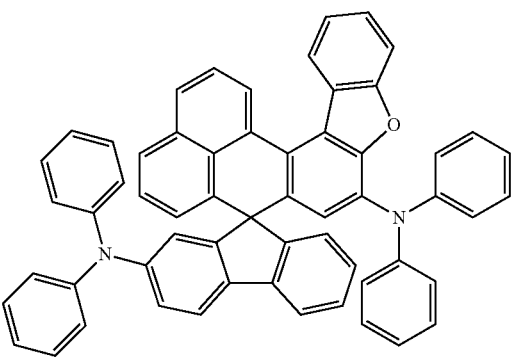
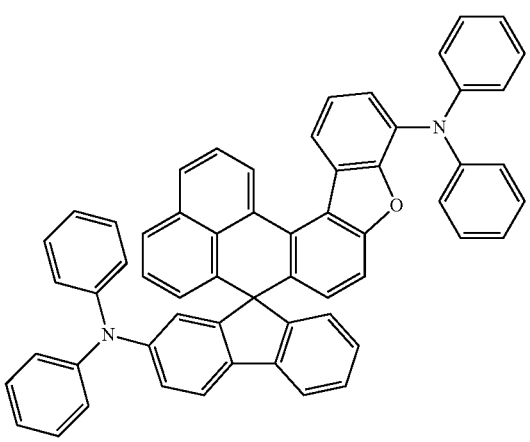
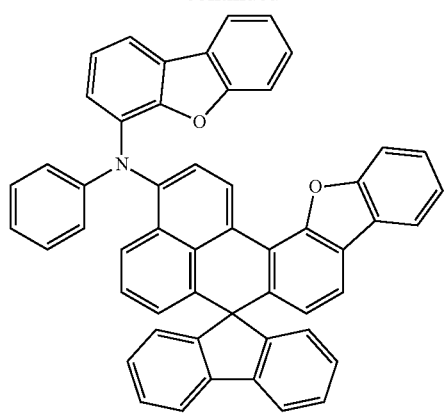
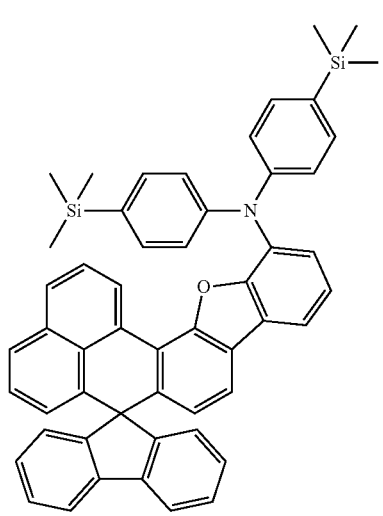
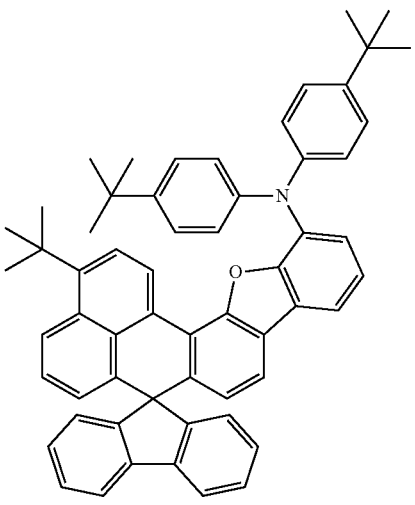

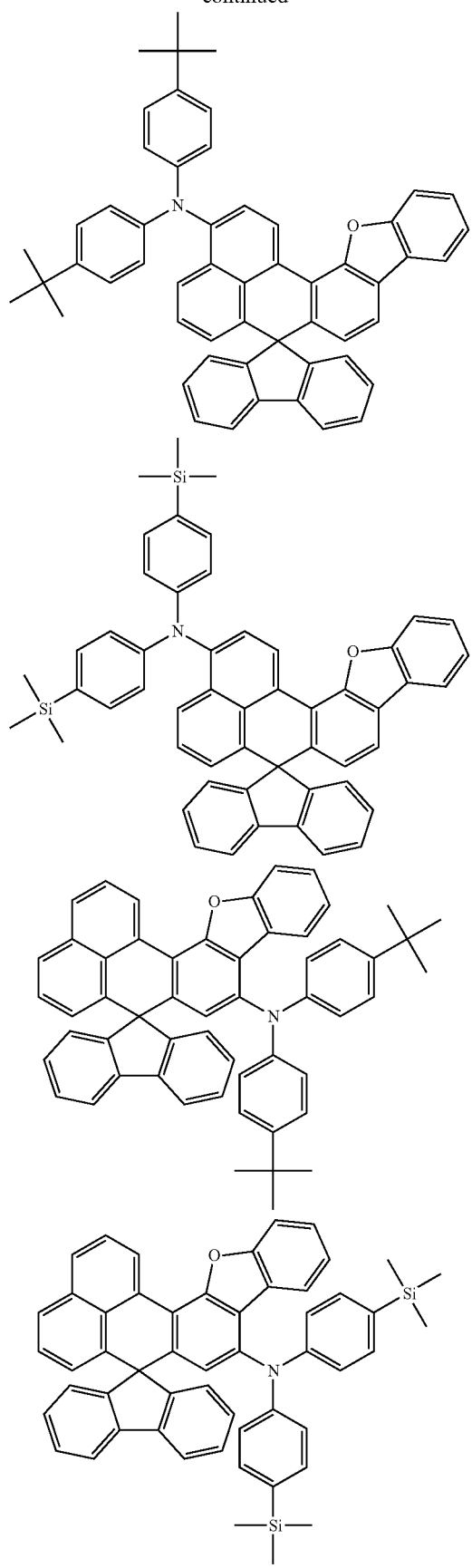
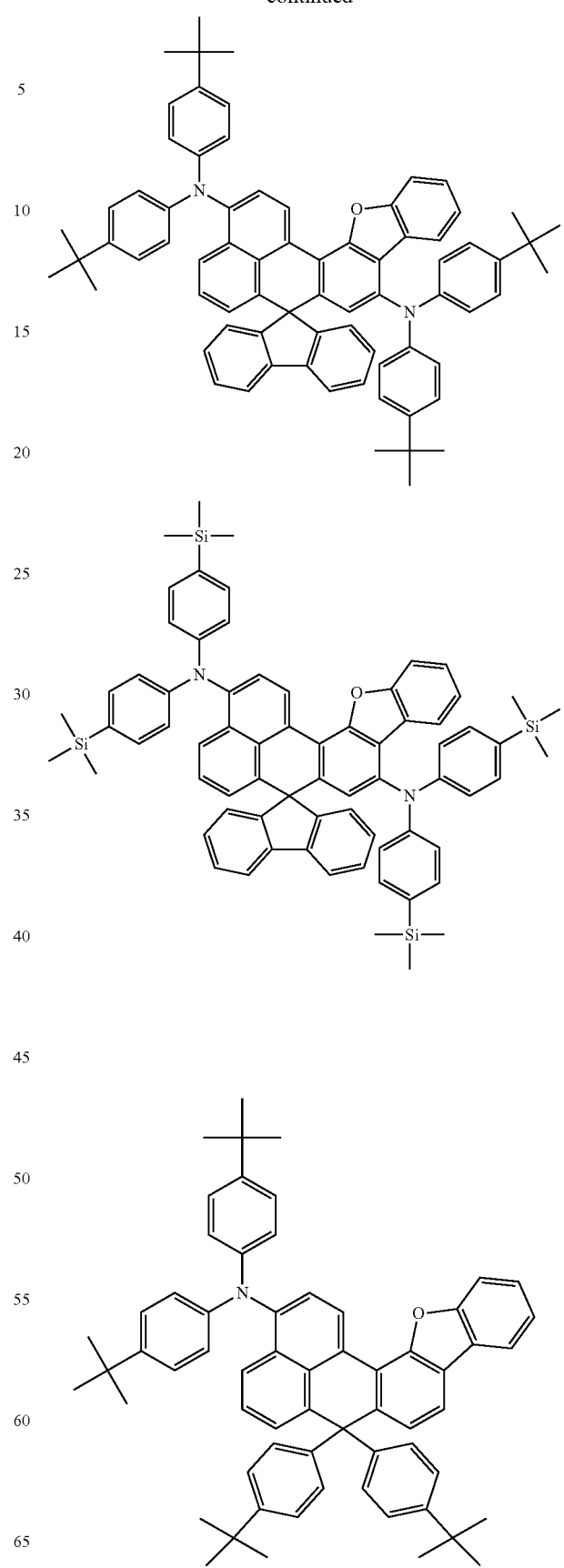

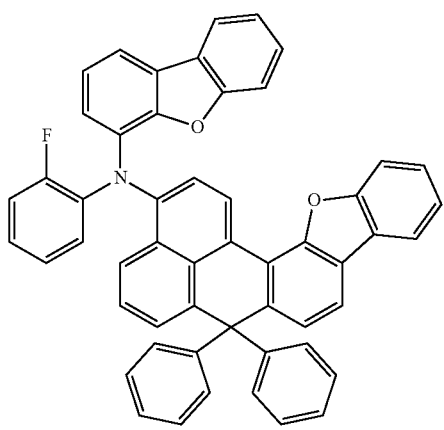
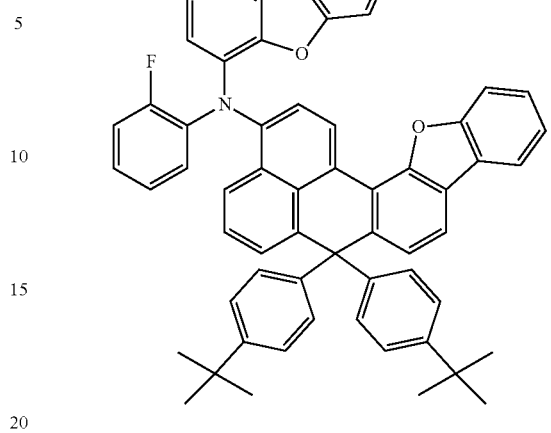
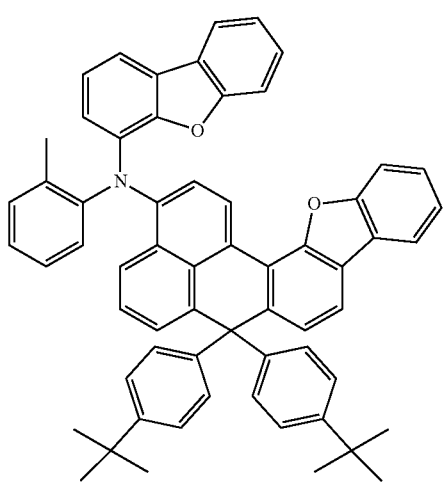
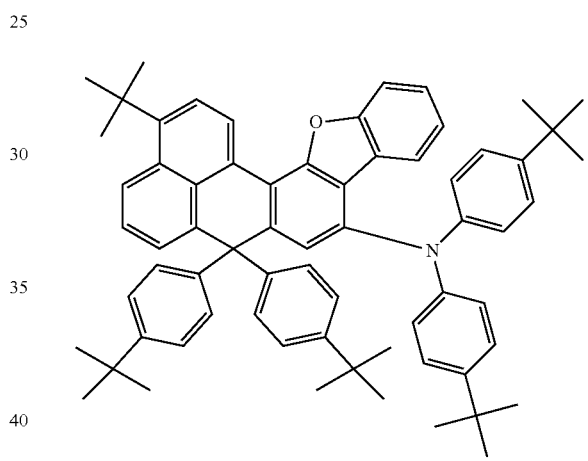
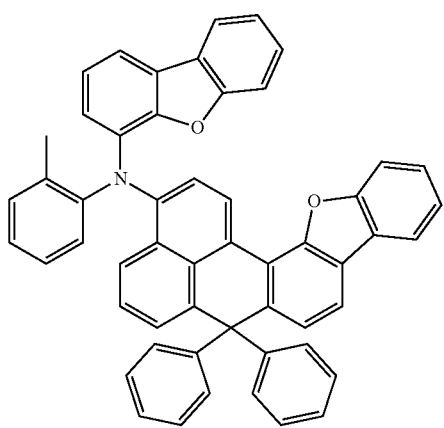
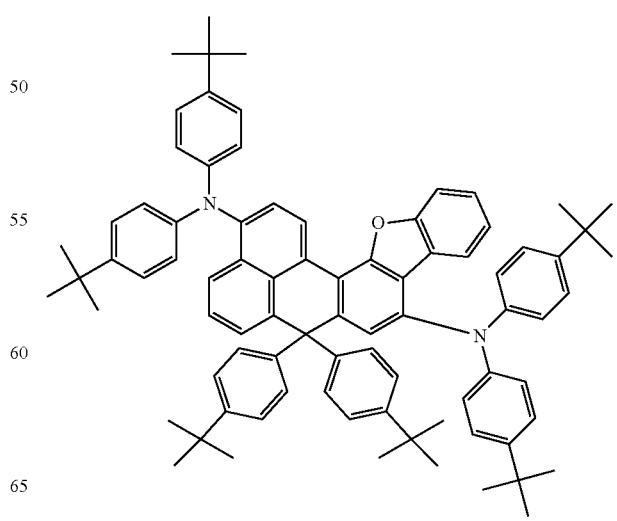

-continued
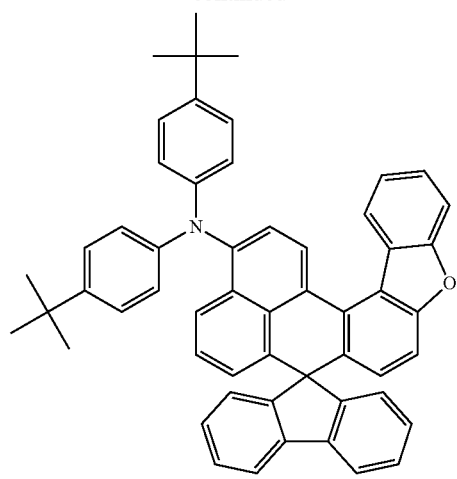
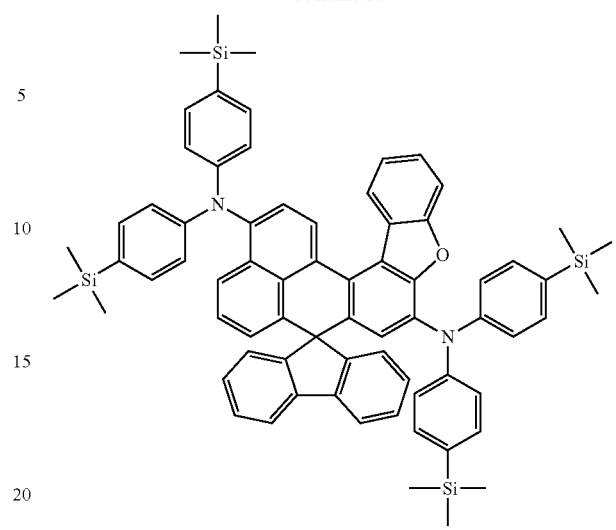
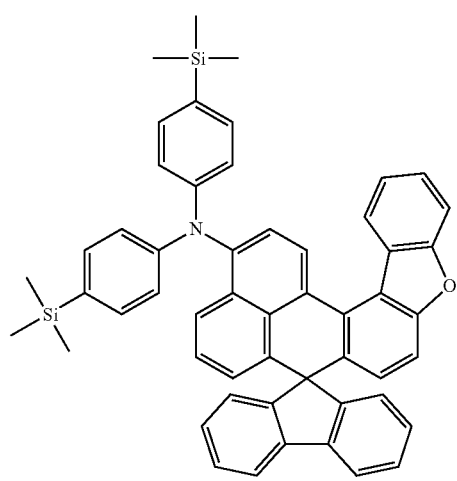
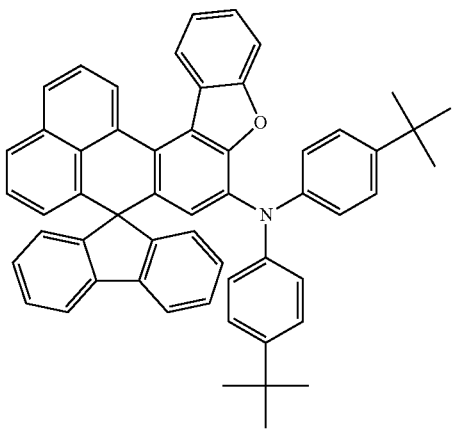
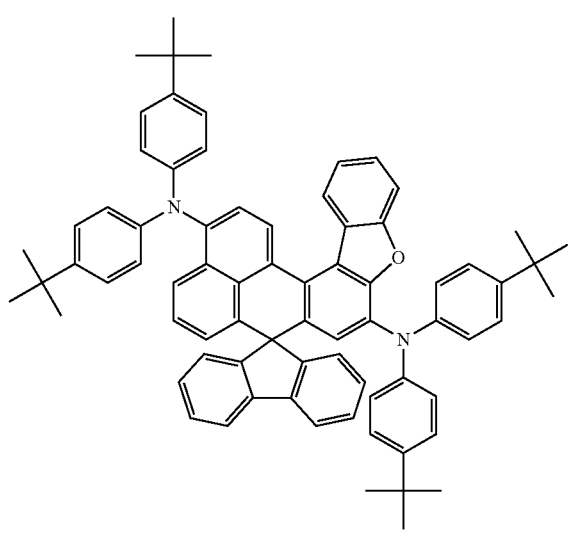
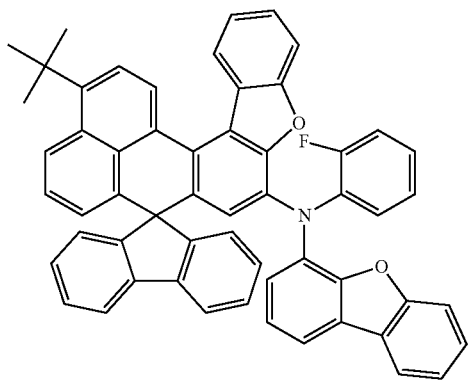

31
-continued
32
-continued
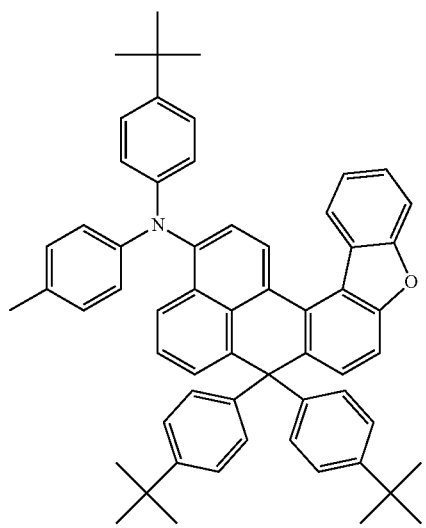
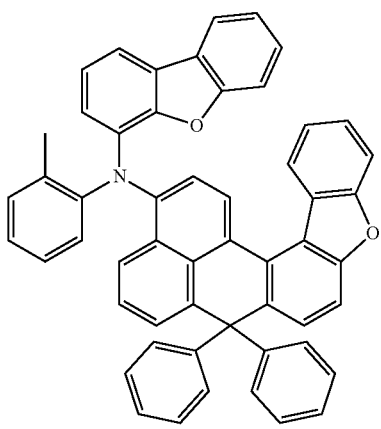
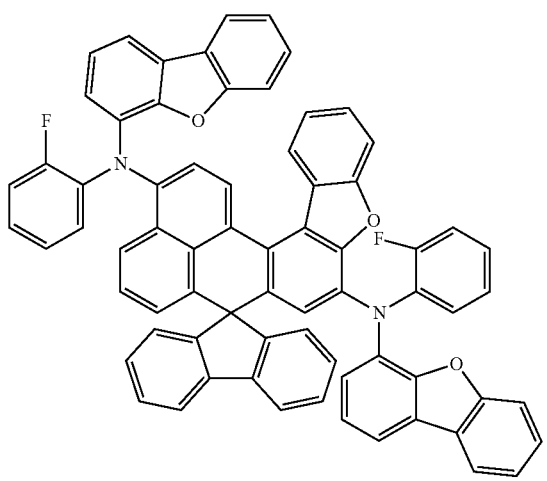
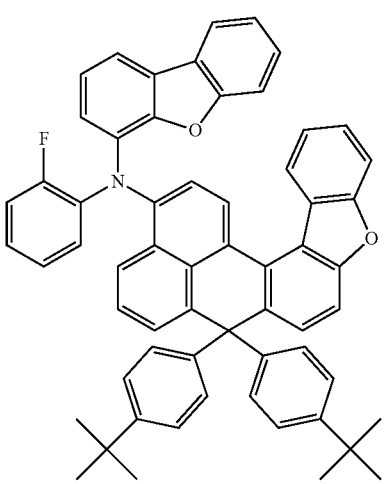
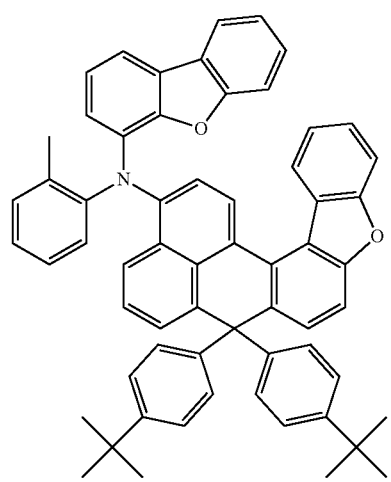
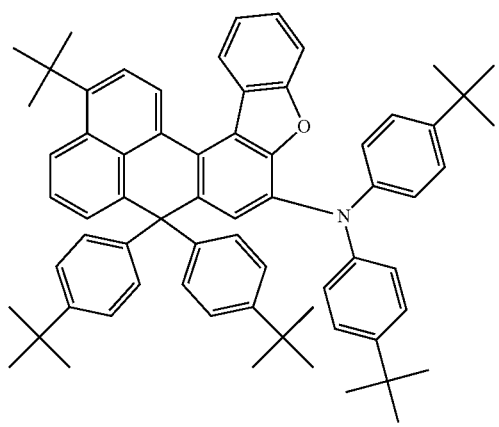

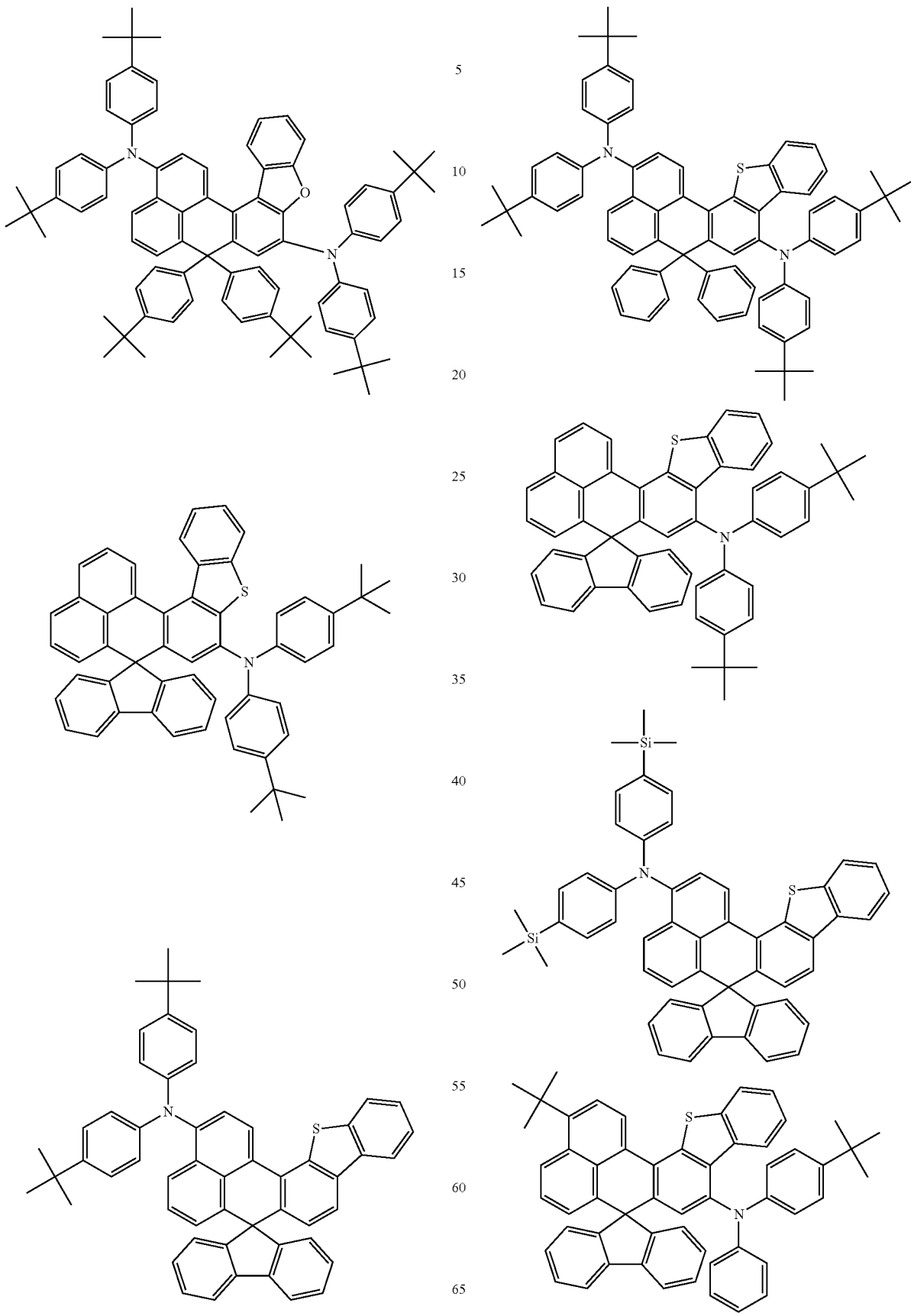

35
-continued
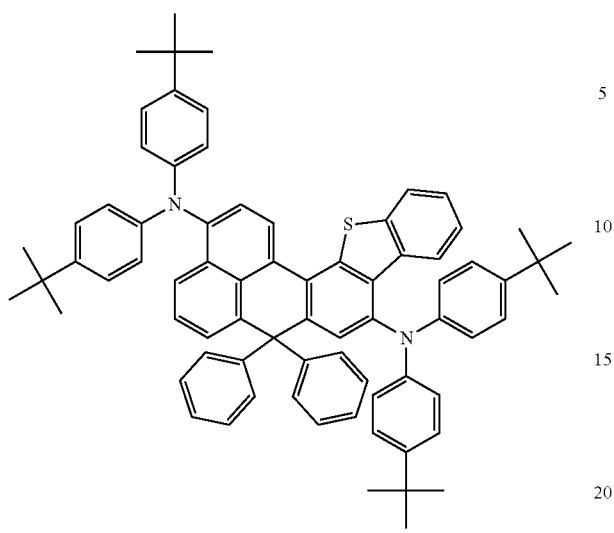
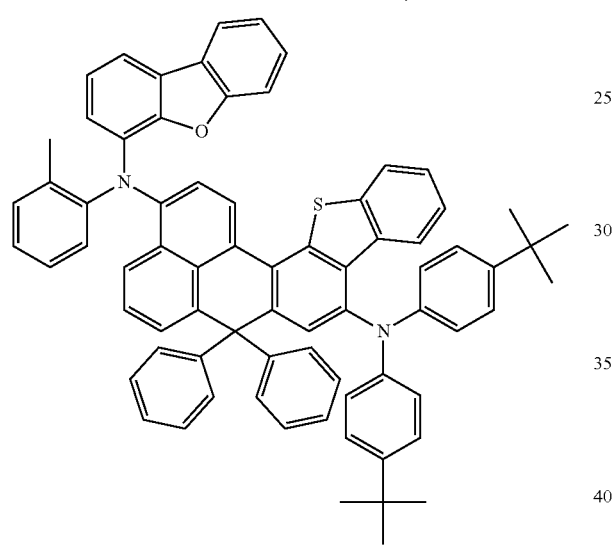
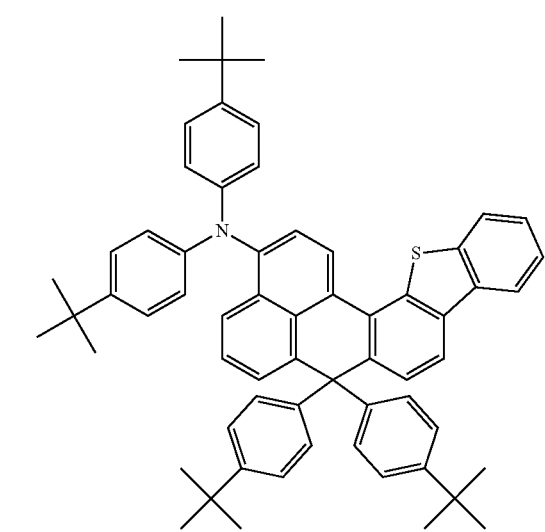
36
-continued
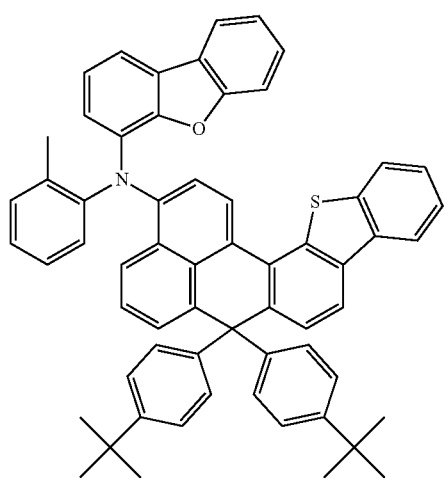
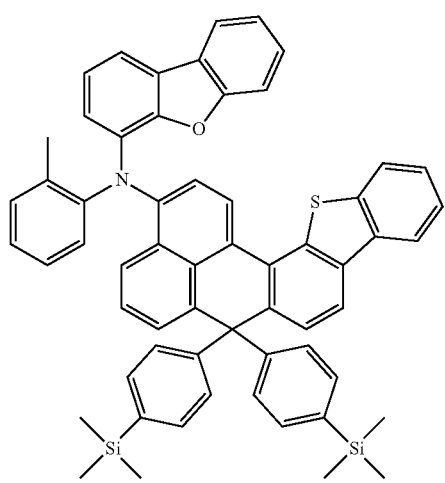
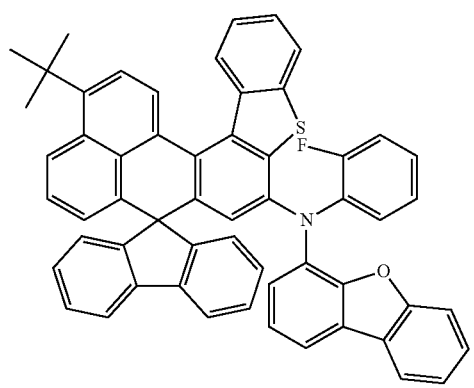

-continued
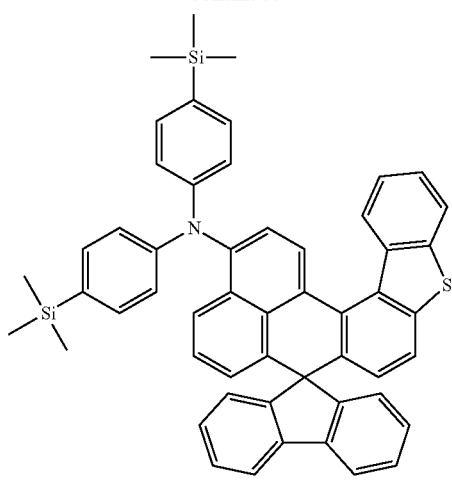
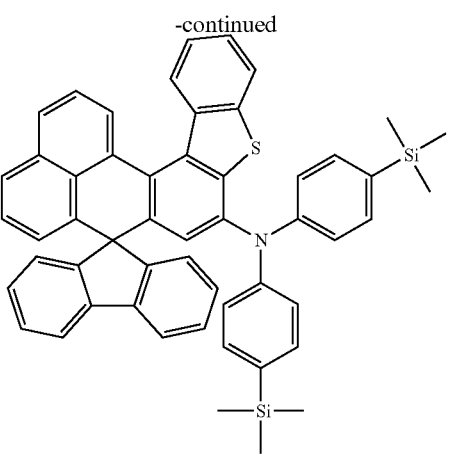
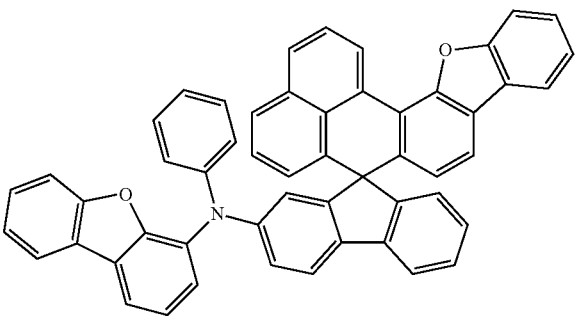
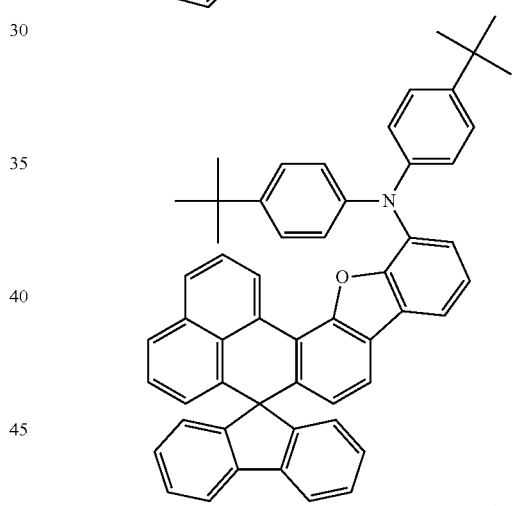
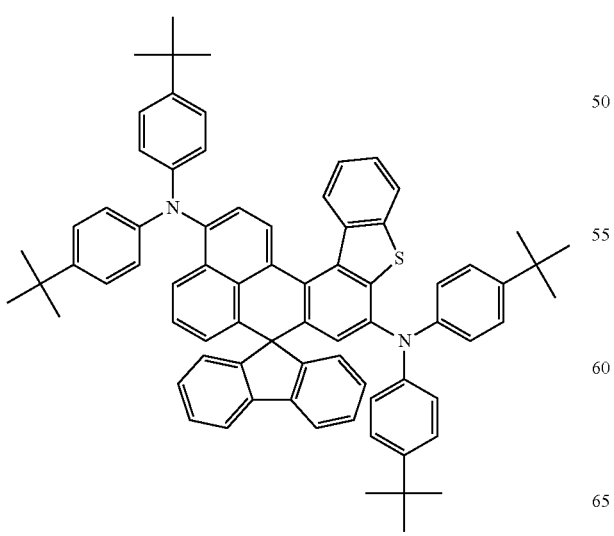
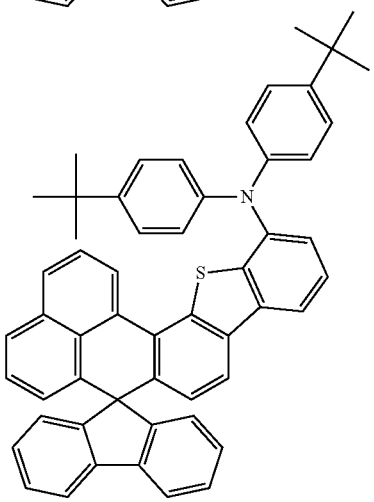

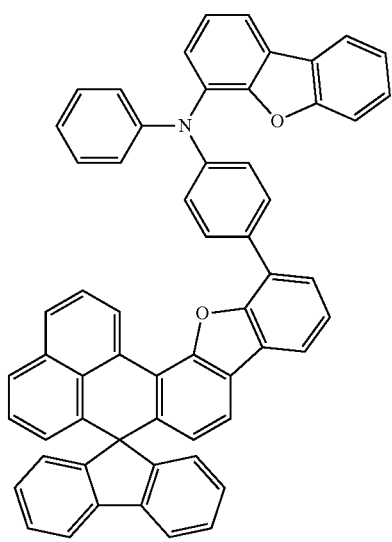
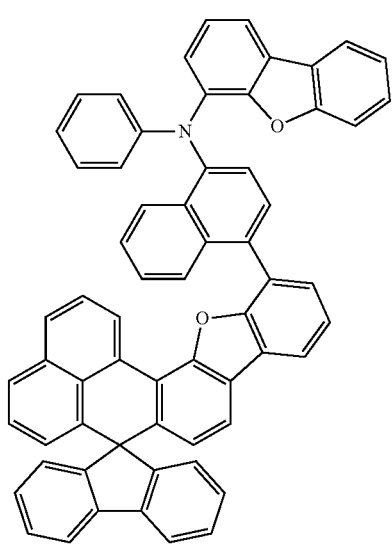
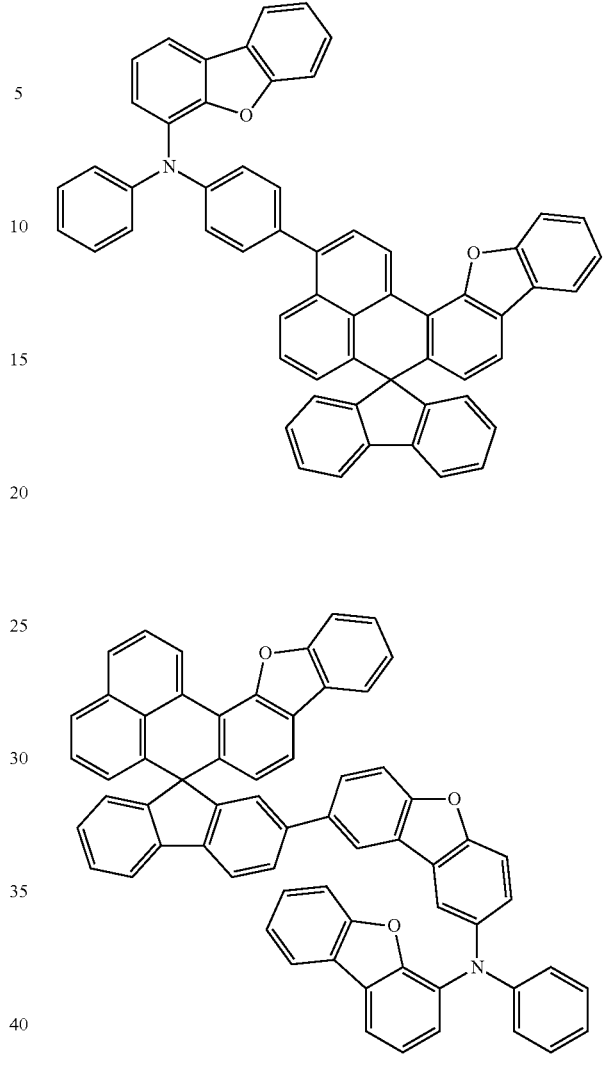

Since an organic compound represented by the chemical formula 4 includes an aromatic ring as a core, the organic compound has a thermal stability. The organic compound includes a plurality of aromatic rings having a conjugated structure, and an amine group at a terminal may function as an electron donor. When the organic compound represented by the chemical formula 4 is applied to the LED, an emission efficiency, a lifetime, an emission property and a hole transport property are improved. As a result, the organic compound represented by the chemical formula 4 may be applied to an organic material layer of the LED.

In an exemplary embodiment, an organic compound represented by the chemical formula 2 has a spiro structure where an aromatic core moiety (a moiety connected to A1 and A2) having a fused structure and another aromatic moiety (a moiety including A3 and A4) having a fused structure are connected to each other through a common atom. For example, in the organic compound represented by the chemical formula 2, an aromatic ring (A1, A2, A5, A6) and a nitrogen atom constituting a terminal amine group are directly connected to each other without a linker (L1 to L6). The organic compound may be represented by a following chemical formula 5.

Chemical Formula 5

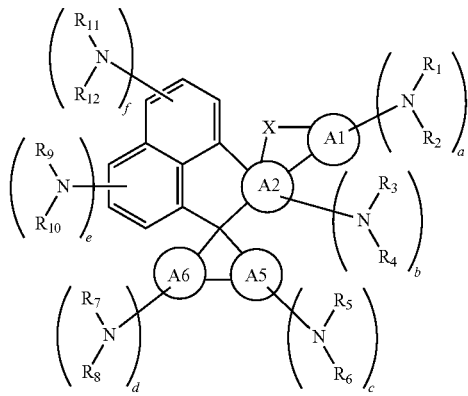

In the chemical formula 5, definitions of A1, A2, R1 to R12, x, a, b, c, d, e and f are the same as those in the chemical formula 1. Each of A5 and A6 is independently one of a non-substituted or substituted aromatic ring of C5 to C30 and a non-substituted or substituted hetero aromatic ring of C4 to C30. An atom of the aromatic ring or the hetero aromatic ring of A5 and an atom of the aromatic ring or the hetero aromatic ring of A6 are combined with each other to form a fused ring.

In an organic compound represented by the chemical formula 2 or 5, an aromatic moiety (a moiety connected to A1 and A2) of a core having a fused structure and another aromatic moiety (a moiety including A3 and A4) having a fused structure are connected to each other in a spiro structure. Since the two fused aromatic rings are connected to each other in a spiro structure, a glass transition temperature (Tg) of the organic compound increases and a thermal stability of the organic compound is improved. As a result, when the organic compound is used for an organic material layer of the LED, an emission efficiency and a lifetime are improved.

In an organic compound represented by the chemical formula 3 according to another embodiment, an aromatic core moiety (a moiety connected to A1 and A2) having a fused structure and another aromatic moiety (a moiety including A3 and A4) having a fused structure are connected to each other in a chain structure. For example, in the organic compound represented by the chemical formula 3, an aromatic ring (A1, A2, A7, A8) and a nitrogen atom constituting a terminal amine group are directly connected to each other without a linker (L1 to L6). The organic compound may be represented by a following chemical formula 6.

Chemical Formula 6

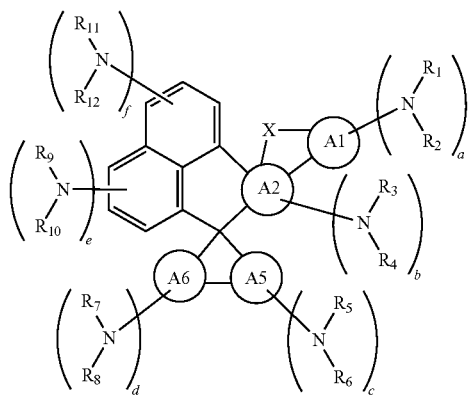

In the chemical formula 6, definitions of A1, A2, R1 to R12, x, a, b, c, d, e and f are the same as those in the chemical formula 1. Each of A7 and A8 is independently one of a non-substituted or substituted aromatic ring of C5 to C30 and a non-substituted or substituted hetero aromatic ring of C4 to C30.

As in the chemical formulas 5 and 6, when a plurality of aromatic rings (A1, A2, A5, A6) having a conjugated structure is directly connected to a nitrogen atom constituting a terminal amine group functioning as an electron donor, an electron donor property of the amine group is improved, and an emission property and a hole transport property are improved through the conjugated structure. As a result, the organic compound of the chemical formula 5 may be applied to an organic material layer such as an EML, a HTL and/or a HIL of the LED.

[Light Emitting Diode and Display Device]

Since an organic compound represented by the chemical formulas 1 to 5 according to an embodiment of the present disclosure has an excellent thermal stability, an excellent hole transport property and/or an excellent emission property, the organic compound may be applied to an emission material layer of the LED. A structure of the LED according to an embodiment of the present disclosure will be illustrated hereinafter.

FIG. 1 is a cross-sectional view showing a light emitting diode according to a first embodiment of the present disclosure. All the components of the light emitting diode according to all embodiments of the present disclosure are operatively coupled.

In FIG. 1, a light emitting diode (LED) 100 according to the first embodiment of the present disclosure includes first and second electrodes 110 and 120 facing each other, an organic material layer 130 between the first and second electrodes 110 and 120, and an electron transporting layer (ETL) 170 and an electron injecting layer (EIL) 180 sequentially disposed between the organic material layer 130 and the second electrode 120. The organic material layer 130 includes a hole injecting layer (HIL) 140, a hole transporting layer (HTL) 150 and an emitting material layer (EML) 160 sequentially formed on the first electrode 110.

The first electrode 110 may include a conductive material of a relatively high work function to form an anode. For example, the first electrode 110 may include one of indium-tin-oxide (ITO) and indium-zinc-oxide (IZO).

The second electrode 120 may include a conductive material of a relatively low work function to form a cathode. For example, the second electrode 120 may include one of aluminum (Al), magnesium (Mg), calcium (Ca), silver (Ag) and an alloy thereof.

The HIL 140 is disposed between the first electrode 110 and the HTL 150, and an interface property between the first electrode 110 and the HTL 150 of an organic material layer is improved by the HIL 140. The HIL 140 may include an organic compound represented by the chemical formulas 1 to 5, or a hole injecting host material doped with an organic compound represented by the chemical formulas 1 to 5.

When the HIL 140 includes the hole injecting host material and the organic compound represented by the chemical formulas 1 to 5, the hole injecting host material may include 4,4',4"-tris(3-methylphenylphenylamino)triphenylamine (MTDATA), copper phthalocyanine (CuPc), tris(4-carbazoyl-9-ylphenyl)amine (TCTA), N,N'-diphenyl-N,N'-bis(1-naphthyl)-1,1'-biphenyl-4,4"-diamine (NPB), 1,4,5,8,9,11-hexaazatriphenylenehexacarbonitrile (HATCN) and/or poly (3,4-ethylenedioxythiophene)polystyrene sulfonate (PEDOT/PSS) and may be doped with the organic compound of the chemical formulas 1 to 5 by about 0.1 wt % to about 50 wt %. However, the HIL 140 is not limited to that set forth herein.

The HTL 150 is disposed between the first electrode 110 and the EML 160 to be adjacent to the EML 160. The HTL 150 may include an organic compound represented by the chemical formulas 1 to 5, or a hole transporting host material doped with an organic compound represented by the chemical formulas 1 to 5.

When the HTL 150 includes the hole transporting host material and the organic compound represented by the chemical formulas 1 to 5, the hole transporting host material may be N,N'-diphenyl-N,N'-bis(3-methylphenyl)-1,1'-biphenyl-4,4'-diamine (TPD) and/or N,N'-di(naphthalen-1-yl)-N,N'-diphenylbenzidine (NPB), and may be doped with the organic compound represented by the chemical formulas 1 to 5 by about 0.1 wt % to about 50 wt %. However, the HTL 150 is not limited to that set forth herein.

To improve an emission efficiency of the LED 100, the EML 160 may include a host doped with a dopant. In an exemplary embodiment, a host of the EML 160 may be doped with a dopant of the organic compound represented by the chemical formulas 1 to 5.

For example, when the EML 160 is formed to emit a blue (B) light, the EML 160 may include a blue host material selected from the group including an anthracene derivative, a pyrene derivative, a perylene derivative and a combination thereof doped with the organic compound represented by the chemical formulas 1 to 5. The blue host material may be selected from the group including 4,4'-bis(2,2'-diphenylyinyl)-1,1'-biphenyl(DPAVBi), 9,10-di-(2-naphtyl)anthracene (α-ADN), 2,5,8,11-tetra-t-butylperylene (TBP), 2-tert-butyl-9,10-di(2-naphthyl)anthracene (TBADN), 2-methyl-9,10-di(2-naphtyl)anthracene (MADN), 2,2',2"-(1,3,5-benzinetriyl)-tris(1-phenyl)-1-H-benzimidazole (TBPi) and a combination thereof. However, the EML 160 is not limited to that set forth herein.

When the EML 160 is formed to emit a green (G) or yellow-green (YG) light, the EML 160 may include a G or YG host material of a carbazole compound and/or a metal complex doped with the organic compound represented by the chemical formulas 1 to 5. The G or YG host material may be selected from the group including dp$_2$Ir(acac), op$_2$Ir (acac) and a combination thereof. However, the EML 160 is not limited to that set forth herein.

When the EML 160 is formed to emit a red (R) light, the EML 160 may include a R host material of a carbazole compound and/or a metal complex doped with the organic compound represented by the chemical formulas 1 to 5. The red host material may include Btp$_2$Ir(acac). However, the EML 160 is not limited to that set forth herein.

When the organic compound of the chemical formulas 1 to 5 is used as a dopant of the EML 160, the dopant may be added to the host by about 0.1 wt % to about 50 wt % with respect to the host.

In another exemplary embodiment, an organic compound of the chemical formulas 1 to 5 may be used as a host, for example, a phosphorous host, of the EML 160.

For example, when the EML 160 is formed to emit a blue (B) light, the EML 160 may include a host of the organic material of the chemical formulas 1 to 5 doped with a B phosphorous dopant. The B phosphorous dopant may include Bis[2-(4,6-difluorophenyl)pyridinato-C2,N](picolinato)iridium(III) (FIrpic). However, the EML 160 is not limited to that set forth herein.

When the EML 160 is formed to emit a green (G) or yellow-green (YG) light, the EML 160 may include a host material of a carbazole compound and/or a metal complex doped with the organic compound of the chemical formulas 1 to 5. The G or YG host material may be selected from the group including dp$_2$Ir(acac), op$_2$Ir(acac) and a combination thereof. However, the EML 160 is not limited to that set forth herein.

When the EML 160 is formed to emit a red (R) light, the EML 160 may include a R host material of a carbazole compound and/or a metal complex doped with the organic compound of the chemical formulas 1 to 5. The red host material may include Btp$_2$Ir(acac). However, the EML 160 is not limited to that set forth herein.

When the organic compound of the chemical formulas 1 to 5 is used as a dopant of the EML 160, the dopant may be added to the host by about 0.1 wt % to about 50 wt % with respect to the host.

The ETL 170 and the EIL 180 are sequentially formed between the organic material layer 130 and the second electrode 120. The ETL 170 may include a material of a relatively high electron mobility, and may supply an electron to the EML 160 through an excellent electron transport. For example, the ETL 170 may include an electron transport material such as oxadiazole, triazole, phenanthroline, benzoxazole, benzthiazole and/or benzimidazole (for example, 2-[4-(9,10-Di-2-naphthalenyl-2-anthracenyl)phenyl]-1-phenyl-1H-benzimidazole). However, the ETL 170 is not limited to that set forth herein.

The EIL 180 is disposed between the second electrode 120 and the ETL 170, and may improve a property of the second electrode 120 to elongate a lifetime of the LED 100. The EIL 180 may include an alkali halide material such as LiF, CsF, NaF and BaF$_2$ and/or an organic metal material such as LiQ (lithium quinolate), lithium benzoate and sodium stearate. However, the EIL 180 is not limited to that set forth herein.

When the hole moves to the second electrode 120 through the EML 160 or the electron moves to the first electrode 110 through the EML 160, a lifetime and an efficiency may be reduced. To prevent the reduction in the lifetime and the efficiency, the LED 100 may further include an exciton blocking layer at one of upper and lower portions of the EML 160.

For example, a hole blocking layer (HBL) of a material such that 2,9-dimethyl-4,7-diphenyl-1,10-phenanthroline (BCP) and/or bis(2-methyl-8-quinolinolato)(4-phenylphenolato)aluminum(III) (BAlq) having a relatively low highest occupied molecular orbital (HOMO) may be disposed between the EML 160 and the ETL 170 to prevent a movement of a hole, and/or an electron blocking layer (EBL) of a material such that 4,4',4"-Tris(carbazol-9-yl)-triphenylamine (TCTA) may be disposed between the EML 160 and the HTL 150 to prevent a movement of an electron.

The LED 100 according to a first embodiment of the present disclosure includes the first and second electrodes 110 and 120, and the organic material layer 130 between the first and second electrodes 110 and 120. The organic material layer 130 includes a hole layer having the HIL 140 and the HTL 150, and the EML 160. The organic compound of the chemical formulas 1 to 5 may be used as a host material for the HIL 140 and/or the HTL 150, or may be used as a dopant for the HIL 140 and/or the HTL 150. In addition, the organic compound of the chemical formulas 1 to 5 may be used as a host or a dopant for the EML 160.

In the first embodiment of the present disclosure, since the organic compound has a fused structure, the organic compound has an excellent thermal stability. Since the amine group directly or indirectly connected to the plurality of aromatic rings having a conjugated structure functions as an electron donor, the organic compound has an excellent emission property and an excellent hole transport property. Accordingly, when the organic compound is applied to the organic material layer 130, an emission efficiency, a lifetime, a color purity, a hole transport property and a hole move property of the LED 100 are improved.

Figure 2:
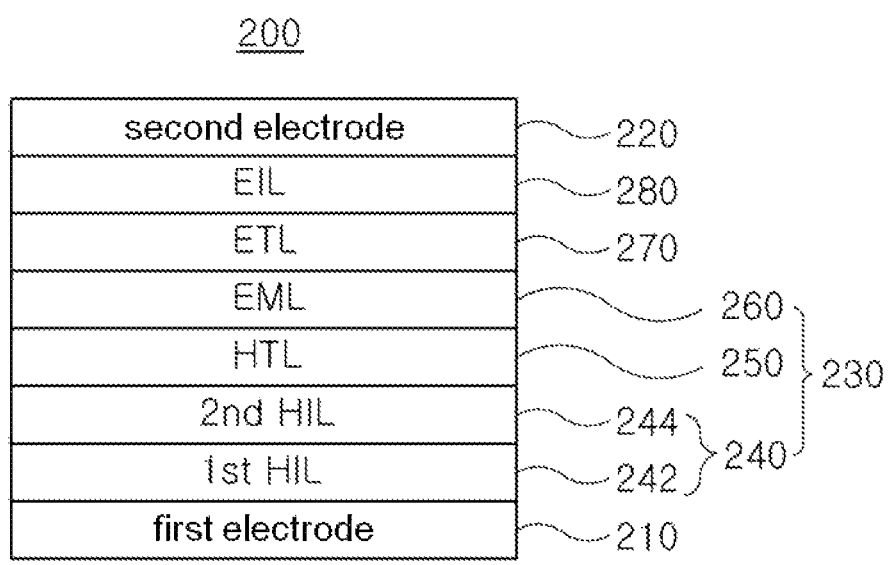
FIG. 2 is a cross-sectional view showing a light emitting diode according to a second embodiment of the present disclosure.

FIG. 2 is a cross-sectional view showing a light emitting diode according to a second embodiment of the present disclosure.

In FIG. 2, a light emitting diode (LED) 200 according to the second embodiment of the present disclosure includes first and second electrodes 210 and 220 facing each other, an organic material layer 230 between the first and second electrodes 210 and 220, and an electron transporting layer (ETL) 270 and an electron injecting layer (EIL) 280 sequentially disposed between the organic material layer 230 and the second electrode 220.

The organic material layer 230 includes a hole injecting layer (HIL) 240, a hole transporting layer (HTL) 250 and an emitting material layer (EML) 260 sequentially formed on the first electrode 210. The HIL 240 and the HTL 250 constitute a hole layer, and the HIL 240 includes first and second HILs 242 and 244.

Similarly to the first embodiment, the first electrode 210 may include a conductive material of a relatively high work function to form an anode, and the second electrode 220 may include a conductive material of a relatively low work function to form a cathode.

The HIL 240 includes the first and second HILs 242 and 244 sequentially disposed on the first electrode 210, and the first HIL 242 is disposed between the first electrode 210 and the second HIL 244.

In an exemplary embodiment, the first HIL 242 may include a hole injecting material such as MTDATA, CuPc, NPB and/or PEDOT/PSS. The second HIL 244 may include an organic compound represented by the chemical formulas 1 to 5, or may include a hole injecting host material doped with a dopant of an organic compound represented by the chemical formulas 1 to 5. When the second HIL 244 includes the hole injecting material and the dopant of the organic compound of the chemical formulas 1 to 5, the hole injecting host material may include MTDATA, CuPc, NPB and/or PEDOT/PSS and may be doped with the organic compound of the chemical formulas 1 to 5 by about 0.1 wt % to about 50 wt %. However, the first and second HILs 242 and 244 are not limited to that set forth herein.

In another exemplary embodiment, the first HIL 242 may include an organic compound represented by the chemical formulas 1 to 5, or may include a hole injecting host material doped with a dopant of an organic compound represented by the chemical formulas 1 to 5. The second hole injecting layer 244 may include a hole injecting material such as MTDATA, CuPc, NPB and/or PEDOT/PSS.

The HTL 250 is disposed between the first electrode 210 and the EML 260 to be adjacent to the EML 260. The HTL 250 may include an organic compound represented by the chemical formulas 1 to 5, or a hole transporting host material doped with an organic compound represented by the chemical formulas 1 to 5.

When the HTL 250 includes the hole transporting host material and the organic compound represented by the chemical formulas 1 to 5, the hole transporting host material may be TPD and/or NPB, and may be doped with the organic compound of the chemical formulas 1 to 5 by about 0.1 wt % to about 50 wt %. However, the HTL 250 is not limited to that set forth herein.

An organic compound of the chemical formulas 1 to 5 may be used as a host or a dopant of the EML 260. Materials of the host and the dopant used with the organic compound of the chemical formulas 1 to 5 for the EML 260 are the same as those of the first embodiment.

The ETL 270 may include an electron transport material such as oxadiazole, triazole, phenanthroline, benzoxazole, benzthiazole and/or benzimidazole (for example, 2-[4-(9, 10-Di-2-naphthalenyl-2-anthracenyl)phenyl]-1-phenyl-1H-benzimidazole). The EIL 280 may include an alkali halide material such as LiF, CsF, NaF and $BaF_2$ and/or an organic metal material such as LiQ (lithium quinolate), lithium benzoate and sodium stearate.

The LED 200 may further include an exciton blocking layer having at least one of a hole blocking layer (HBL) between the EML 260 and the ETL 270 for preventing a movement of a hole and an electron blocking layer (EBL) between the EML 260 and the HTL 250 for preventing a movement of an electron.

In the LED 200 according to the second embodiment of the present disclosure as compared with the LED 100 according to the first embodiment of the present disclosure, the HIL 240 may have a double layered structure including a first layer having only a hole injecting material and a second layer having only an organic compound of the chemical formulas 1 to 5 or a hole injecting material doped with an organic compound of the chemical formulas 1 to 5.

In the LED 200 according to the second embodiment of the present disclosure, the organic material layer 230 includes the hole layer having the HIL 240 and the HTL 250 and the EML 260, and the HIL 240 includes the first and second HILs 242 and 244. The organic compound of the chemical formulas 1 to 5 may be used as a host material for one of the first and second HILs 242 and 244 constituting the HIL 240 and/or the HTL 250, or may be used as a dopant for the HIL 240 and/or the HTL 250. In addition, the organic compound of the chemical formulas 1 to 5 may be used as a host or a dopant for the EML 260.

In the second embodiment of the present disclosure, since the organic compound has a fused structure, the organic compound has an excellent thermal stability. Since the amine group directly or indirectly connected to the plurality of aromatic rings having a conjugated structure functions as an electron donor, the organic compound has an excellent emission property and an excellent hole transport property. Accordingly, when the organic compound is applied to the organic material layer 230, an emission efficiency, a lifetime, a color purity and a hole transport property of the LED 200 are improved.

Figure 3:
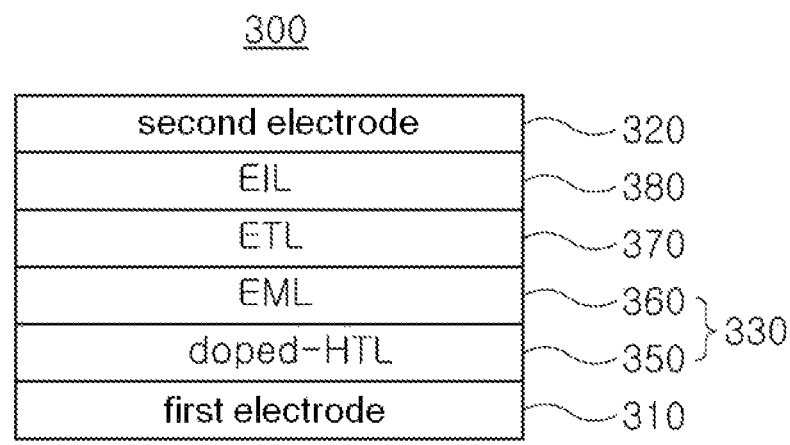
FIG. 3 is a cross-sectional view showing a light emitting diode according to a third embodiment of the present disclosure.

FIG. 3 is a cross-sectional view showing a light emitting diode according to a third embodiment of the present disclosure.

In FIG. 3, a light emitting diode (LED) 300 according to the third embodiment of the present disclosure includes first and second electrodes 310 and 320 facing each other, an organic material layer 330 between the first and second electrodes 310 and 320, and an electron transporting layer (ETL) 370 and an electron injecting layer (EIL) 380 sequentially disposed between the organic material layer 330 and the second electrode 320.

The organic material layer 330 includes a doped hole transporting layer (HTL) 350 and an emitting material layer (EML) 360 sequentially formed on the first electrode 310. The doped HTL 350 constitutes a hole layer.

Similarly to the first embodiment, the first electrode 310 may include a conductive material of a relatively high work function to form an anode, and the second electrode 320 may include a conductive material of a relatively low work function to form a cathode.

The HTL 350 may include a hole transporting host material doped with an organic compound represented by the chemical formulas 1 to 5. For example, the hole transporting host material may be TPD and/or NPB, and may be doped with the organic compound of the chemical formulas 1 to 5 by about 0.1 wt % to about 50 wt %. However, the HTL 350 is not limited to that set forth herein.

An organic compound of the chemical formulas 1 to 5 may be used as a host or a dopant of the EML 360. Materials of the host and the dopant used with the organic compound of the chemical formulas 1 to 5 for the EML 360 are the same as those of the first embodiment.

The ETL 370 may include an electron transport material such as oxadiazole, triazole, phenanthroline, benzoxazole, benzthiazole and/or benzimidazole (for example, 2-[4-(9, 10-Di-2-naphthalenyl-2-anthracenyl)phenyl]-1-phenyl-1H-benzimidazole). The EIL 380 may include an alkali halide material such as LiF, CsF, NaF and $BaF_2$ and/or an organic metal material such as LiQ (lithium quinolate), lithium benzoate and sodium stearate.

The LED 300 may further include an exciton blocking layer having at least one of a hole blocking layer (HBL) between the EML 360 and the ETL 370 for preventing a movement of a hole and an electron blocking layer (EBL) between the EML 360 and the HTL 350 for preventing a movement of an electron.

In the LED 300 according to the third embodiment of the present disclosure as compared with the LED 100 according to the first embodiment of the present disclosure, the hole layer of the organic material layer 330 includes the doped HTL 350 between the first electrode 310 and the EML 360.

In the LED 300 according to the third embodiment of the present disclosure, the organic material layer 330 includes the hole layer having a single layered structure of the doped HTL 350 and the EML 360. The organic compound of the chemical formulas 1 to 5 may be used as a dopant for the doped HTL 350. In addition, the organic compound of the chemical formulas 1 to 5 may be used as a host or a dopant for the EML 360.

In the third embodiment of the present disclosure, since the organic compound has a fused structure, the organic compound has an excellent thermal stability. Accordingly, when the organic compound is applied to the organic material layer 330, an emission efficiency, a lifetime, a color purity and a hole transport property of the LED 300 are improved. Since the amine group directly or indirectly connected to the plurality of aromatic rings having a conjugated structure functions as an electron donor, the organic compound has an excellent emission property and an excellent hole transport property.

Specifically, since the organic compound has an excellent hole transport property, the doped HTL 350 including the hole transport host material doped with the organic compound of the chemical formulas 1 to 5 may function as both of the HIL and the HTL. In the LED 300 according to the third embodiment of the present disclosure, a surface of the doped HTL 350 is disposed to contact the first electrode 310 and an opposite surface of the doped HTL 350 is disposed to contact the EML 360. As a result, an excellent hole injection property and an excellent hole transport property are obtained even when only the HTL 350 doped with the organic compound of the chemical formulas 1 to 5 is disposed between first electrode 310 and the EML 360.

Figure 4:
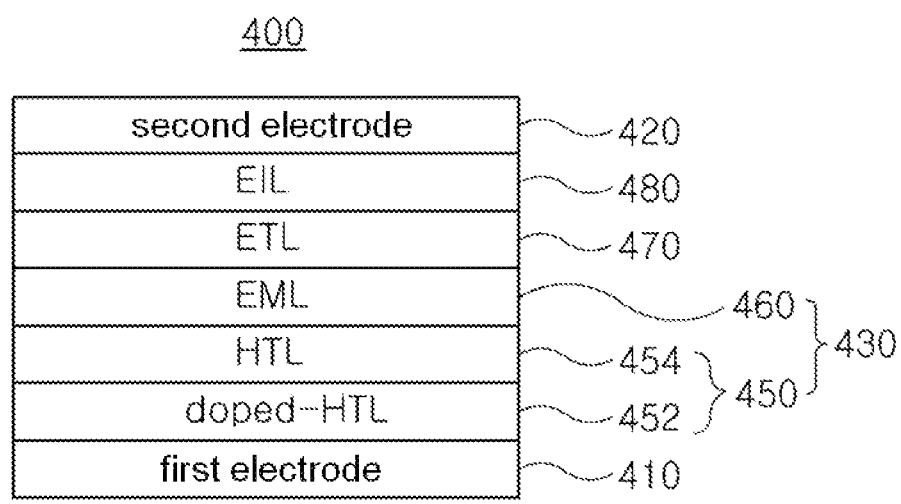
FIG. 4 is a cross-sectional view showing a light emitting diode according to a fourth embodiment of the present disclosure.

FIG. 4 is a cross-sectional view showing a light emitting diode according to a fourth embodiment of the present disclosure.

In FIG. 4, a light emitting diode (LED) 400 according to the fourth embodiment of the present disclosure includes first and second electrodes 410 and 420 facing each other, an organic material layer 430 between the first and second electrodes 410 and 420, and an electron transporting layer (ETL) 470 and an electron injecting layer (EIL) 480 sequentially disposed between the organic material layer 430 and the second electrode 420.

The organic material layer 430 includes a hole transporting layer (HTL) 450 and an emitting material layer (EML) 460 sequentially formed on the first electrode 410. The HTL 450 constitutes a hole layer, and includes first and second HTLs 452 and 454.

Similarly to the first embodiment, the first electrode 410 may include a conductive material of a relatively high work function to form an anode, and the second electrode 420 may include a conductive material of a relatively low work function to form a cathode.

The HTL 450 may include the first HTL 452 of a doped HTL and the second HTL 454. The first HTL 452 of a doped HTL is disposed between the first electrode 410 and the second HTL 454.

In an exemplary embodiment, the first HTL 452 of a doped HTL includes a hole transporting host material such as TPD and/or NPB doped with the organic compound of the chemical formulas 1 to 5 by about 0.1 wt % to about 50 wt %. The second HTL 454 includes only a hole transport material such as TPD and/or NPB.

In the LED 400 according to the fourth embodiment of the present disclosure as compared with the LED 300 of FIG. 3, the second HTL 454 of a hole transport material is disposed between the first HTL 452 of a doped HTL and the EML 460.

An organic compound of the chemical formulas 1 to 5 may be used as a host or a dopant of the EML 460. Materials of the host and the dopant used with the organic compound of the chemical formulas 1 to 5 for the EML 460 are the same as those of the first embodiment.

The ETL 470 may include an electron transport material such as oxadiazole, triazole, phenanthroline, benzoxazole, benzthiazole and/or benzimidazole (for example, 2-[4-(9, 10-Di-2-naphthalenyl-2-anthracenyl)phenyl]-1-phenyl-1H-benzimidazole). The EIL 480 may include an alkali halide material such as LiF, CsF, NaF and $BaF_2$ and/or an organic metal material such as LiQ (lithium quinolate), lithium benzoate and sodium stearate.

The LED 400 may further include an exciton blocking layer having at least one of a hole blocking layer (HBL) between the EML 460 and the ETL 470 for preventing a movement of a hole and an electron blocking layer (EBL) between the EML 460 and the HTL 450 for preventing a movement of an electron.

In the LED 400 according to the fourth embodiment of the present disclosure as compared with the LED 300 according to the third embodiment of the present disclosure, the HTL 450 constituting the hole layer includes the first HTL 452 and the second HTL 454 of a hole transport material between the first HTL 452 and the EML 460.

In the fourth embodiment of the present disclosure, since the organic compound has a fused structure, the organic compound has an excellent thermal stability. Accordingly, when the organic compound is applied to the organic material layer 430, an emission efficiency, a lifetime, a color purity and a hole transport property of the LED 400 are improved. Since the amine group directly or indirectly connected to the plurality of aromatic rings having a conjugated structure functions as an electron donor, the organic compound has an excellent emission property and an excellent hole transport property.

Specifically, since the organic compound has an excellent hole transport property, the first HTL 452 including the hole transport host material doped with the organic compound of the chemical formulas 1 to 5 may function as both of the HIL and the HTL. In addition, since the HTL 450 further include the second HTL 454 of the hole transport material between the first HTL 452 and the EML 460.

Figure 5:
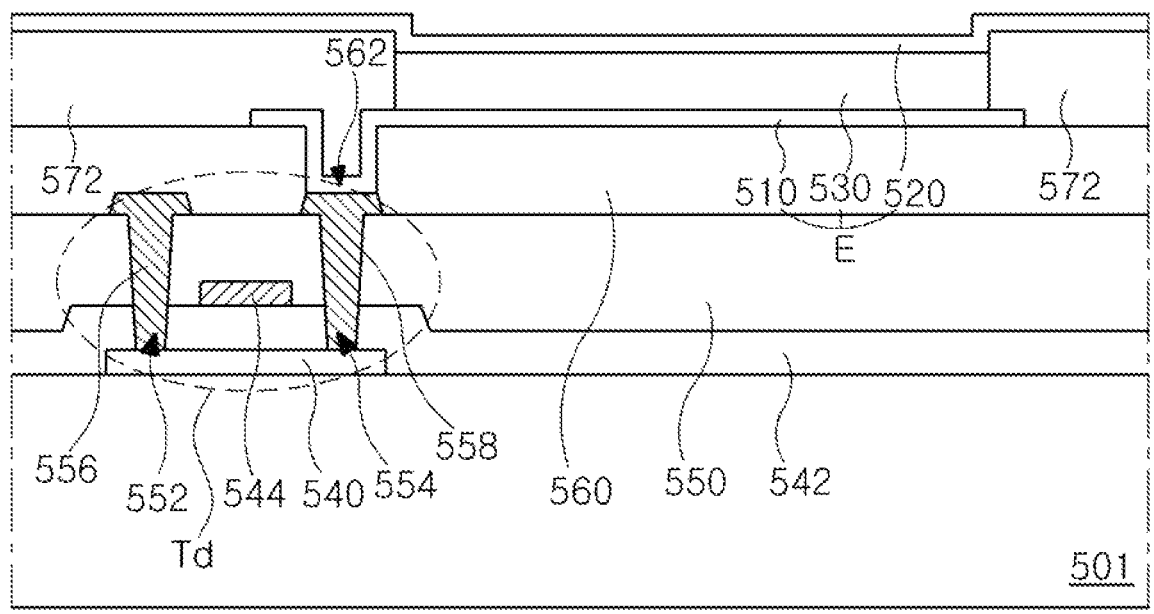
FIG. 5 is a cross-sectional view showing an organic light emitting diode display device according to a fifth embodiment of the present disclosure.

FIG. 5 is a cross-sectional view showing an organic light emitting diode display device according to a fifth embodiment of the present disclosure.

In FIG. 5, an organic light emitting diode (OLED) display device 500 includes a driving thin film transistor (TFT) Td, a planarizing layer 560 covering the driving TFT Td and a light emitting diode (LED) E on the planarizing layer 560 and connected to the driving TFT Td. The driving TFT Td includes a semiconductor layer 540, a gate electrode 544, a source electrode 556 and a drain electrode 558. The driving TFT Td of FIG. 5 has a coplanar structure.

A first substrate 501 of a base substrate includes a glass or a plastic, and the semiconductor layer 540 is formed on the first substrate 501. For example, the semiconductor layer 540 may include an oxide semiconductor material or polycrystalline silicon. When the semiconductor layer 540 includes an oxide semiconductor material, a light shielding pattern and a buffer layer may be formed under the semiconductor layer 540. The light shielding pattern may block a light incident to the semiconductor layer 540 to prevent deterioration of the semiconductor layer 540 due to the light. When the semiconductor layer 540 includes polycrystalline silicon, both end portions of the semiconductor layer 540 may be doped with an impurity material.

A gate insulating layer 542 of an insulating material is formed on an entire surface of the first substrate 501 having the semiconductor layer 540. The gate insulating layer 542 may include an inorganic insulating material such as silicon oxide or silicon nitride.

A gate electrode 544 of a conductive material such as a metal is formed on the gate insulating layer 542 to correspond to a central portion of the semiconductor layer 540. A gate line and a first capacitor electrode are formed on the gate insulating layer 542. The gate line may be disposed along a first direction, and the first capacitor electrode may be connected to the gate electrode 544. Although the gate insulating layer 542 is formed on the entire surface of the first substrate 501 in the fifth embodiment, the gate insulating layer 542 may have the same shape as the gate electrode 544 by patterning in another embodiment.

An interlayer insulating layer 550 of an insulating material is formed on an entire surface of the first substrate 501 having the gate electrode 544. The interlayer insulating layer 550 may include one of an inorganic insulating material such as silicon oxide or silicon nitride and an organic insulating material such as benzocyclobutene (BCB) and photo acryl.

The interlayer insulating layer 550 and the gate insulating layer 542 have first and second contact holes 552 and 554 exposing the both end portions, respectively, of the semiconductor layer 540. The first and second contact holes 552 and 554 are disposed at a side of the gate electrode 544 to be spaced apart from the gate electrode 544. When the gate insulating layer 542 has the same shape as the gate electrode 544, the first and second contact holes 552 and 554 may be formed only in the interlayer insulating layer 550.

The source electrode 556 and the drain electrode 558 of a conductive material such as a metal are formed on the interlayer insulating layer 550. In addition, a data line along a second direction, a power line and a second capacitor electrode are formed on the interlayer insulating layer 550.

The source electrode 556 and the drain electrode 558 are spaced apart from each other with the gate electrode 544 at a center thereof. The source electrode 556 and the drain electrode 558 contact the both end portions of the semiconductor layer 540 through the first and second contact holes 552 and 554, respectively. The data line crosses the gate line to define a pixel region, and the power line supplying a high level voltage is spaced apart from the data line. The second capacitor electrode is connected to the drain electrode 558 and overlaps the first capacitor electrode. The first and second capacitor electrodes and the interlayer insulating layer 550 between the first and second capacitor electrodes constitute a storage capacitor.

The semiconductor layer 540, the gate electrode 544, the source electrode 556 and the drain electrode 558 constitute the driving TFT Td. The driving TFT Td of FIG. 5 has a coplanar structure where the gate electrode 544 is disposed at the same position as the source electrode 556 and the drain electrode 558 with respect to an interface between the gate electrode 544 and the gate insulating layer 542.

In another embodiment, the driving TFT Td may have an inverted staggered structure where the gate electrode 544 is disposed at the opposite position to the source electrode 556 and the drain electrode 558 with respect to an interface between the gate electrode 544 and the gate insulating layer 542, and the semiconductor layer 540 may include amorphous silicon.

A switching TFT having substantially the same structure as the driving TFT Td is further formed on the first substrate 501. The gate electrode 544 of the driving TFT Td is connected to the drain electrode of the switching TFT and the source electrode 556 of the driving TFT Td is connected to the power line. In addition, the gate electrode and the source electrode of the switching TFT are connected to the gate line and the data line, respectively.

The planarizing layer 560 is formed on an entire surface of the first substrate 501 having the source electrode 556 and the drain electrode 558 and has a drain contact hole 562 exposing the drain electrode 558 of the driving TFT Td. Although the drain contact hole 562 is disposed directly over the second contact hole 554 in FIG. 5, the drain contact hole 562 may be spaced apart from the second contact hole 554 in another embodiment.

The LED E is disposed on the planarizing layer 560 and includes a first electrode 510, an emitting layer 530 and a second electrode 520. The first electrode 510 is connected to the drain electrode 558 of the driving TFT Td, and the emitting layer 530 and the second electrode 520 are sequentially formed on the first electrode 510. The first electrode 510 may include a conductive material of a relatively high work function to form an anode, and the second electrode 520 may include a conductive material of a relatively low work function to form a cathode.

A second substrate of an encapsulating substrate covering the LED E may be attached to the first substrate 501. A barrier layer may be formed between the LED E and the second substrate to attach the first and second substrates and to prevent penetration of a moisture and oxygen into the LED E.

As in the first to fourth embodiments of FIGS. 1 to 4, the emitting layer 530 may have an organic material layer including a hole layer and an emitting material layer (EML).

The hole layer may include only an organic compound of the chemical formulas 1 to 5 or a host material doped with an organic compound of the chemical formulas 1 to 5. In the EML, the organic compound of the chemical formulas 1 to 5 may be used as a host or a dopant. The emitting layer 530 may further include an electron injecting layer (EIL) and an electron transporting layer (ETL), and may selectively further include a hole blocking layer (HBL) and an electron blocking layer (EBL).

In the fifth embodiment of the present disclosure, since the organic compound has a fused structure, the organic compound has an excellent thermal stability. Accordingly, when the organic compound is applied to the organic material layer 530, an emission efficiency, a lifetime, a color purity and a hole transport property of the LED E are improved. Since the amine group directly or indirectly connected to the plurality of aromatic rings having a conjugated structure functions as an electron donor, the organic compound has an excellent emission property and an excellent hole transport property.

Synthesis Example 1: Synthesis of Compound A1

1) Fabrication of Intermediate A1-a

[Reaction Formula 1-1]

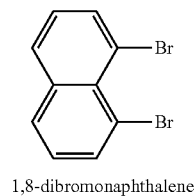

1,8-dibromonaphthalene

+

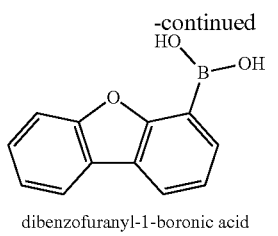

dibenzofuranyl-1-boronic acid $\xrightarrow{\text{Pd(PPh3)4, K2CO3, THF/water}}$

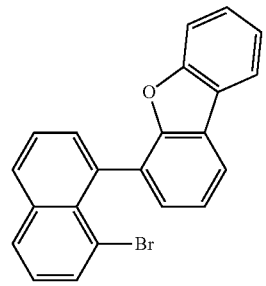

A1-a

After a mixture was formed by dissolving 1,8-dibromonaphthalene (35.0 mmol), dibenzofuranyl-1-boronic acid (35.0 mmol), tetrakis(triphenylphosphine)palladium(0) (1.5 mmol) in THF 150 mL of 250 mL 2-neck flask under a nitrogen atmosphere, the mixture was stirred in a bath of 70° C. for 24 hours. After a reaction was finished, THF was removed from the mixture. After the mixture was extracted using dichloromethane and a water, a silica gel column process was performed. After distillation under reduced pressure was performed for a solvent, the mixture was re-crystallized using dichloromethane and hexane to obtain a solid compound A1-a of 10.4 g (85%).

2) Fabrication of Intermediate A1-b

[Reaction Formula 1-2]

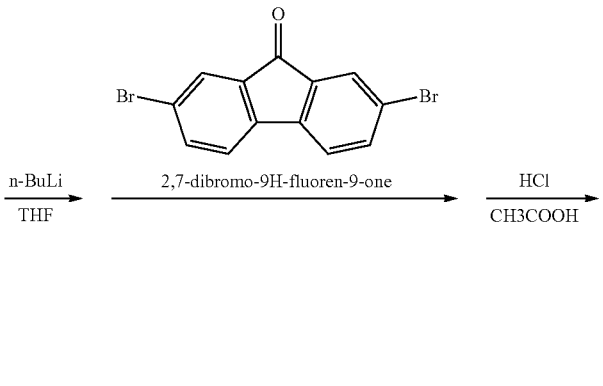

A1-a $\xrightarrow[\text{THF}]{\text{n-BuLi}}$ 2,7-dibromo-9H-fluoren-9-one $\xrightarrow[\text{CH3COOH}]{\text{HCl}}$

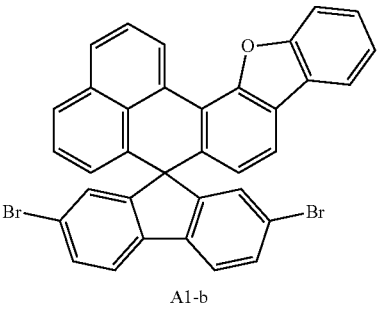

A1-b

After a mixture was formed by dissolving the compound A1-a in THF (100 mL) of 250 mL 2-neck flask under a nitrogen atmosphere, a temperature was reduced to −78° C. After n-BuLi (2.5M in n-hexane, 11.2 mL) was slowly dropped, the mixture was stirred for 1 hour. After 2,7-dibromo-9H-fluoren-9-one (28.0 mmol) melted in THF 30 mL was slowly dropped, the mixture was stirred. After the temperature was slowly increased to a room temperature, the mixture was stirred for 12 hours. After a reaction was finished by adding saturated NaHCO$_3$ (100 mL) aqueous solution, the mixture was extracted using dichloromethane and a water. After distillation under reduced pressure was performed, a compound was gathered. After the compound was dissolved in acetic acid (50 mL) of 250 mL 2-neck flask, a small amount of 3N HCl was added and the mixture was stirred at 100° C. for 12 hours. After the mixture was cooled down to a room temperature, the mixture was filtered and silica gel column process was performed for a precipitate. After distillation under reduced pressure was performed for a solvent, the mixture was re-crystallized using dichloromethane and hexane to obtain a solid compound A1-b of 12.9 g (75%).

3) Fabrication of Compound A1

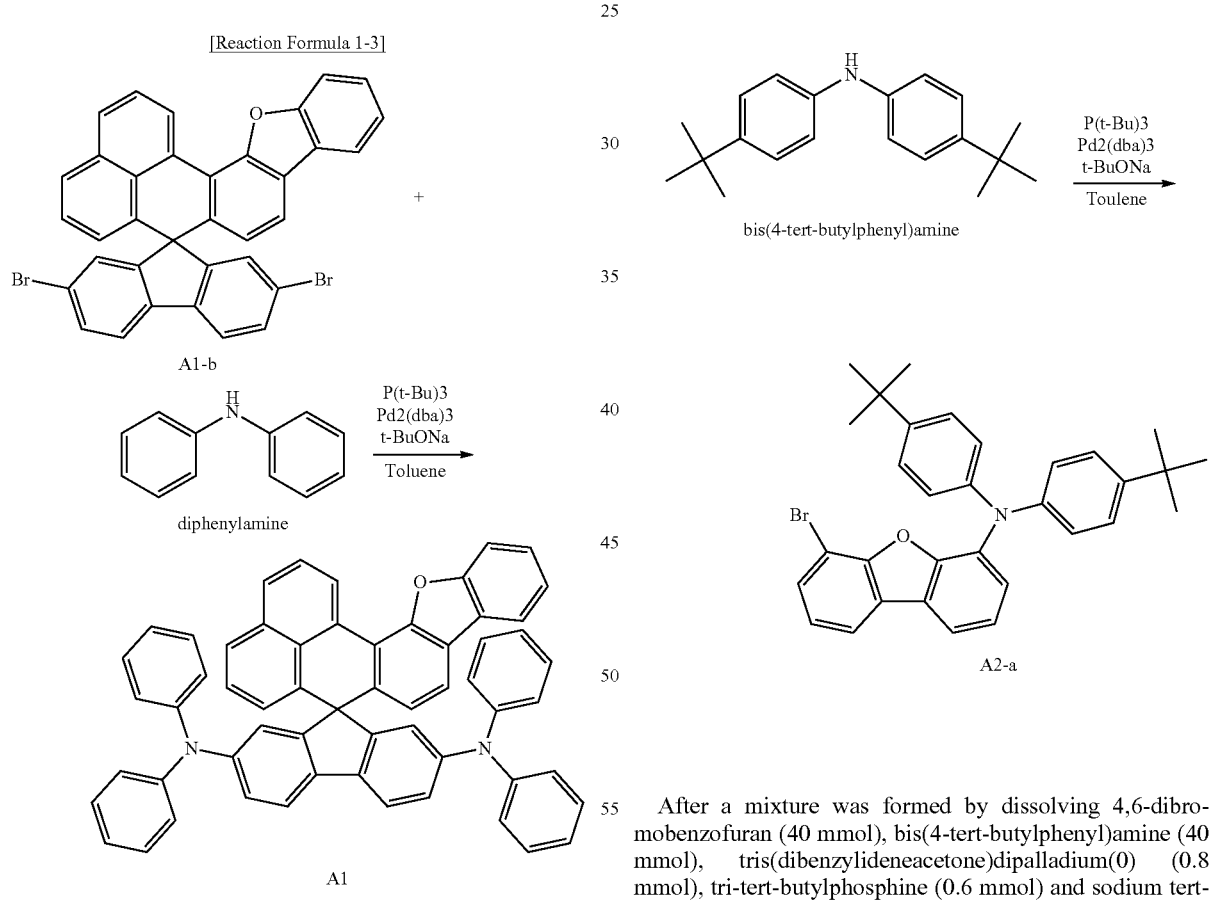

A1

After a mixture was formed by dissolving the compound A1-b (21.0 mmol), diphenylamine (50 mmol), tris(dibenzylideneacetone)dipalladium(0) (1 mmol), tri-tert-butylphosphine (0.7 mmol) and sodium tert-butoxide (70 mmol) in toluene (70 mL) of 250 mL 2-neck flask under a nitrogen atmosphere, the mixture was stirred in a bath of 100° C. for 24 hours. After a reaction was finished, toluene was removed from the mixture. After the mixture was extracted using dichloromethane and a water, a silica gel column process was performed and then distillation under reduced pressure was performed for a solvent. After the mixture was re-crystallized using dichloromethane and acetone and filtered, thermal refining was performed to obtain a compound A1 of 13.8 g (83%).

Synthesis Example 2: Synthesis of Compound A2

1) Fabrication of Intermediate A2-a

[Reaction Formula 2-1]

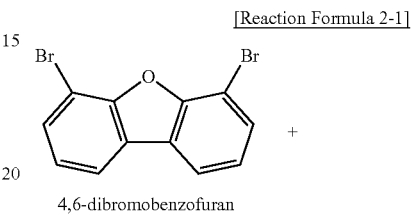

4,6-dibromobenzofuran

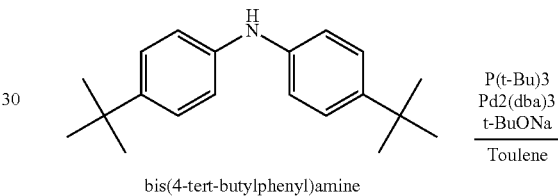

A2-a

After a mixture was formed by dissolving 4,6-dibromobenzofuran (40 mmol), bis(4-tert-butylphenyl)amine (40 mmol), tris(dibenzylideneacetone)dipalladium(0) (0.8 mmol), tri-tert-butylphosphine (0.6 mmol) and sodium tert-butoxide (52 mmol) in toluene (150 mL) of 250 mL 2-neck flask under a nitrogen atmosphere, the mixture was stirred in a bath of 70° C. for 24 hours. After a reaction was finished, toluene was removed from the mixture. After the mixture was extracted using dichloromethane and water, a silica gel column process was performed. After distillation under reduced pressure was performed for a solvent, the mixture was re-crystallized using dichloromethane and hexane to obtain a compound A2-a of 17.9 g (85%).

2) Fabrication of Intermediate A2-b

[Reaction Formula 2-2]

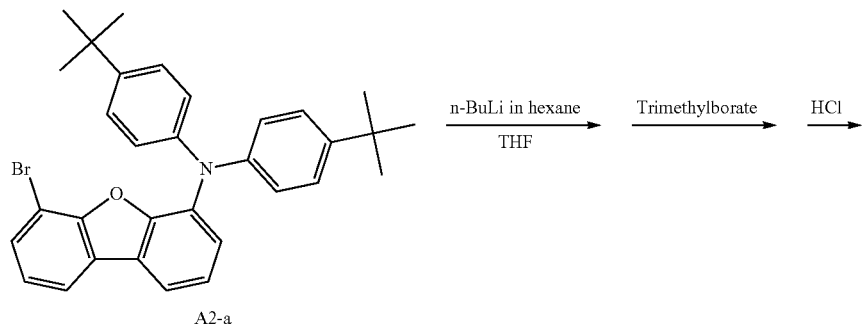

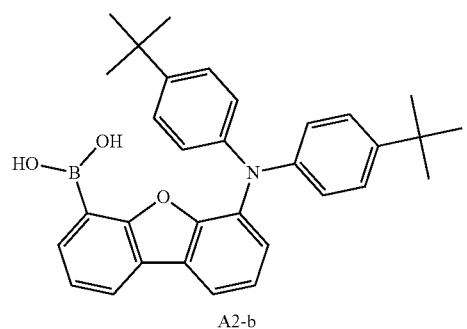

After a mixture was formed by dissolving the compound A2-a in THF (100 mL) of 250 mL 2-neck flask under a nitrogen atmosphere, a temperature was reduced to −75° C. and the mixture was stirred. After n-BuLi (2.5M in n-hexane, 13.6 mL) was dropped, the temperature was increased to 0° C. and the mixture was stirred for 30 minutes. After the temperature was reduced to −75° C. again, trimethyl borate (37 mmol) was slowly dropped. After the temperature was slowly increased to a room temperature, the mixture was stirred for 3 hours. After the mixture had acidity by adding 3N HCl, the mixture was extracted using ethyl acetate and a water. After distillation under reduced pressure was performed for a solvent of an organic layer, the mixture was re-crystallized using toluene to obtain a compound A2-b of 13 g (78%).

3) Fabrication of Intermediate A2-c

[Reaction Formula 2-3]

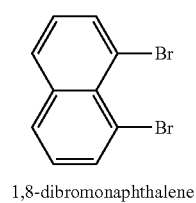

1,8-dibromonaphthalene

+

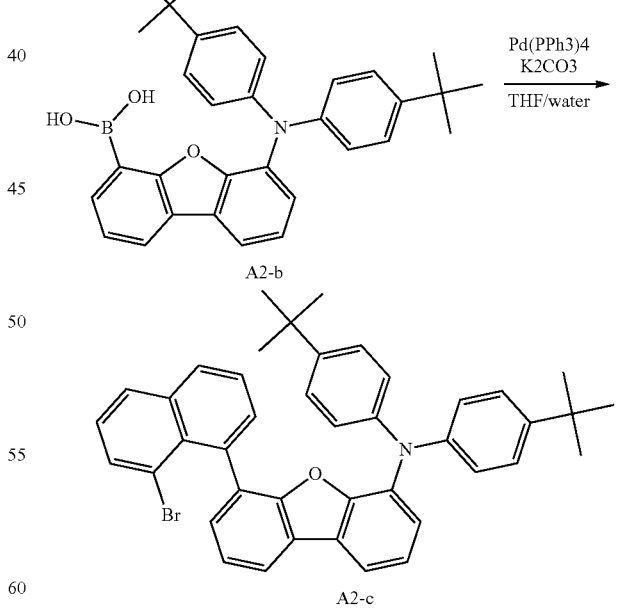

After a mixture was formed by dissolving 1,8-dibromonaphthalene (26 mmol), the compound A2-b (26 mmol), tetrakis(triphenylphosphine)palladium(0) (1.3 mmol) and K₂CO₃ 15 g in THF (120 mL) and a distilled water of 250 mL 2-neck flask under a nitrogen atmosphere, the mixture was stirred in a bath of 70° C. for 24 hours. After a reaction was finished, THF was removed from the mixture. After the mixture was extracted using dichloromethane and a water, a silica gel column process was performed. After distillation under reduced pressure was performed for a solvent, the mixture was re-crystallized using dichloromethane and hexane and filtered to obtain a solid compound A2-c of 11.8 g (70%).

4) Fabrication of A2

[Reaction Formula 2-4]

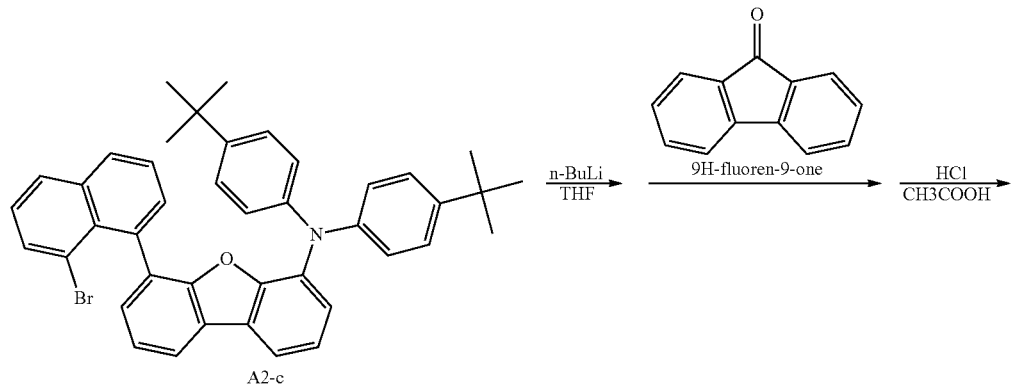

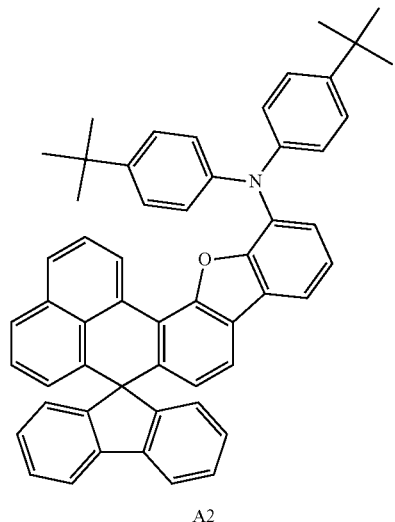

Through a method the same as the fabrication method of the compound A1-b of the synthesis example 1, the compound A2 of 9.2 g (69%) was obtained by reacting the compound A2-c (18 mmol), n-BuLi (2.5M in n-hexane, 7.2 mL) and 9H-fluoren-9-one (18 mmol).

Synthesis Example 3: Synthesis of Compound A3

1) Fabrication of Intermediate A3-a

[Reaction Formula 3-1]

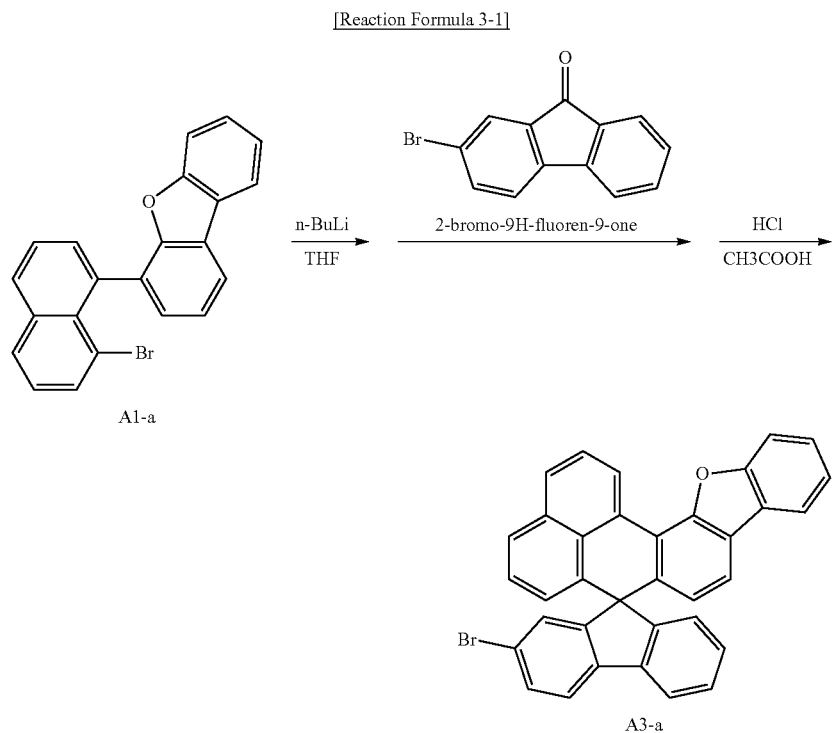

Through a method the same as the fabrication method of the compound A1-b of the synthesis example 1, the compound A3-a of 12 g (70%) was obtained by reacting the compound A1-a (32.2 mmol), n-BuLi (2.5M in n-hexane, 12.86 mL) and 2-bromo-9H-fluoren-9-one (32.2 mmol).

2) Fabrication of A3

[Reaction Formula 3-2]

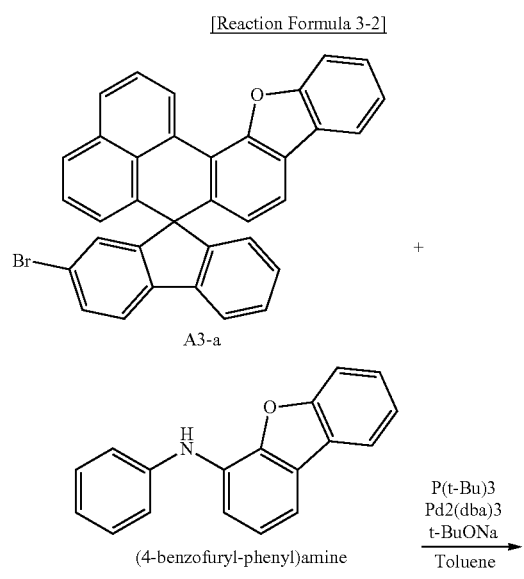

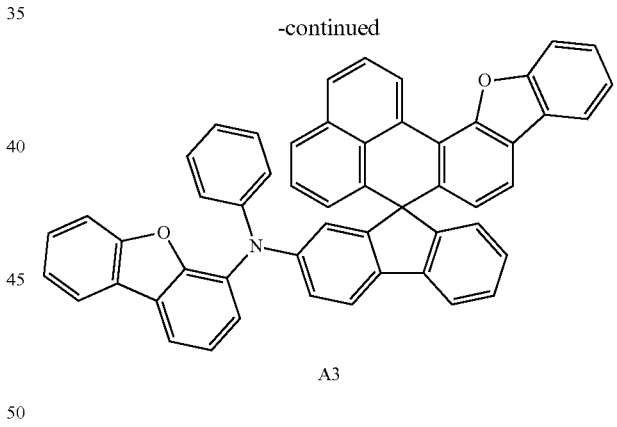

After a mixture was formed by dissolving the compound A3-b (22.4 mmol), (4-benzofuryl-phenyl)amine (18 mmol), tris(dibenzylideneacetone)dipalladium(0) (0.45 mmol), tri-tert-butylphosphine (0.33 mmol) and sodium tert-butoxide (34 mmol) in toluene (100 mL) of 250 mL 2-neck flask under a nitrogen atmosphere, the mixture was stirred in a bath of 100° C. for 24 hours. After a reaction was finished, toluene was removed from the mixture. After the mixture was extracted using dichloromethane and a water, a silica gel column process was performed and then distillation under reduced pressure was performed for a solvent. After the mixture was re-crystallized using dichloromethane and hexane and filtered to obtain a compound A3 of 10.3 g (73%).

Synthesis Example 4: Synthesis of Compound A4

1) Fabrication of Intermediate A4-a

[Reaction Formula 4-1]

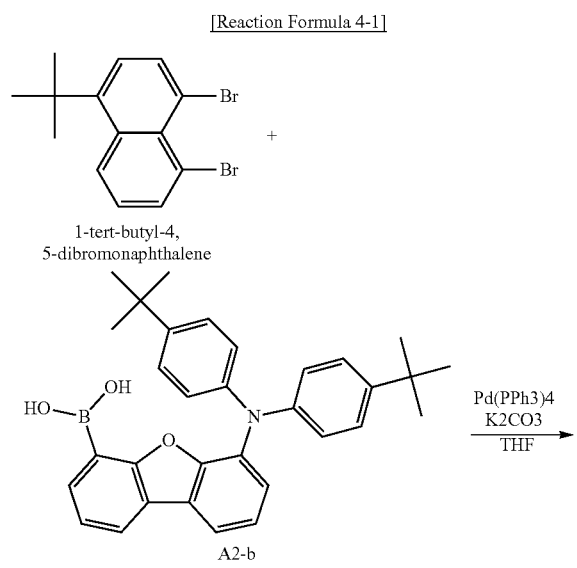

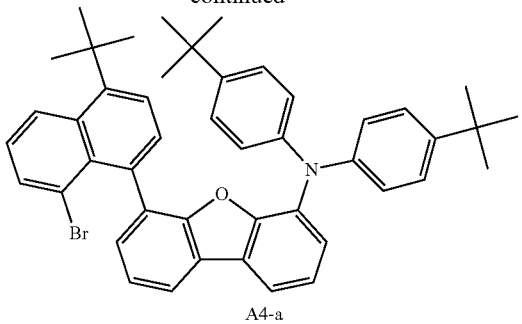

Through a method the same as the fabrication method of the compound A2-c of the synthesis example 2, the compound A4-a of 17 g (68%) was obtained by reacting 1-tert-butyl-4,5-dibromonaphthalene (35 mmol), the compound A2-b (35 mmol), tetrakis(triphenylphosphine)palladium(0) (1.75 mmol) and $K_2CO_3$ 20 g.

2) Fabrication of A4

[Reaction Formula 4-2]

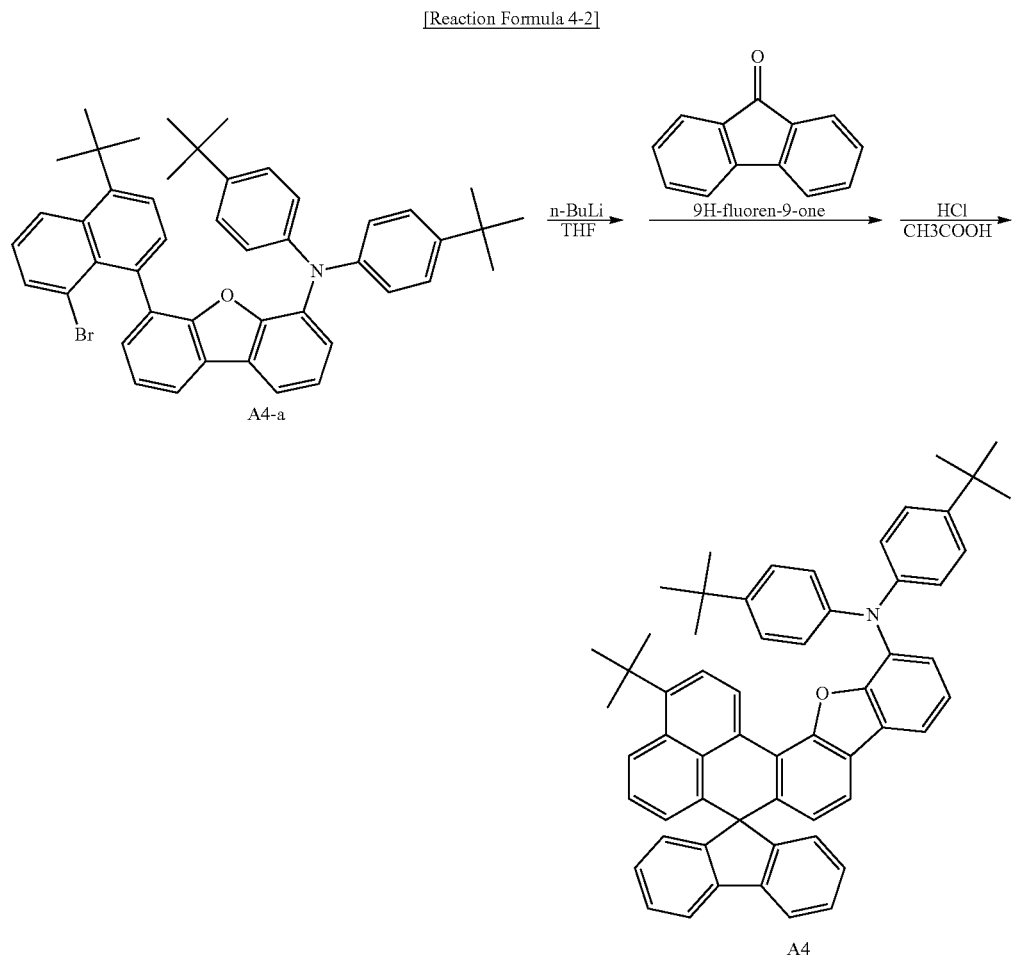

Through a method the same as the fabrication method of the intermediate compound A1-b of the synthesis example 1, the compound A4 of 10.7 g (56%) was obtained by reacting the compound A4-a (24 mmol), n-BuLi (2.5M in n-hexane, 9.6 mL) and 9H-fluoren-9-one (24 mmol).

Synthesis Example 5: Synthesis of Compound A5

1) Fabrication of Intermediate A5-a

[Reaction Formula 5-1]

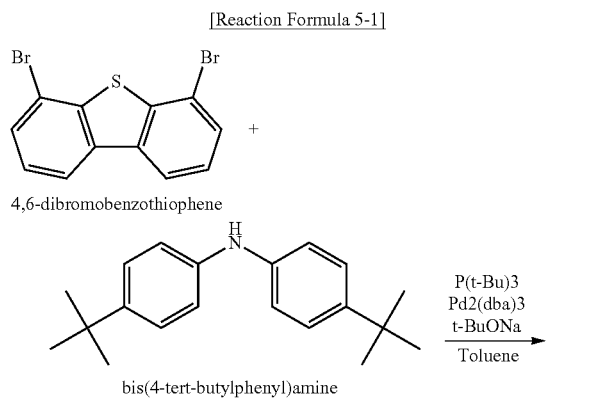

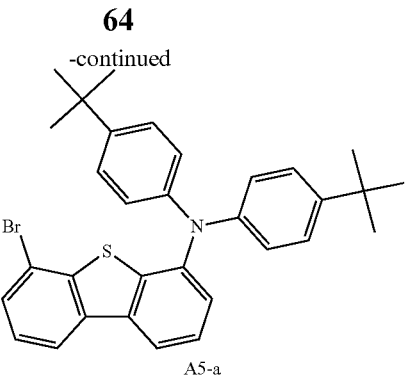

Through a method the same as the fabrication method of the intermediate compound A2-a of the synthesis example 2, the compound A5-a of 7.9 g (52%) was obtained by reacting 4,6-dibromobenzothiophene (28 mmol), bis(4-tert-butylphenyl)amine (28 mmol), tris(dibenzylideneacetone)dipalladium(0) (0.56 mmol), tri-tert-butylphosphine (0.42 mmol) and sodium tert-butoxide (36.4 mmol).

2) Fabrication of Intermediate A5-b

[Reaction Formula 5-2]

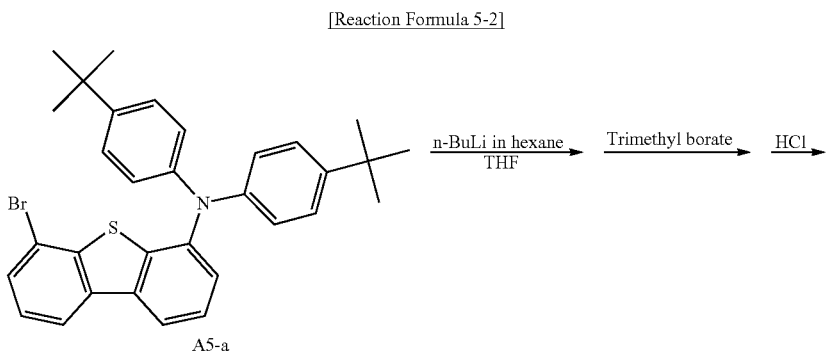

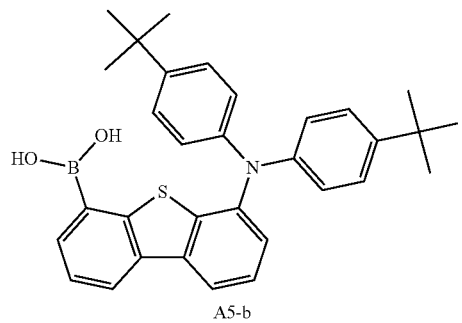

Through a method the same as the fabrication method of the intermediate compound A2-b of the synthesis example 2, the compound A5-b of 5.1 g (69%) was obtained by reacting the compound A5-a (14.6 mmol), n-BuLi (2.5M in n-hexane, 5.82 mL), trimethyl borate (16 mmol) and 3N HCl.

3) Fabrication of Intermediate A5-c

[Reaction Formula 5-3]

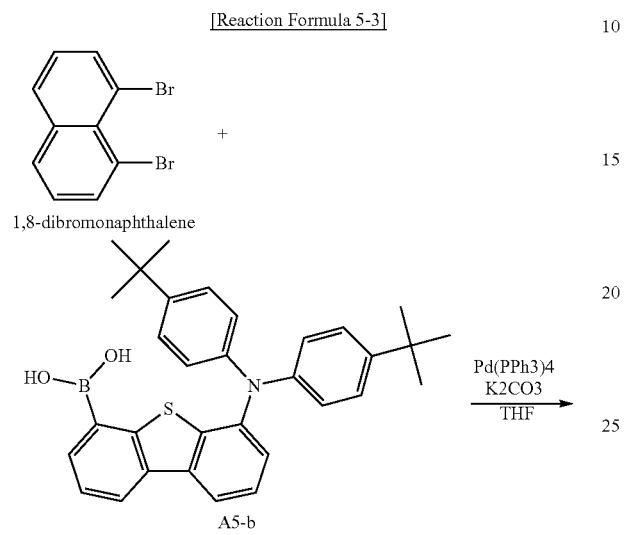

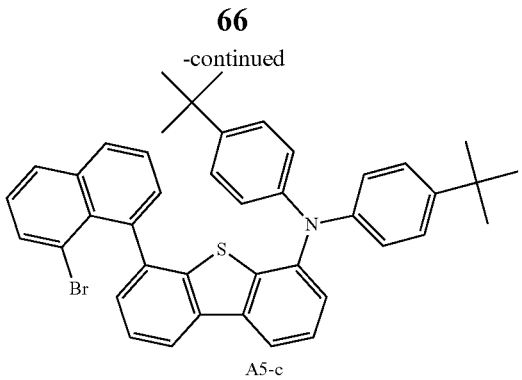

Through a method the same as the fabrication method of the intermediate compound A2-c of the synthesis example 2, the compound A5-c of 3.6 g (54%) was obtained by reacting 1,8-dibromonaphthalene (10 mmol), the compound A5-b (10 mmol), tetrakis(triphenylphosphine)palladium(0) (0.5 mmol) and $K_2CO_3$ 15 g.

4) Fabrication of A5

[Reaction Formula 5-4]

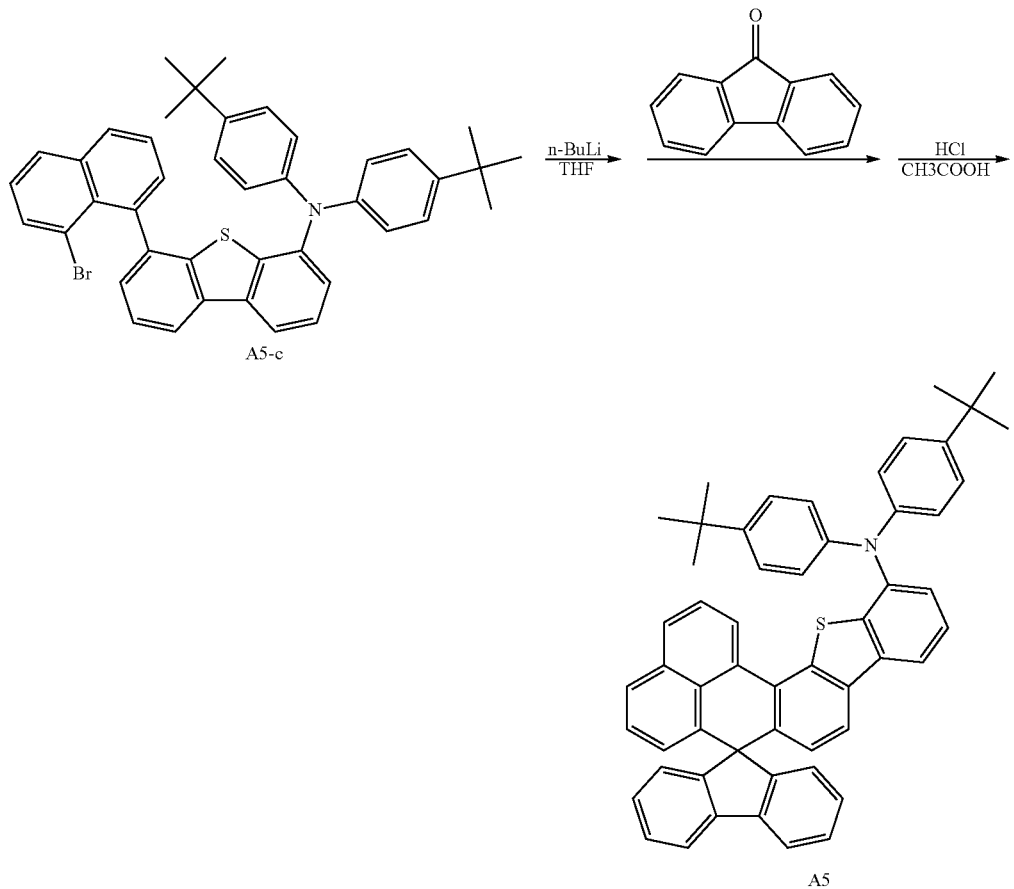

Through a method the same as the fabrication method of the compound A1-b of the synthesis example 1, the compound A5 of 2.4 g (59%) was obtained by reacting the compound A5-c (5.4 mmol), n-BuLi (2.5M in n-hexane, 2.2 mL) and 9H-fluoren-9-one (5.4 mmol).

Embodiment 1: Fabrication of Light Emitting Diode

A light emitting diode (LED) including the compound A1 synthesized in the synthesis example 1 was fabricated. After an indium tin oxide (ITO) substrate was cleaned using an ultraviolet (UV) and ozone, the ITO substrate was loaded in an evaporation system. For deposition of a plurality of layers on the substrate, the substrate was transferred to a vacuum deposition chamber. Following layers was sequentially formed under a vacuum of about $10^{-6}$ torr by evaporation from a heating boat.

A hole injecting layer (HIL) of HATCN (50 Å), a hole transporting layer (HTL) of NPD (800 Å), an emitting material layer (EML) (300 Å) of a host of AND and a dopant of A1 (5%), an electron transporting layer (ETL) of ET-1 (2-[4-(9,10-di-2-naphthalenyl-2-anthracenyl)phenyl]-1-phenyl-1H-benzimidazole (200 Å), an electron injecting layer (EIL) of LiF (5 Å) and a cathode of A1 (1000 Å).

Embodiment 2: Fabrication of Light Emitting Diode

Through a process the same as that of the embodiment 1 except that the compound A2 synthesized in the synthesis example 2 was used for the dopant of the EML instead of the compound A1, the LED was fabricated.

Embodiment 3: Fabrication of Light Emitting Diode

Through a process the same as that of the embodiment 1 except that the compound A3 synthesized in the synthesis example 3 was used for the dopant of the EML instead of the compound A1, the LED was fabricated.

Embodiment 4: Fabrication of Light Emitting Diode

Through a process the same as that of the embodiment 1 except that the compound A4 synthesized in the synthesis example 4 was used for the dopant of the EML instead of the compound A1, the LED was fabricated.

Embodiment 5: Fabrication of Light Emitting Diode

Through a process the same as that of the embodiment 1 except that the compound A5 synthesized in the synthesis example 5 was used for the dopant of the EML instead of the compound A1, the LED was fabricated.

Comparative Example: Fabrication of Light Emitting Diode

Through a process the same as that of the embodiment 1 except that diphenyl-[4-(2-[1,1;4,1]terphenyl-4-yl-vinyl)-phenyl]-amine (BD-1) was used for the dopant of the EML instead of the compound A1, the LED was fabricated.

Embodiment 6: Measurement of Physical Property of Light Emitting Diode

Physical properties of the LEDs fabricated through the embodiments 1 to 5 and the comparative example were measured. After the plurality of layers were formed on the first substrate, the first substrate having the plurality of layers was transferred from a deposition chamber to a dry box. Next, the first substrate having the plurality of layers was encapsulated using a UV curable epoxy and a moisture getter to form the second substrate. The LEDs fabricated from the embodiments 1 to 5 have an emitting area of 2 m². The LEDs were connected to an external power supply, and emission properties of the LEDs fabricated from the embodiments 1 to 5 and the comparative example were measured under a room temperature using a constant current source (KEITHLEY) and a photometer (PR 650). The measurement results according to the present disclosure are shown in a following TABLE 1. The emission efficiency and the lifetime are obtained through measurement with respect to the comparative example. In TABLE 1, it was verified that the emission efficiency and the lifetime of the LED including the organic compound synthesized according to the embodiments 1 to 5 of the present disclosure were improved.

TABLE 1

| | Host | Dopant | Voltage | Emission Efficiency (EQE) | CIEx | CIEy | T80 Lifetime |
|---|---|---|---|---|---|---|---|
| Embodiment 1 | ADN | A1 | 99% | 121% | 0.135 | 0.112 | 148% |
| Embodiment 2 | ADN | A2 | 100% | 120% | 0.135 | 0.120 | 160% |
| Embodiment 3 | ADN | A3 | 100% | 105% | 0.134 | 0.101 | 157% |
| Embodiment 4 | ADN | A4 | 99% | 134% | 0.135 | 0.119 | 191% |
| Embodiment 5 | ADN | A5 | 100% | 125% | 0.136 | 0.114 | 150% |
| Comparative Example | ADN | BD-1 | 100% | 100% | 0.149 | 0.155 | 100% |

Consequently, in the organic compound according to the present disclosure, the core includes the aromatic ring or the hetero aromatic ring having the fused structure, and the amine group is directly or indirectly connected to the fused aromatic core and/or the other aromatic ring. In the organic compound synthesized according to the exemplary embodiment of the present disclosure, the nitrogen atom constituting the amine group may be not substituted or may be substituted with a functional group having an electron withdrawing group or an electron donating group. The aromatic core of the fused structure is connected to the other aromatic ring through the spiro structure.

Since the organic compound according to the present disclosure has the relatively high glass transition temperature (Tg), the thermal stability of the material is improved. Since the organic compound includes the aromatic core of the fused structure, the at least one aromatic ring and the amine group directly or indirectly connected to the aromatic core of the fused structure and/or the at least one aromatic ring, the emission property is improved. The hole transport property, the hole movement property and the color purity are improved due to the aromatic core, the other aromatic ring and the functional group substituted for the nitrogen atom.

As a result, the organic compound according to the present disclosure may be applied to the organic material layer of the LED. For example, the organic compound may be used for the host or the dopant of the LED or for a material of the hole injecting layer and/or the hole transporting layer. The lifetime, the emission efficiency and the emission property of the LED are improved due to the advantages in the thermal stability, the emission property, the color purity, the hole transport property and the hole movement property of the organic compound according to the present disclosure.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An organic compound selected from the following compounds of Chemical Formula 4:

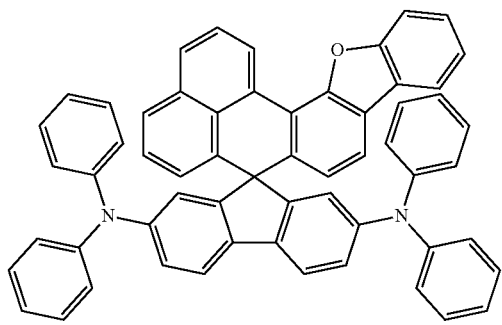

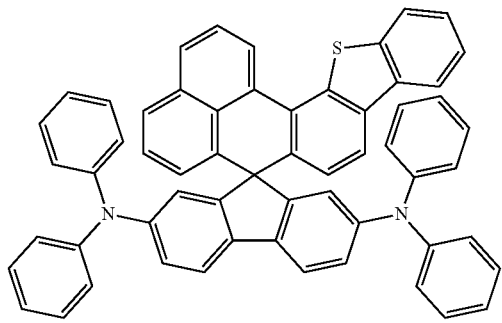

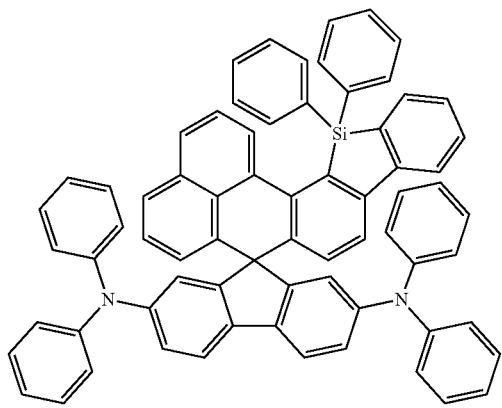

-continued

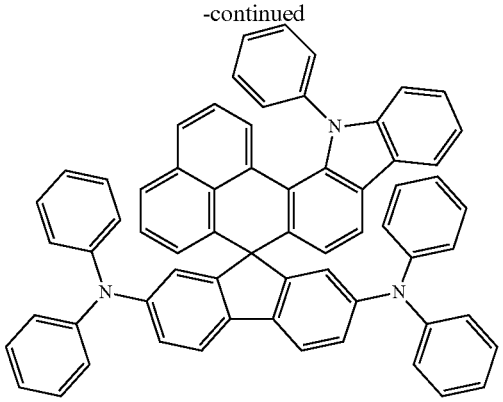

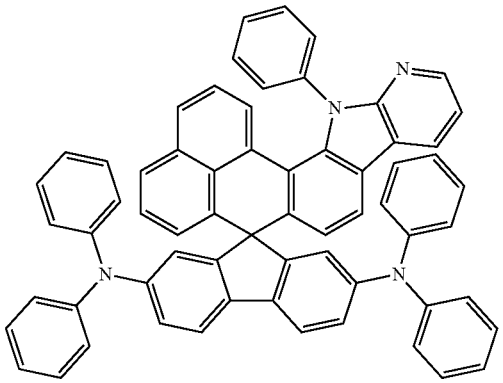

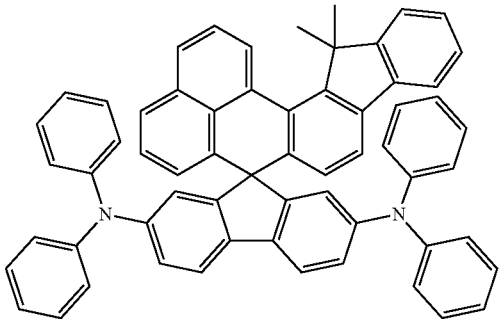

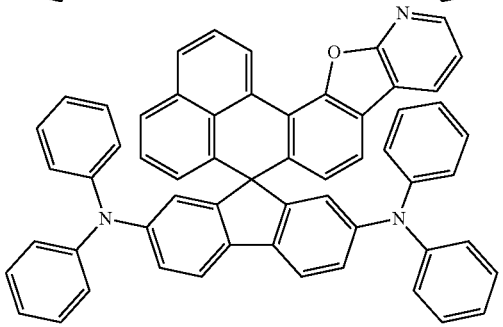

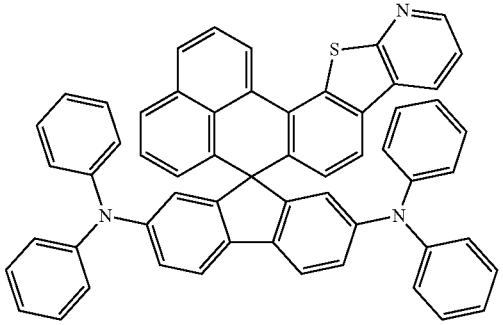

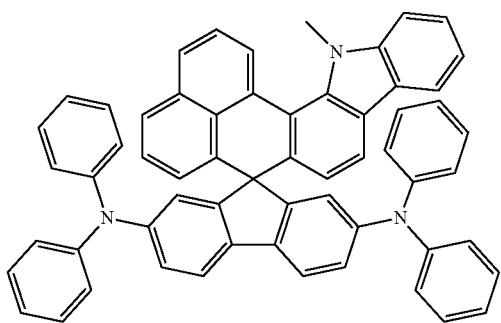
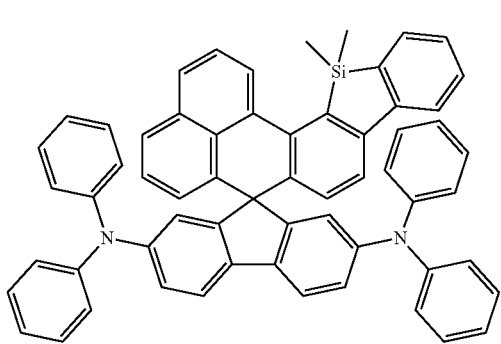
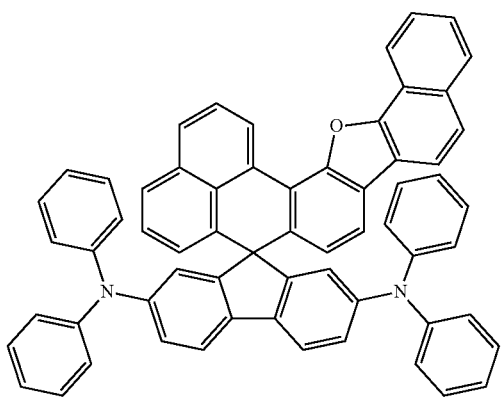
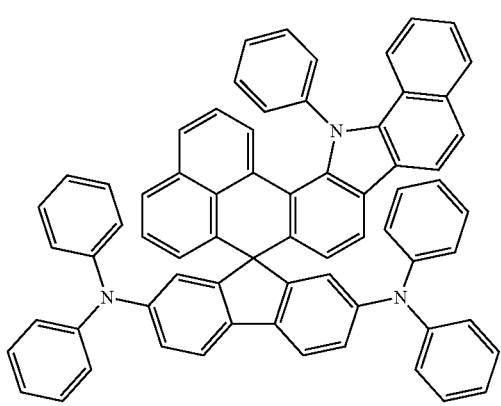
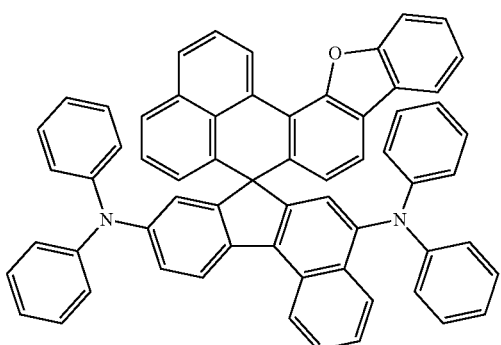
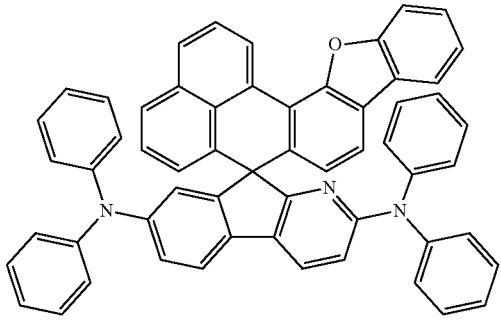
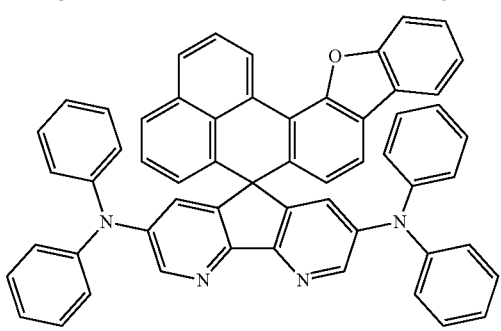
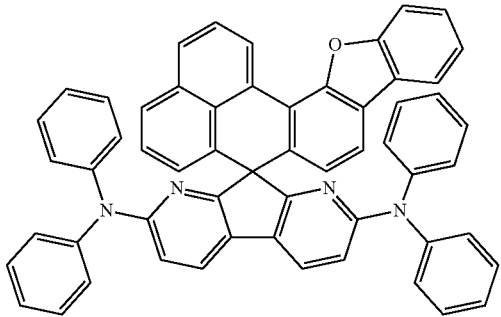
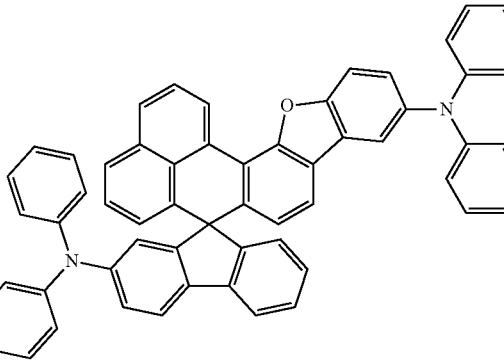

-continued
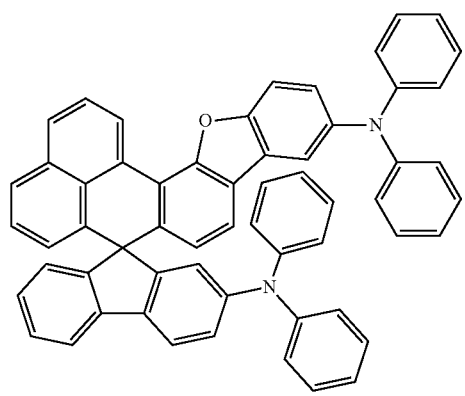
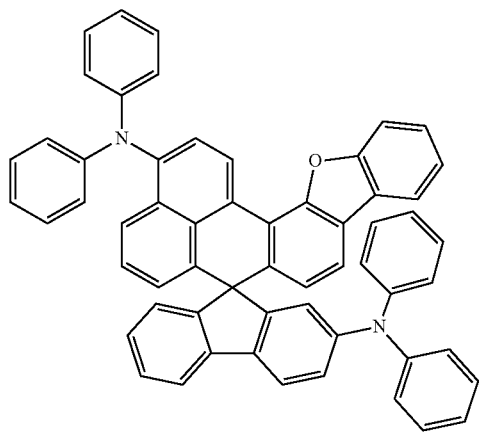
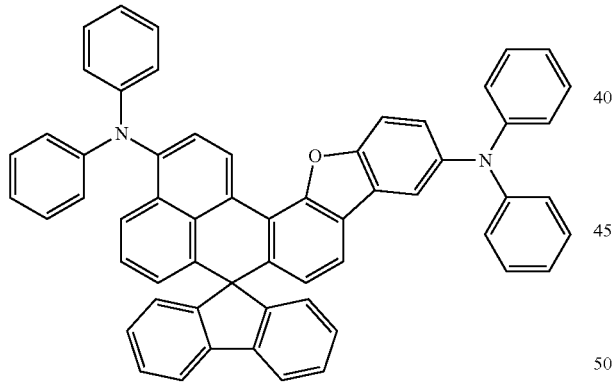
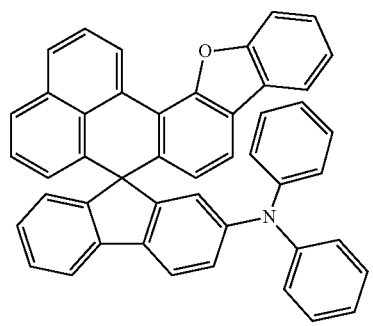
-continued
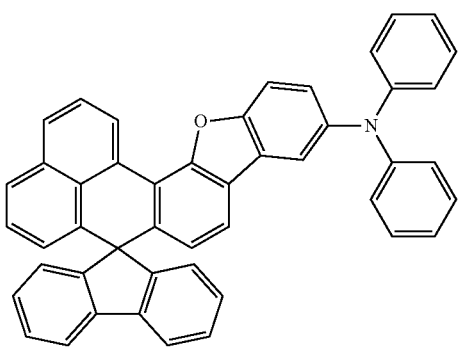
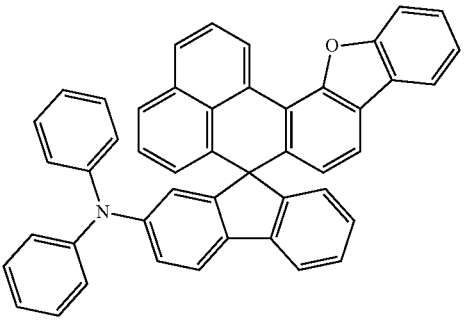
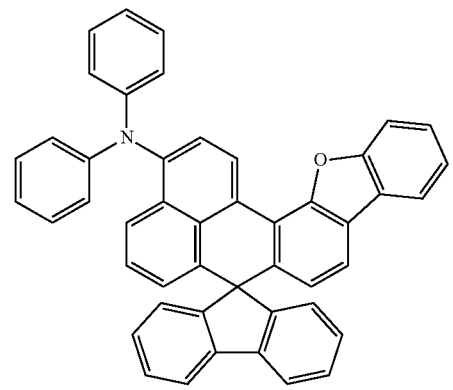
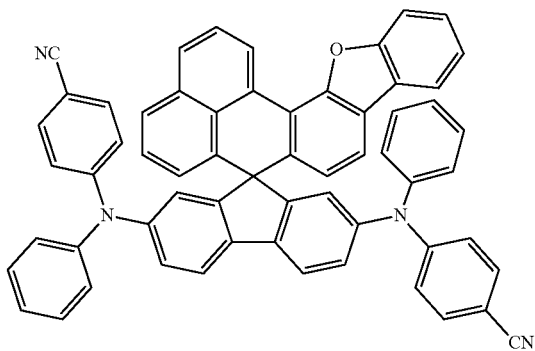

75
-continued
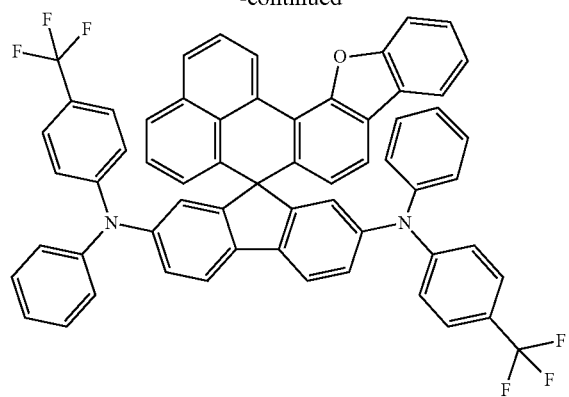
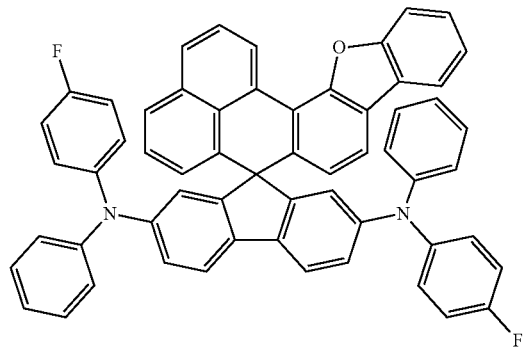
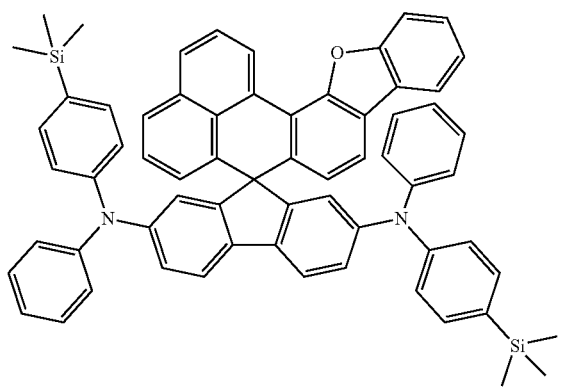
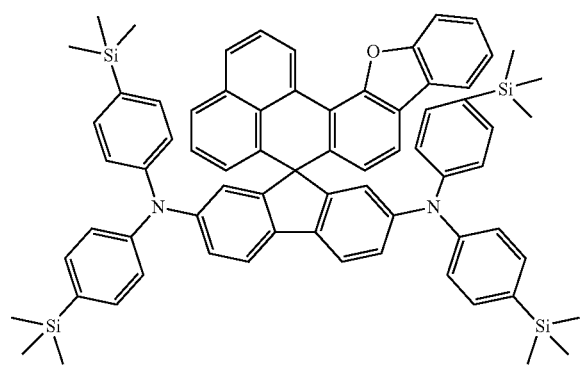
76
-continued
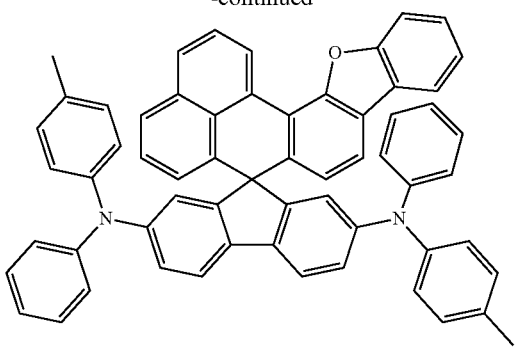
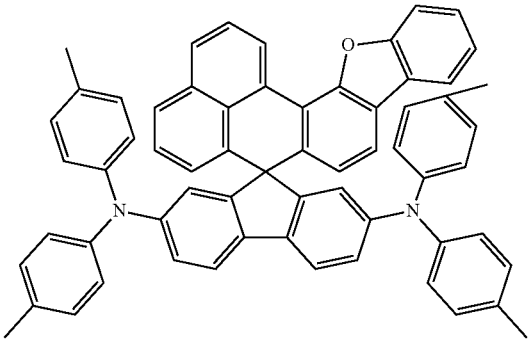
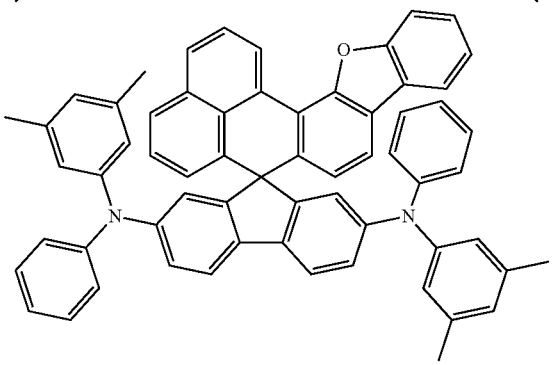
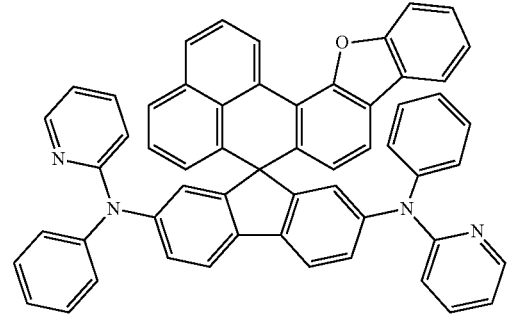
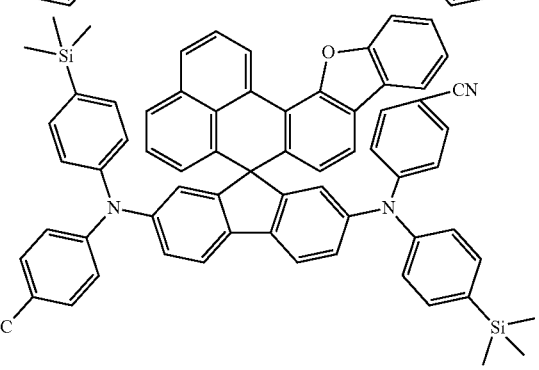

77
-continued
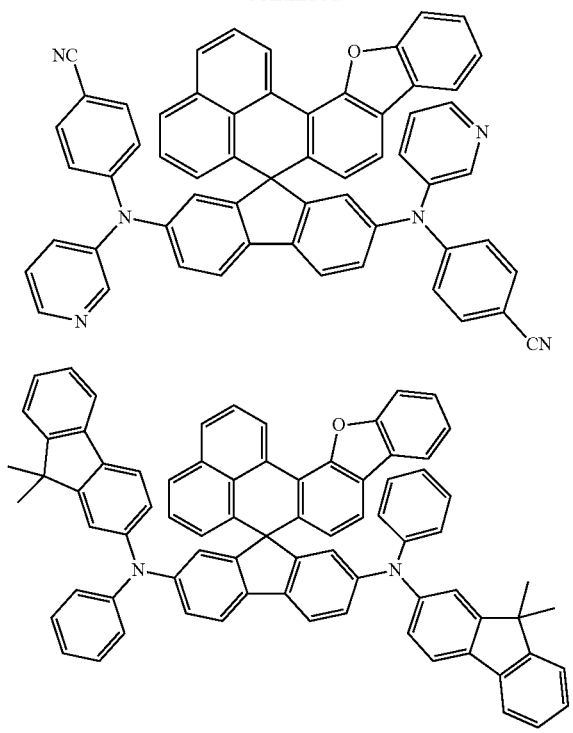
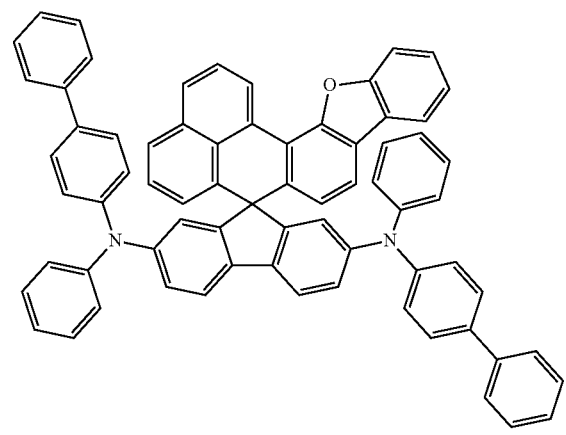
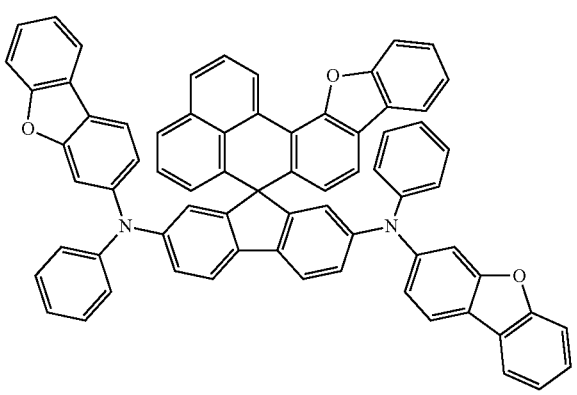
78
-continued
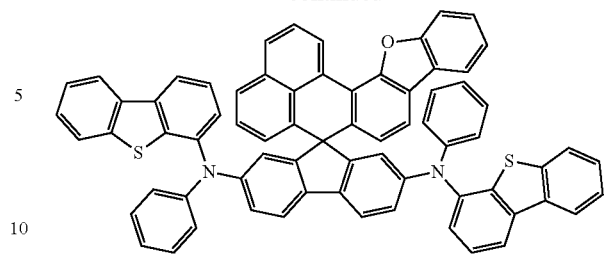
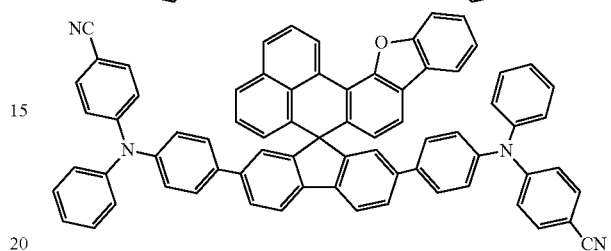
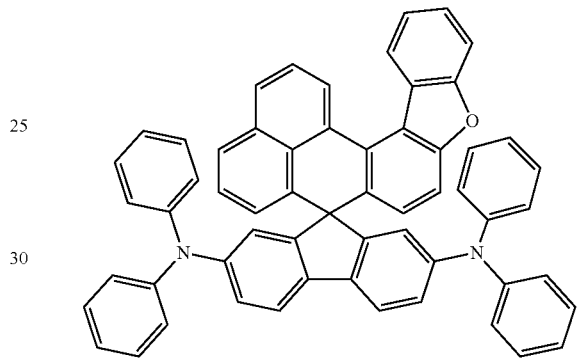
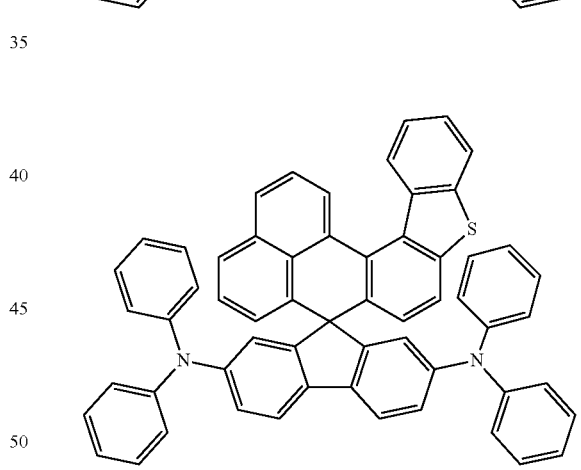
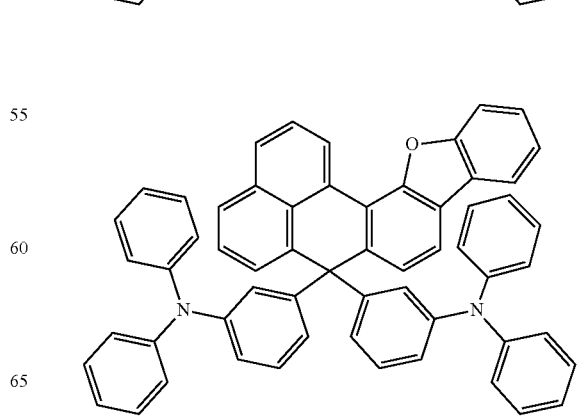

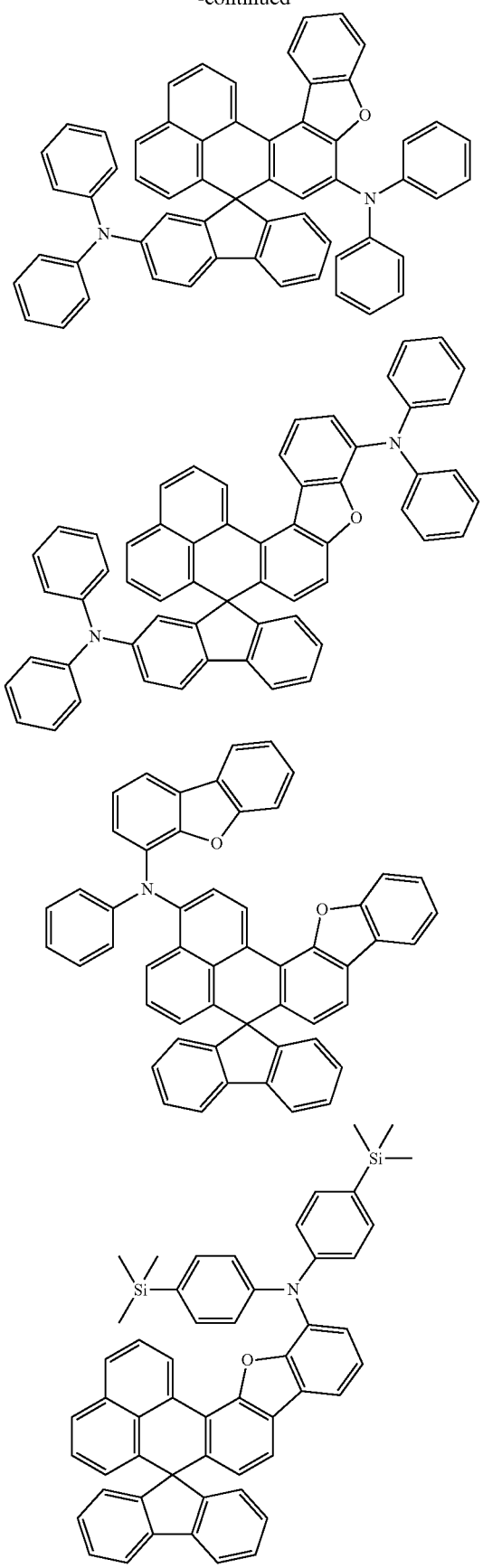
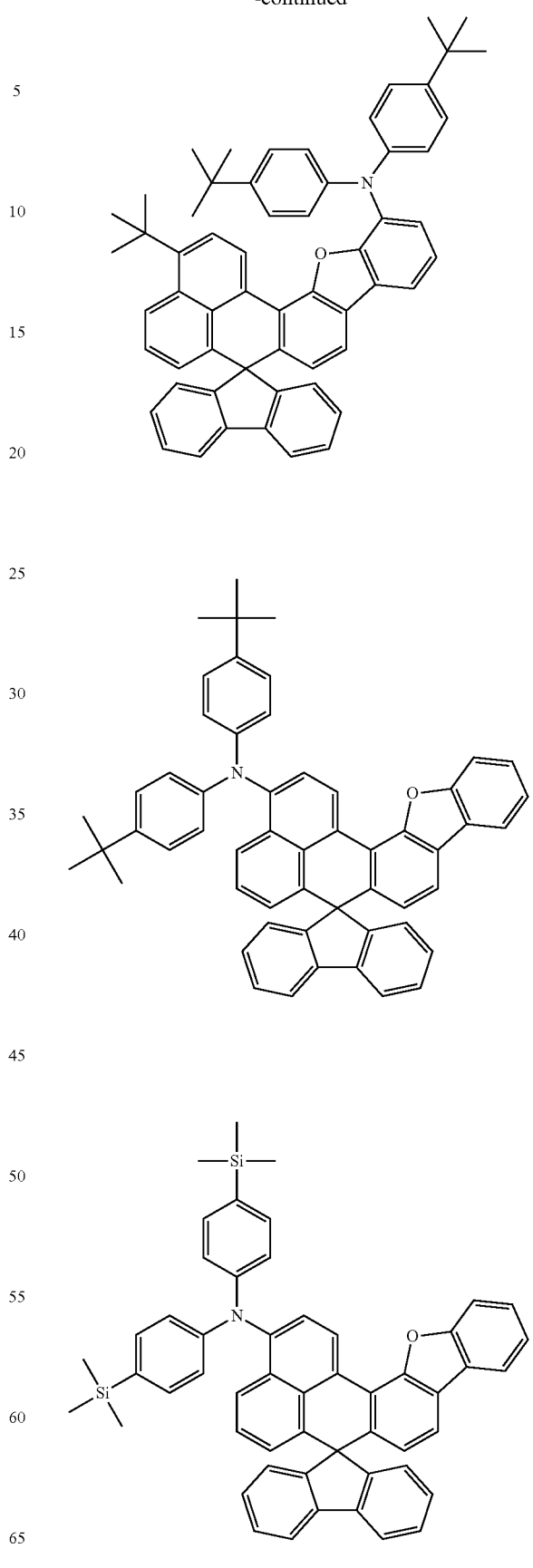

81
-continued
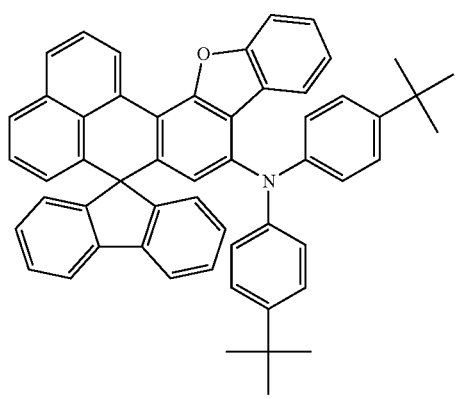
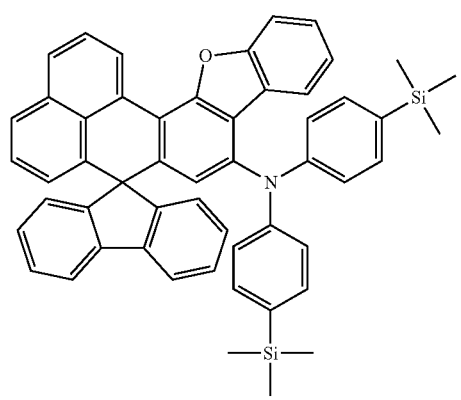
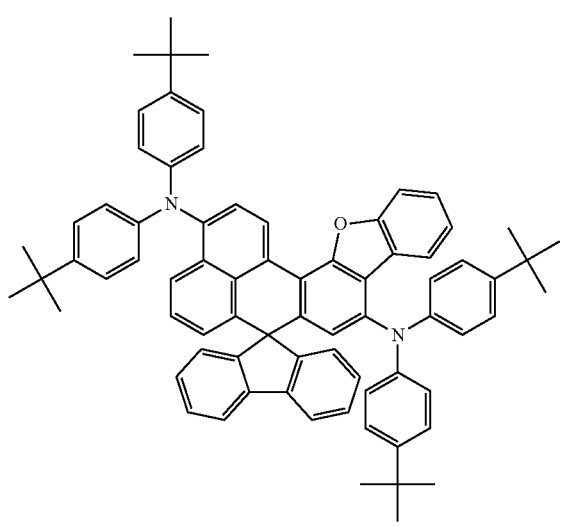
82
-continued
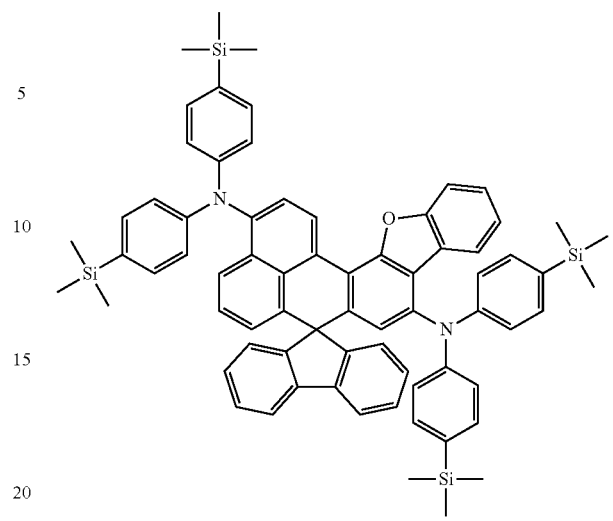
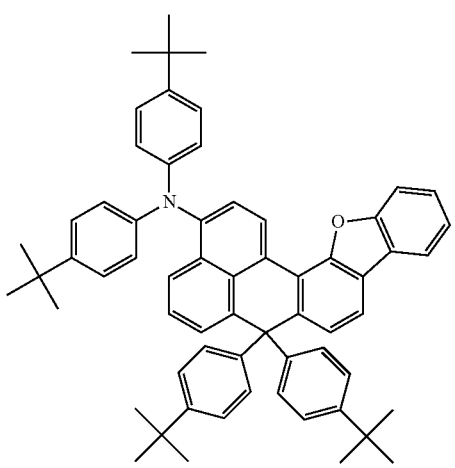
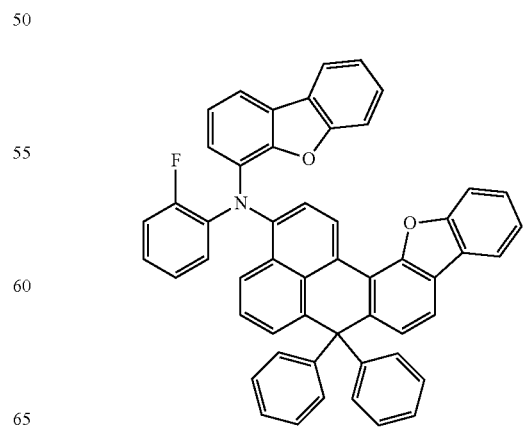

83
-continued
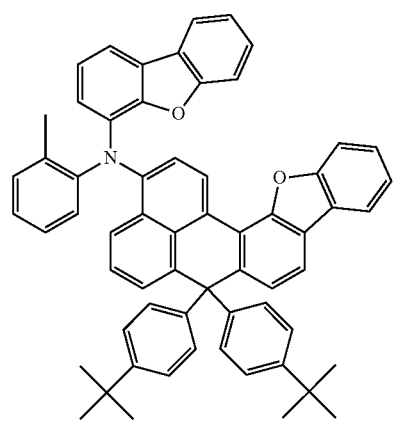
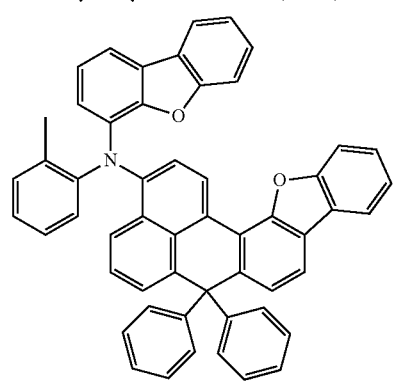
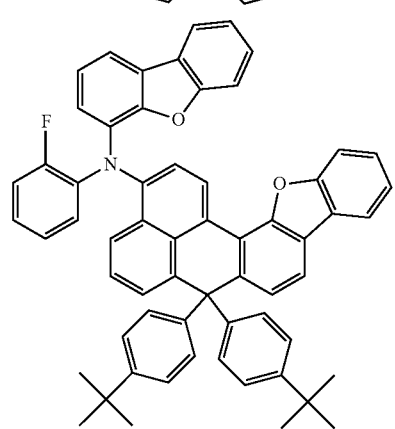
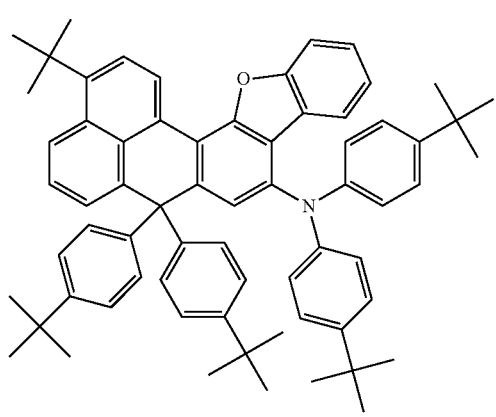
84
-continued
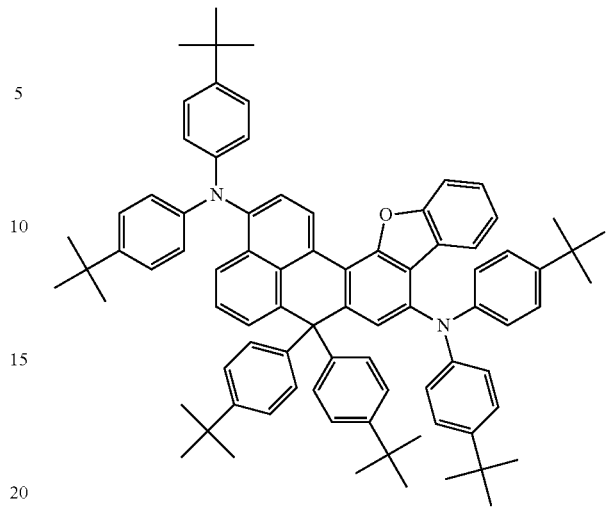
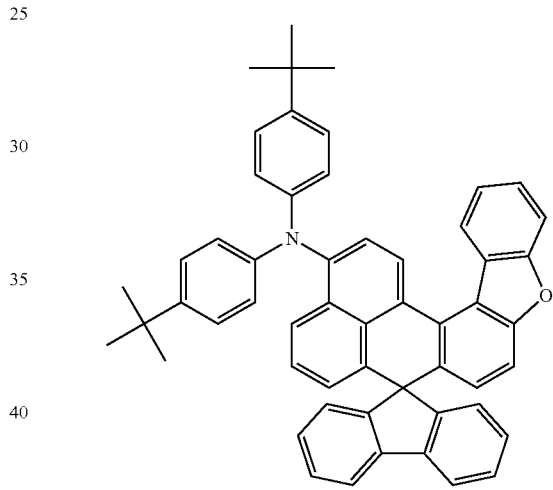
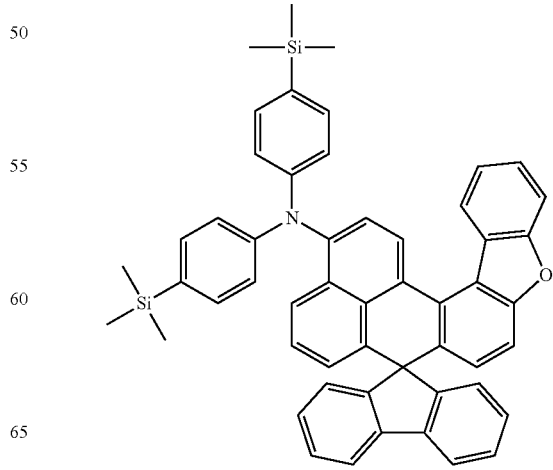

85
-continued
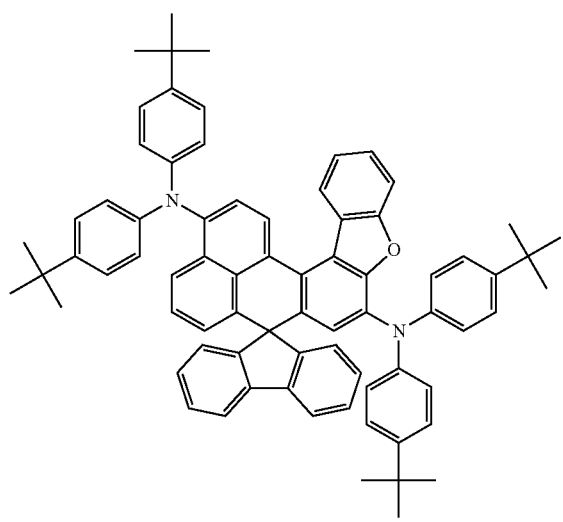
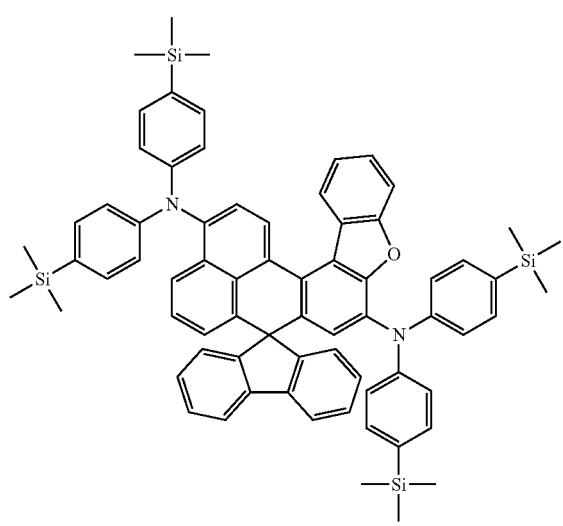
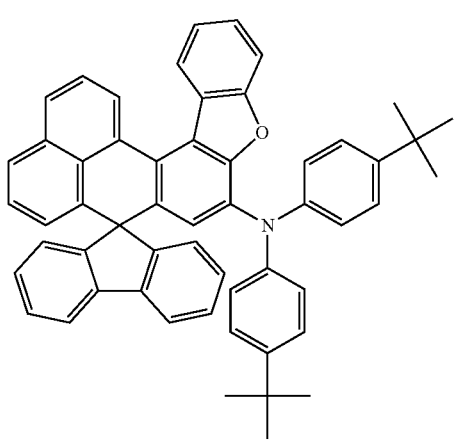
86
-continued
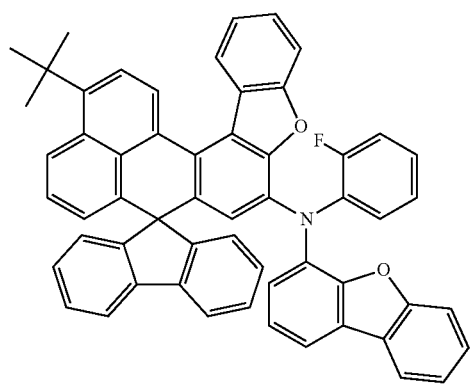
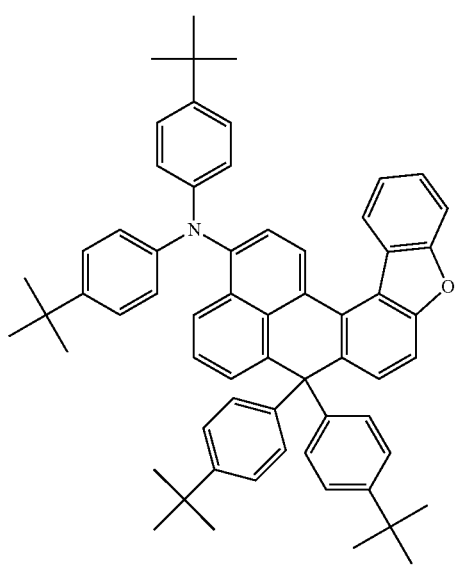
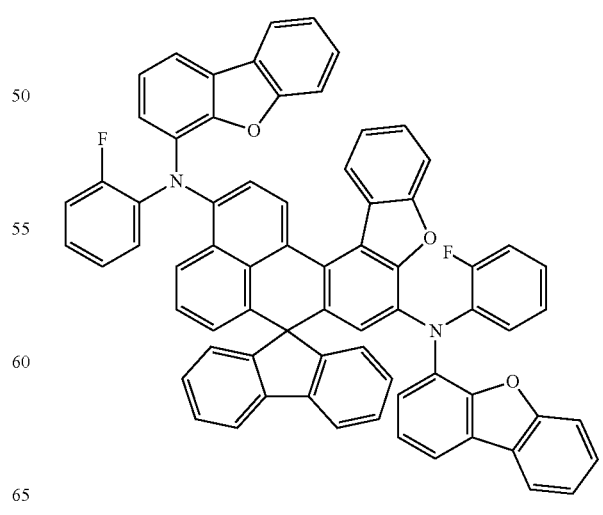

87
-continued
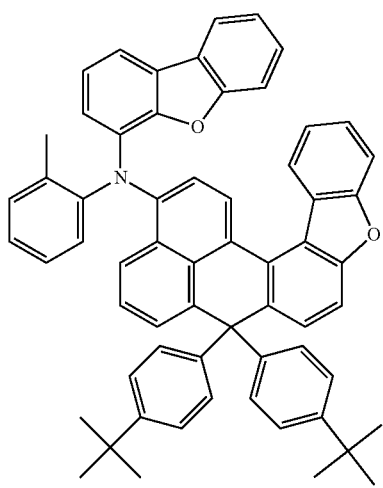
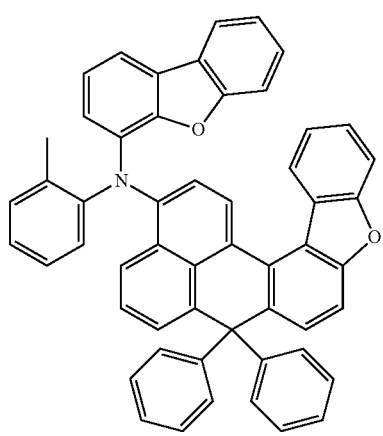
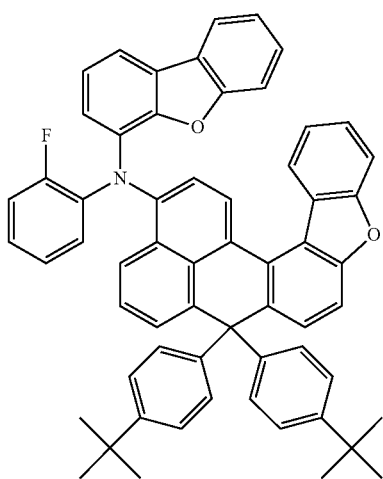
88
-continued
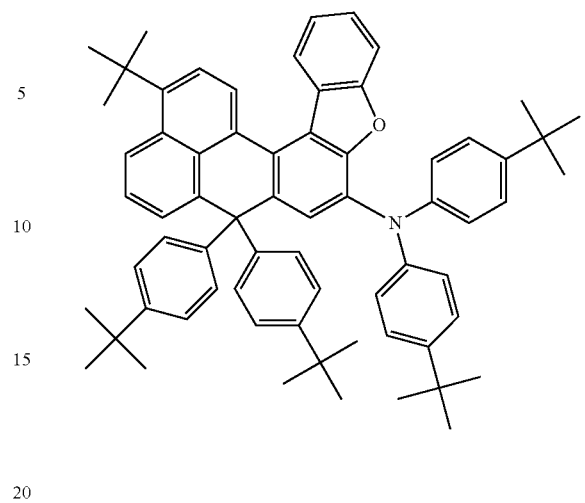
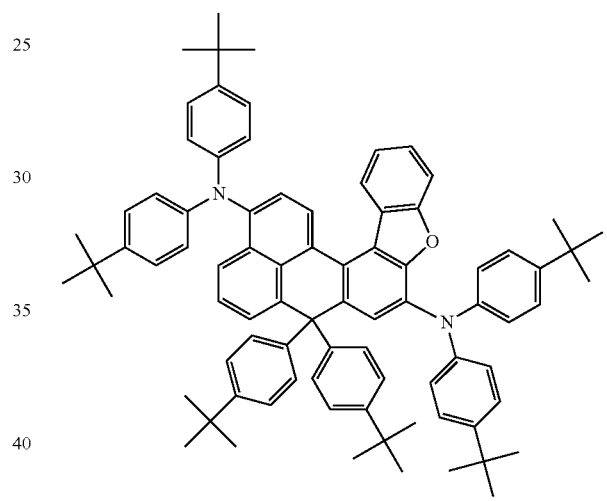
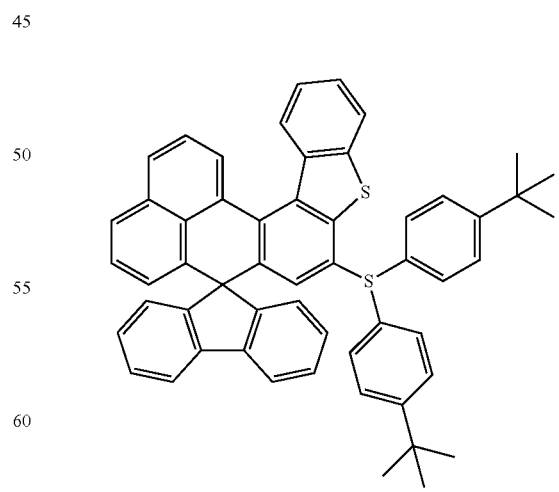

89
-continued
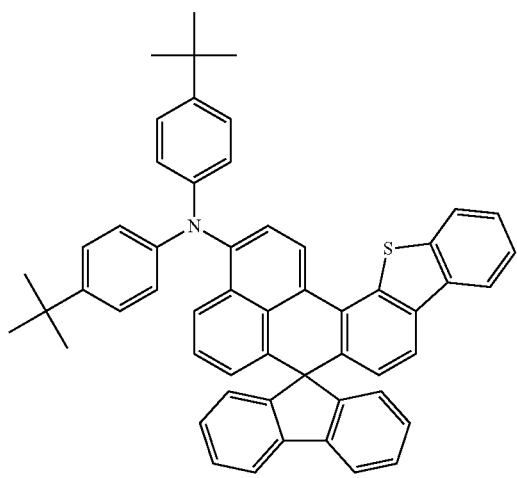
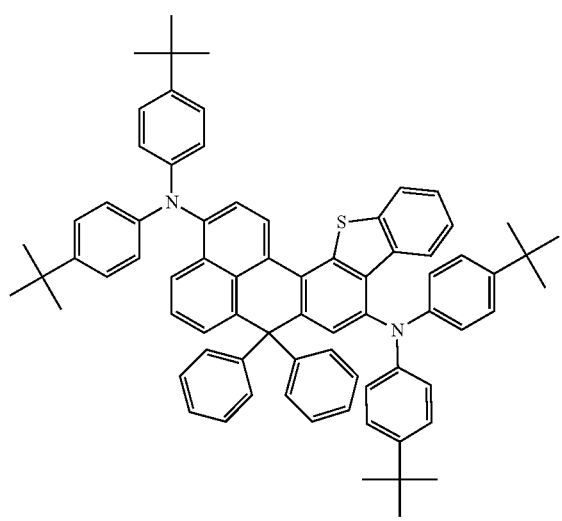
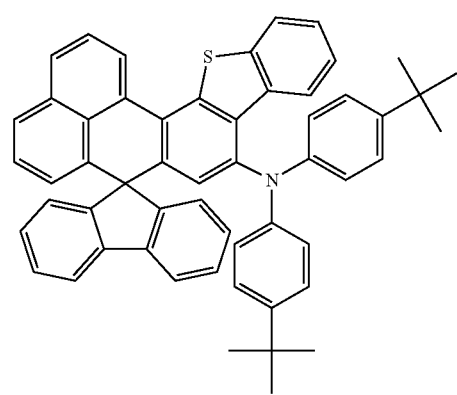
90
-continued
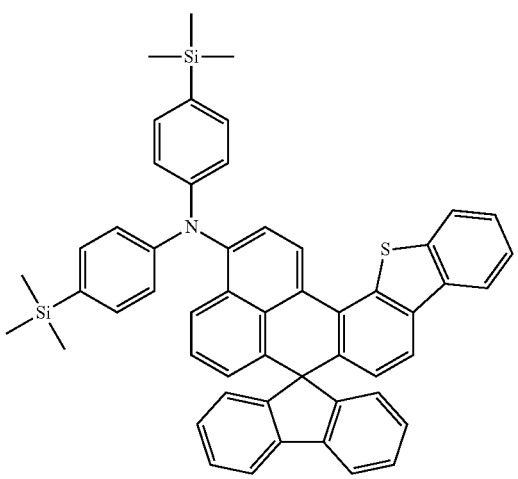
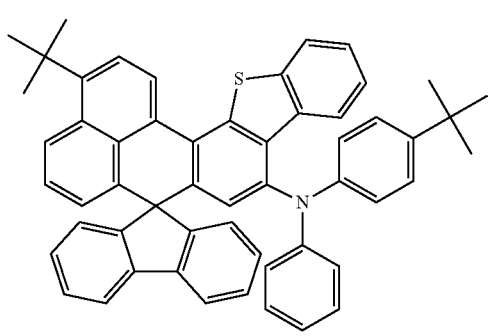
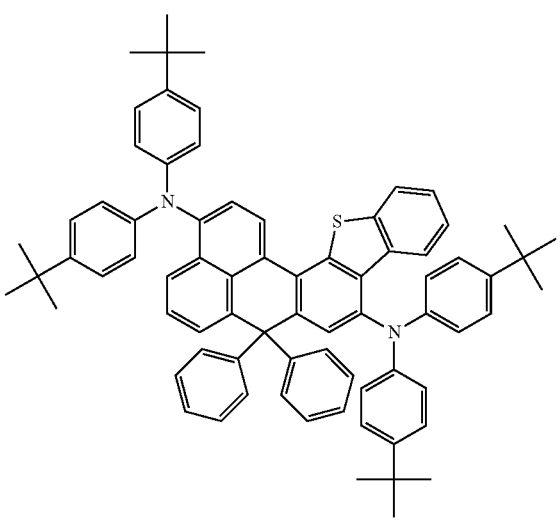

91
-continued
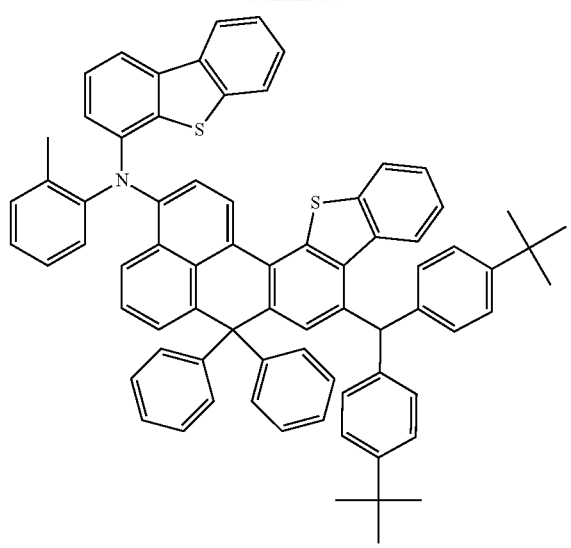
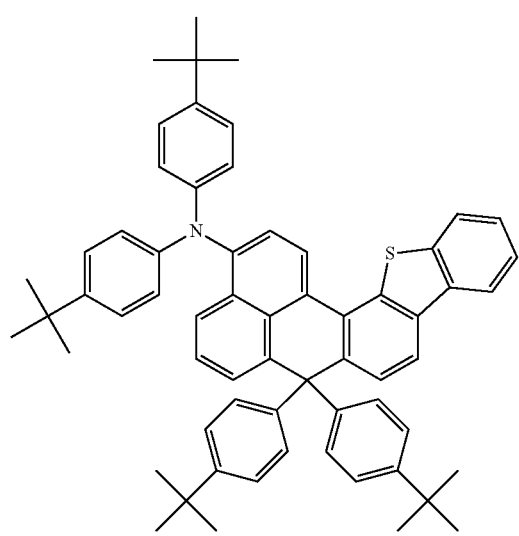
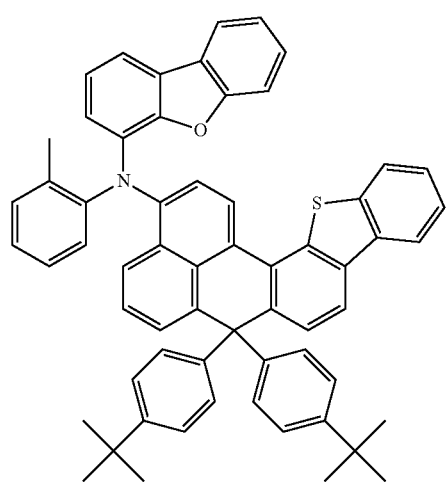
92
-continued
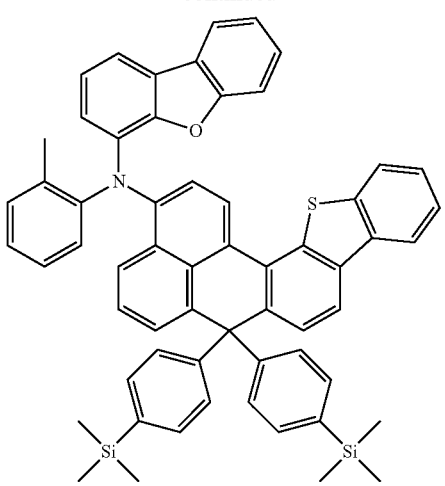
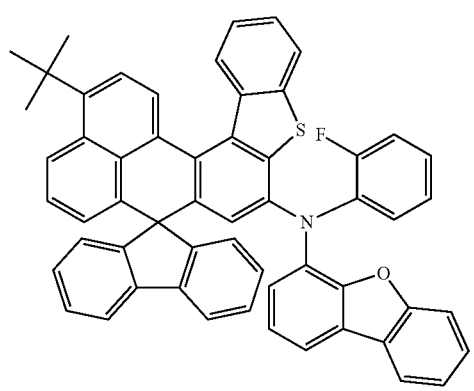
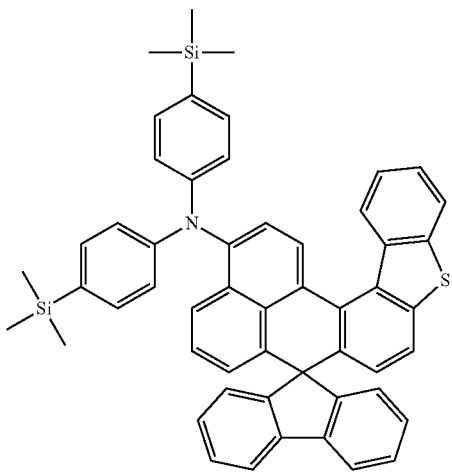

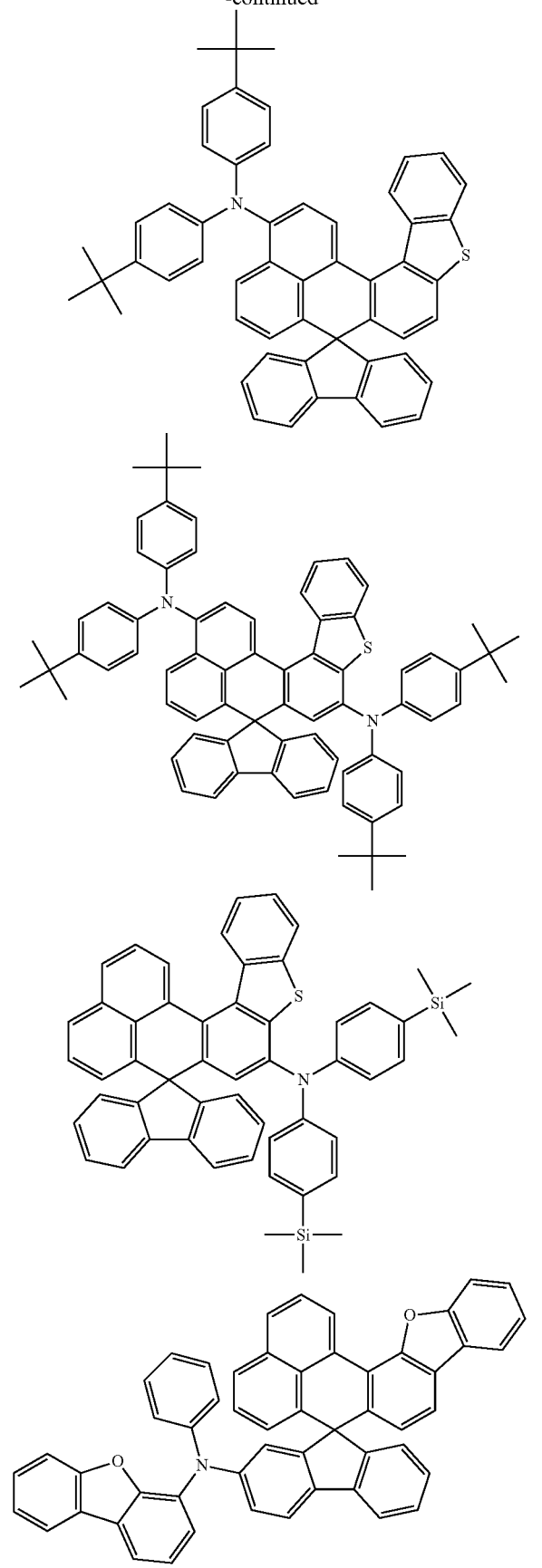
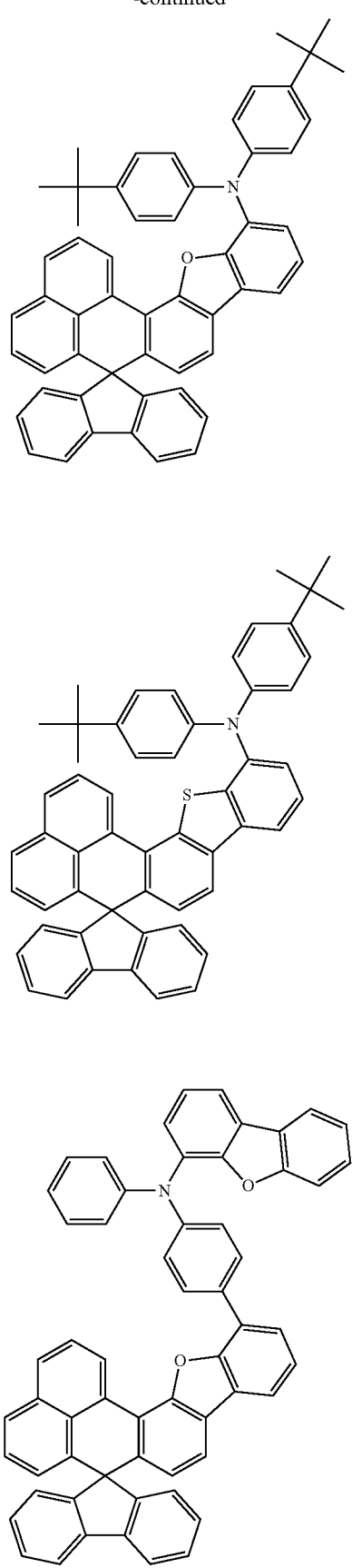

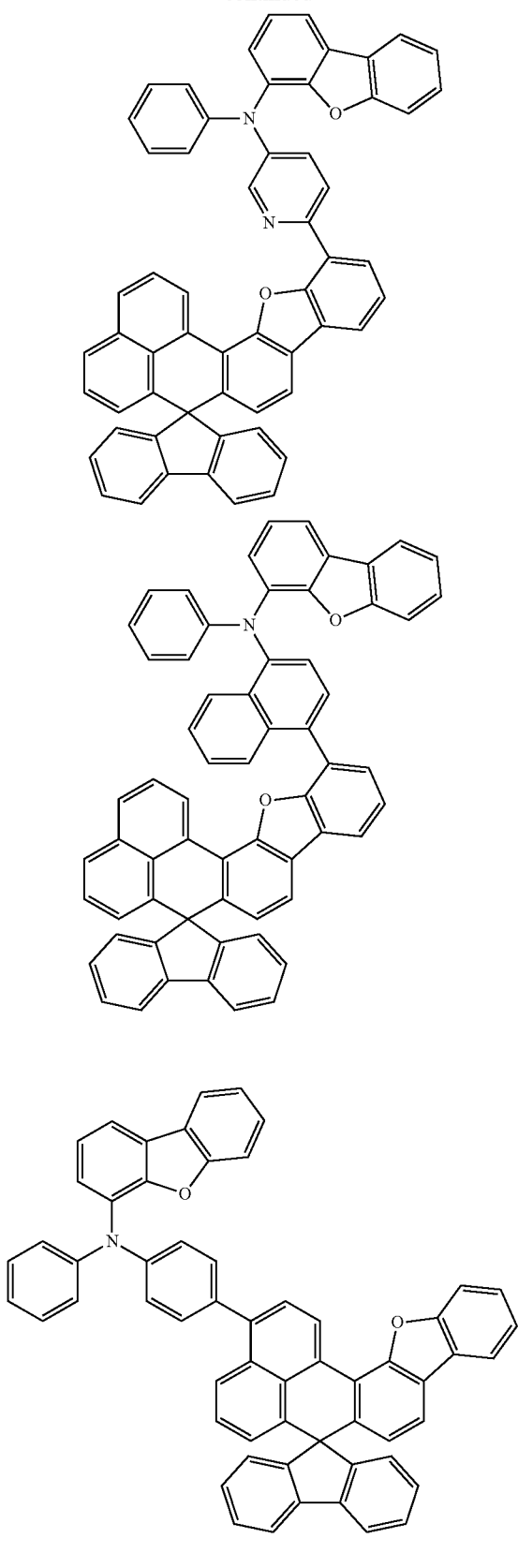
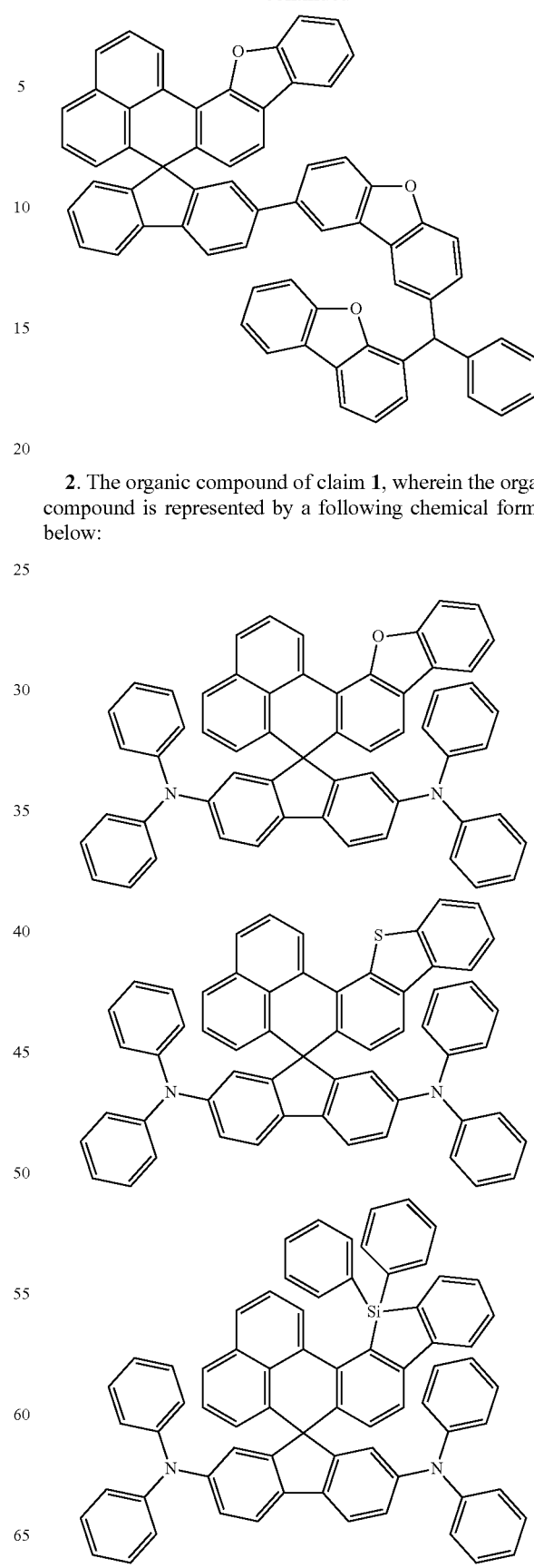
2. The organic compound of claim 1, wherein the organic compound is represented by a following chemical formula below:

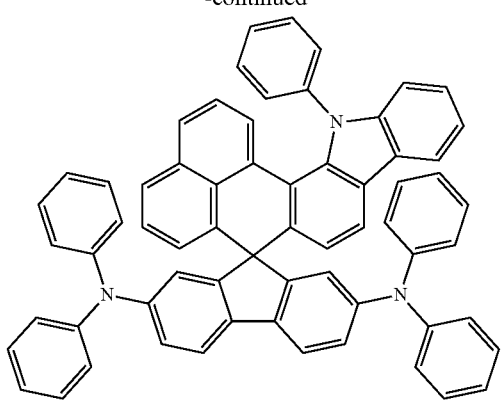
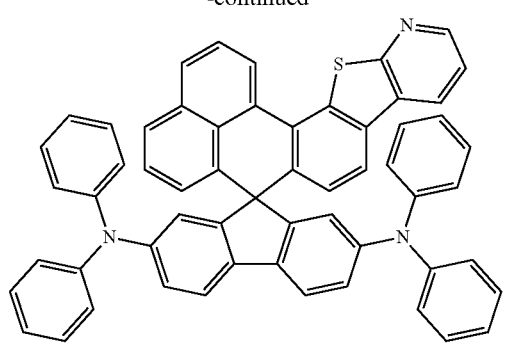
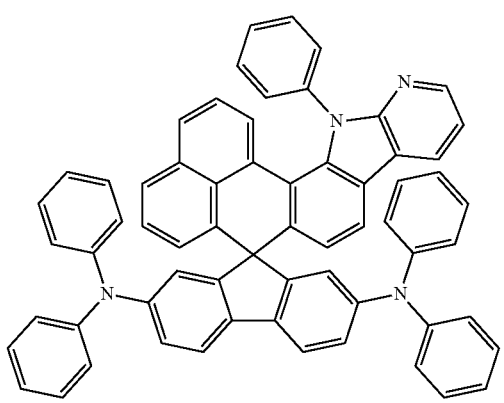
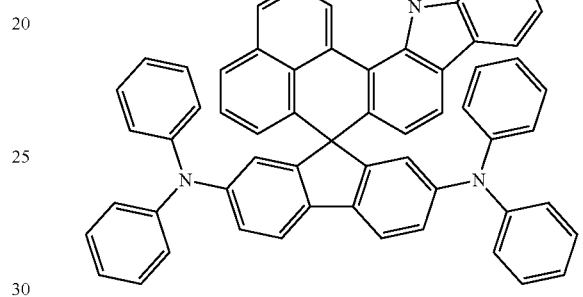
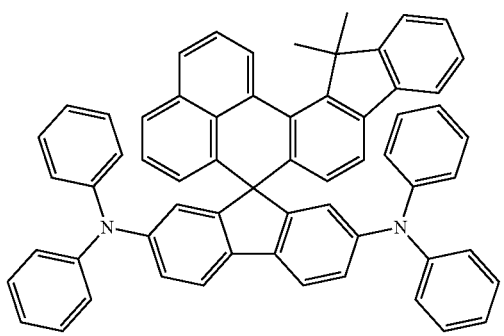
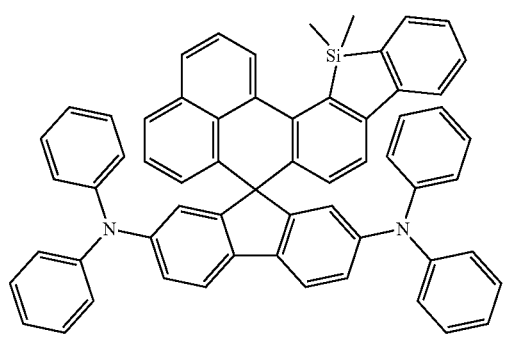
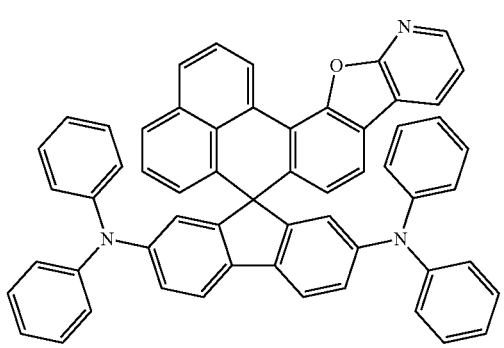
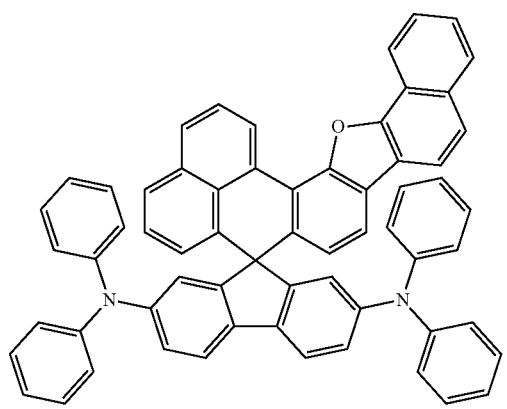

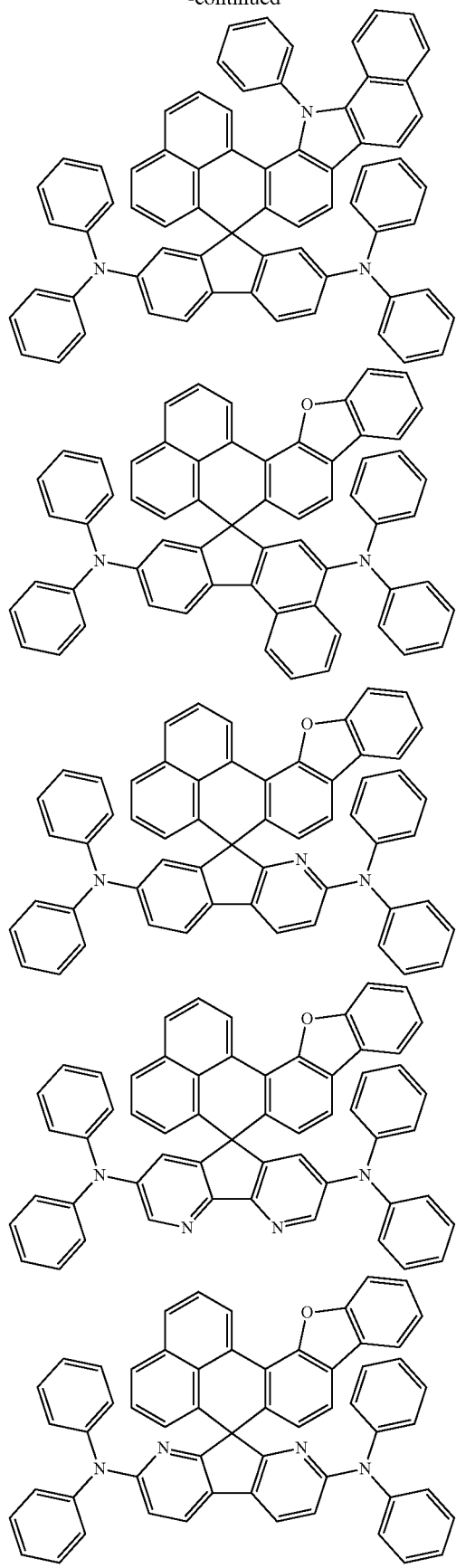
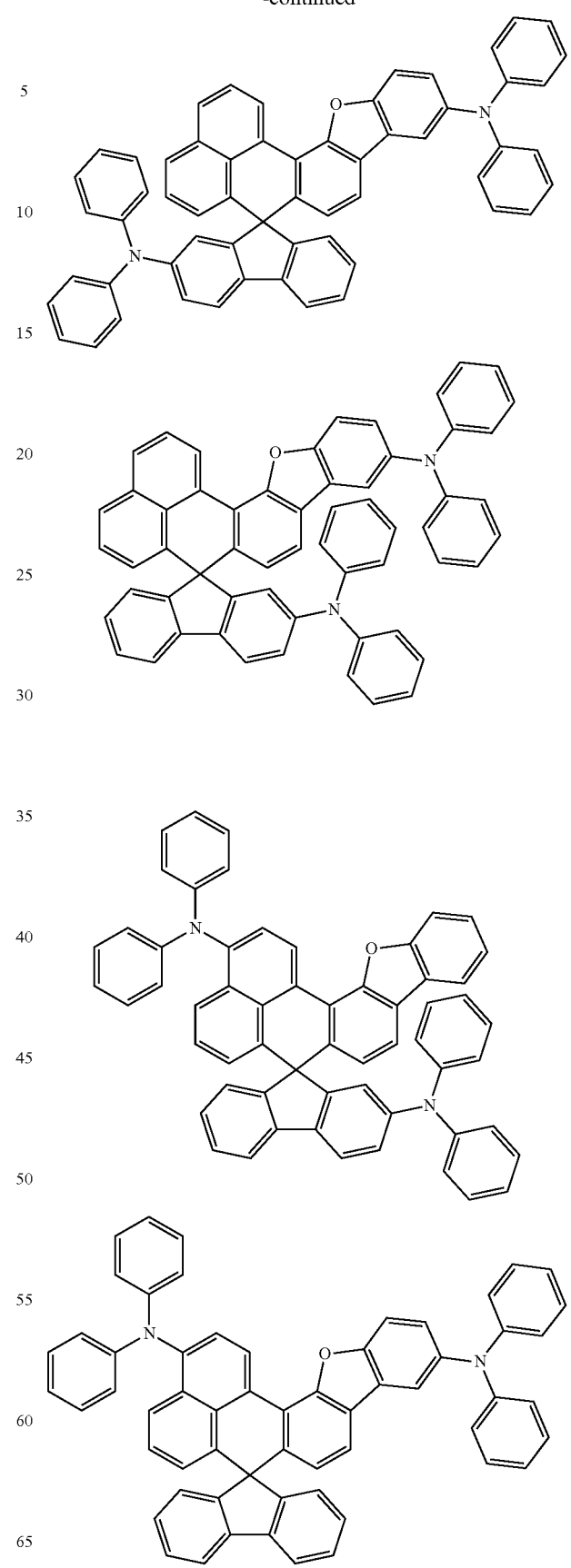

101
-continued
102
-continued
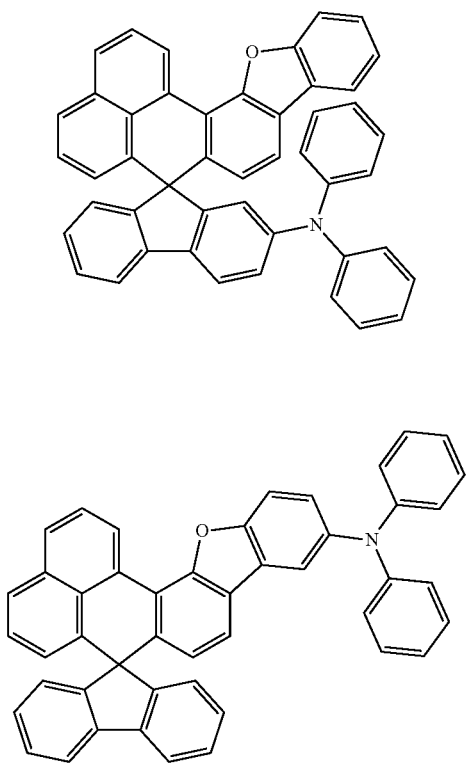
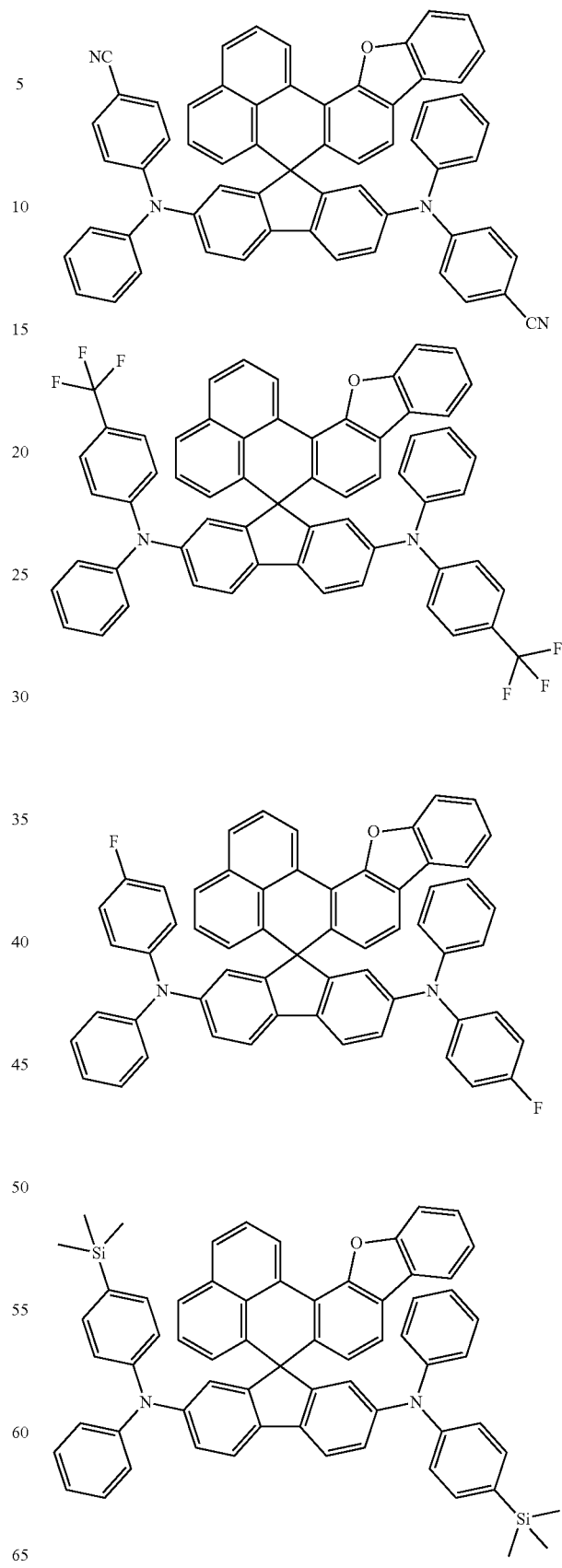

103
-continued
104
-continued
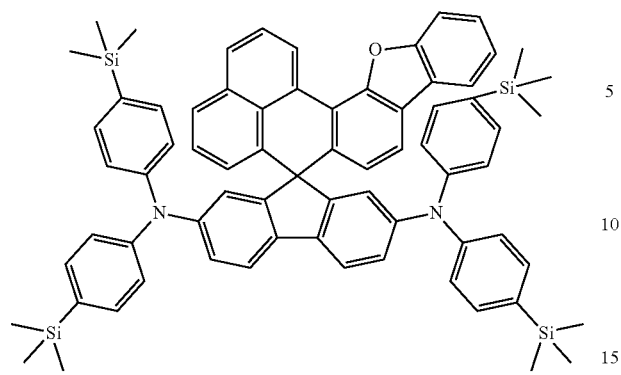
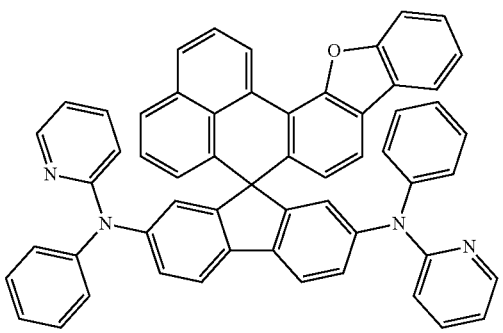
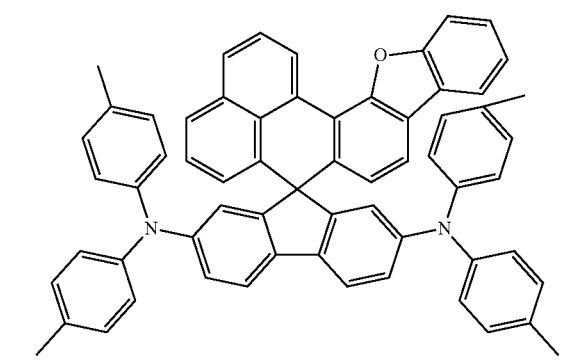
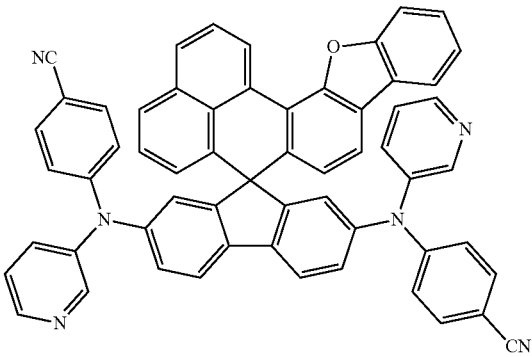
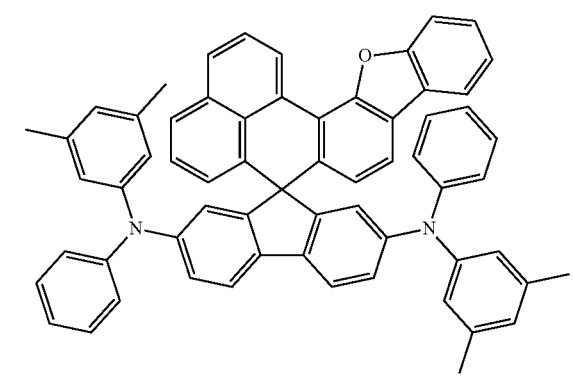
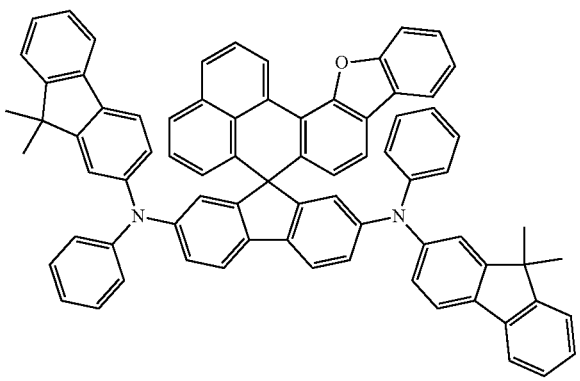

105
-continued
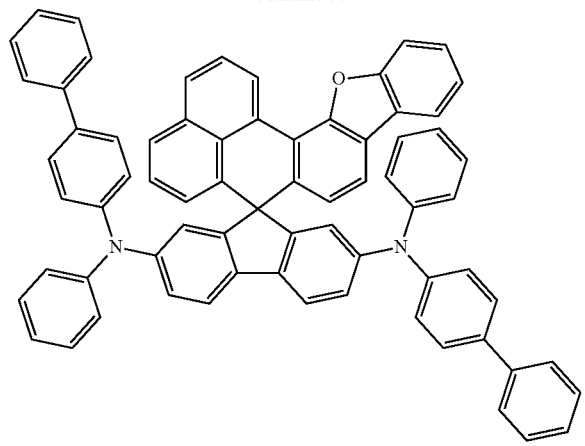
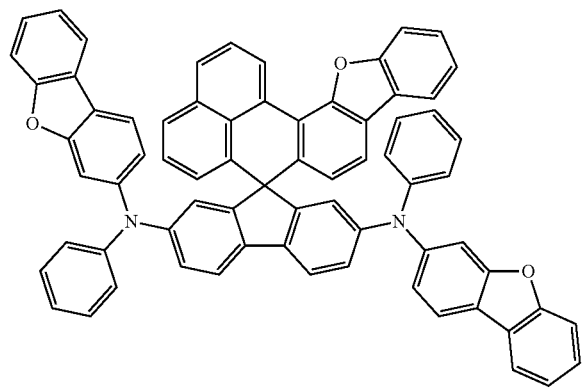
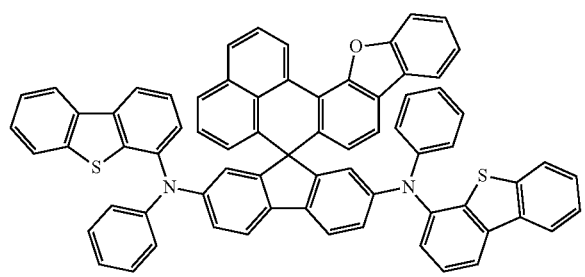
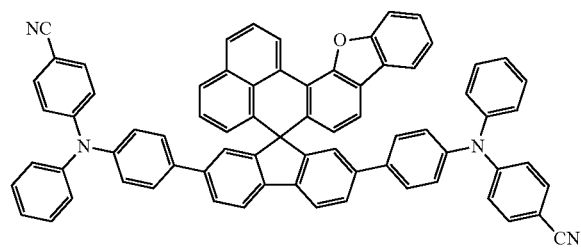
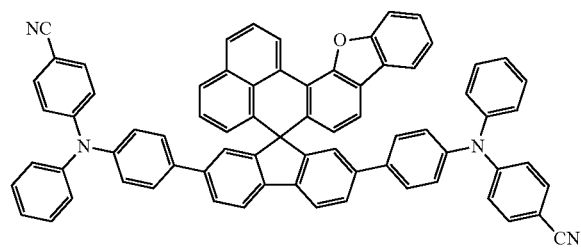
106
-continued
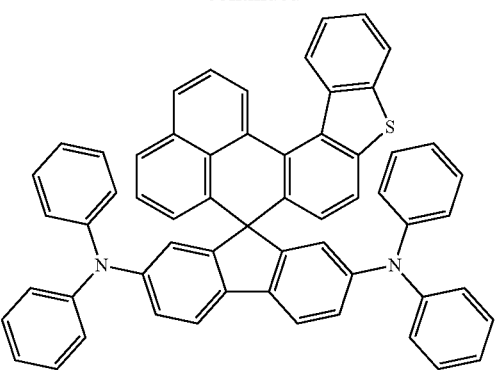
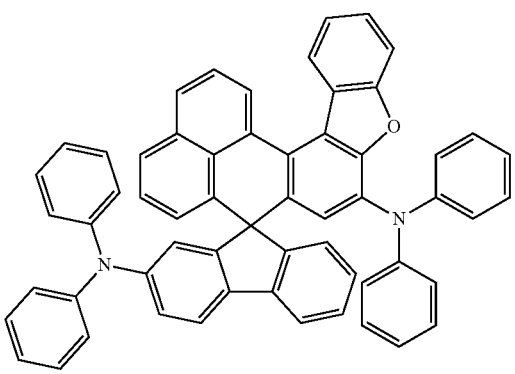
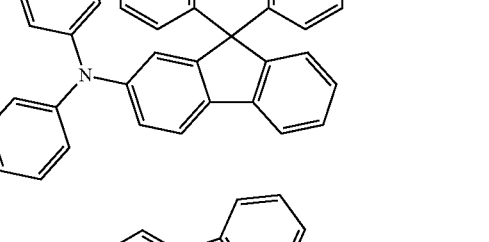
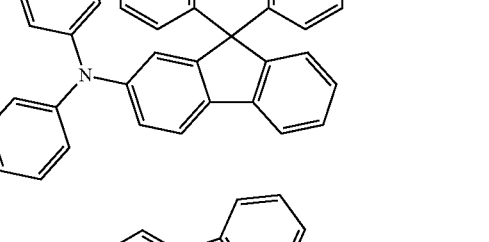

107
-continued
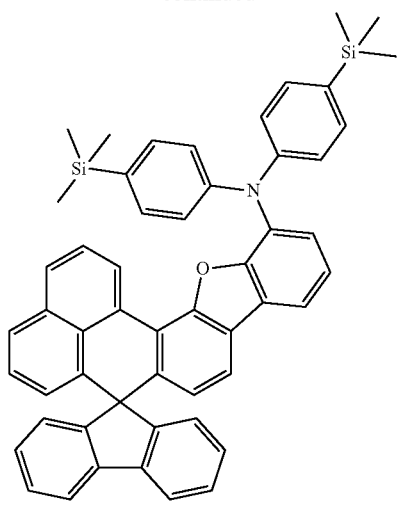
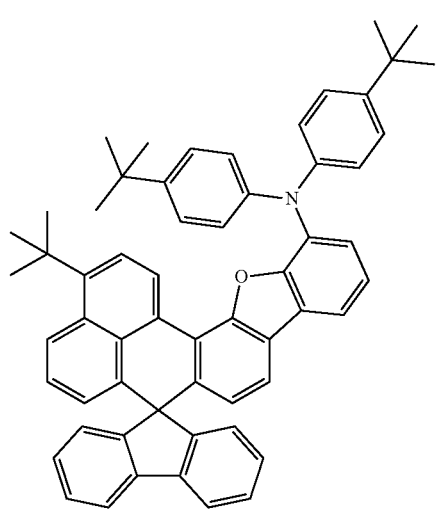
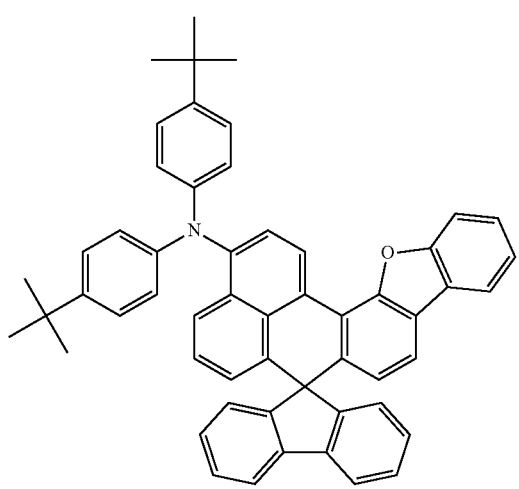
108
-continued
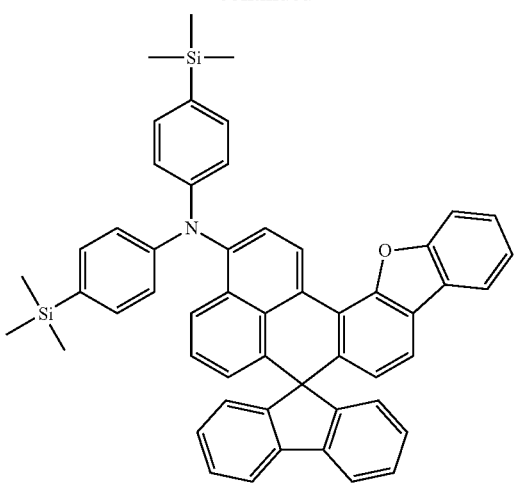
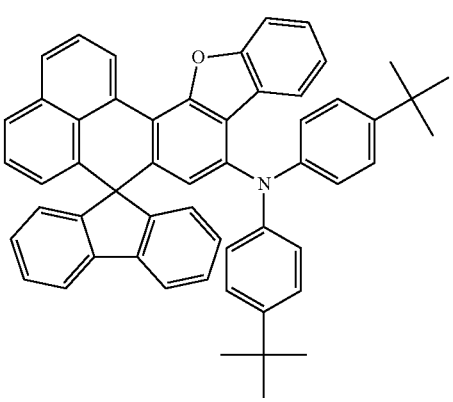
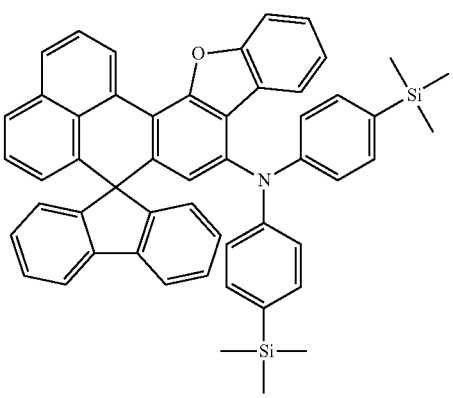

109
-continued
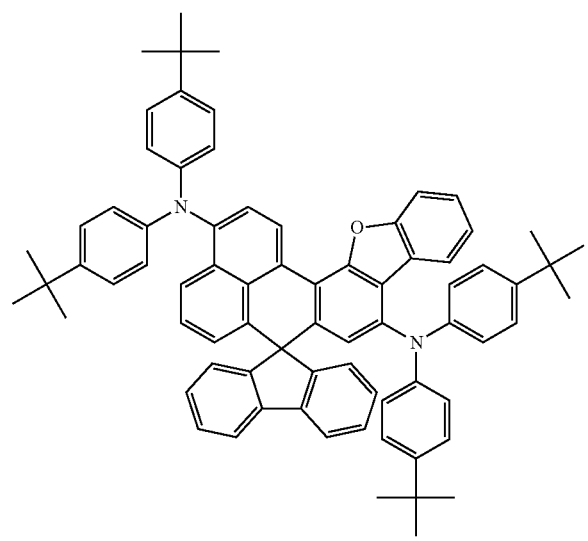
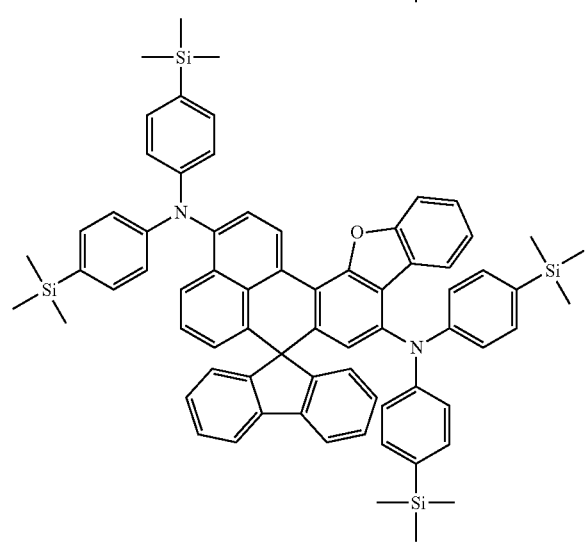
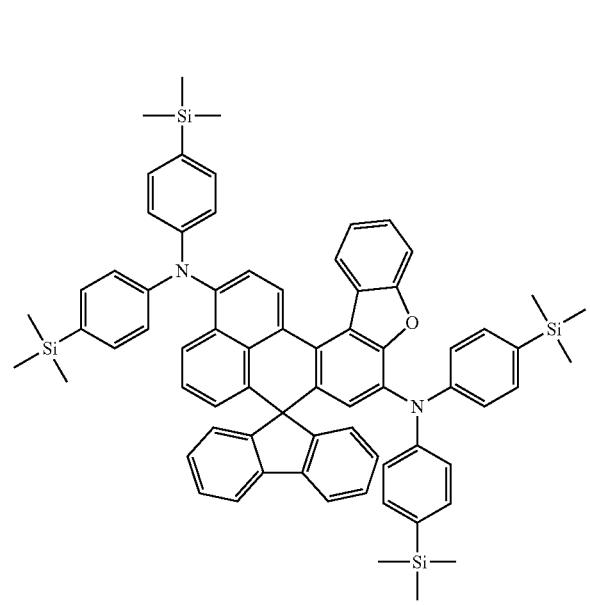
110
-continued
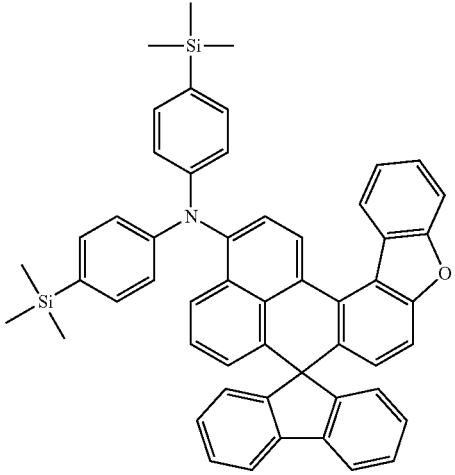

111
-continued
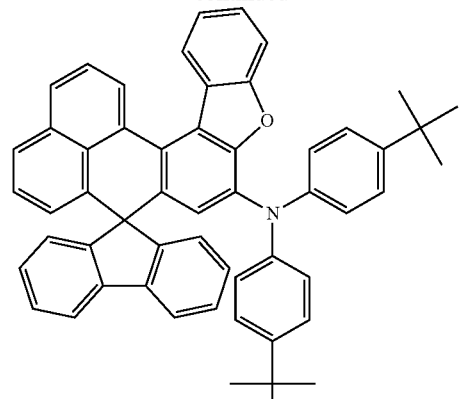
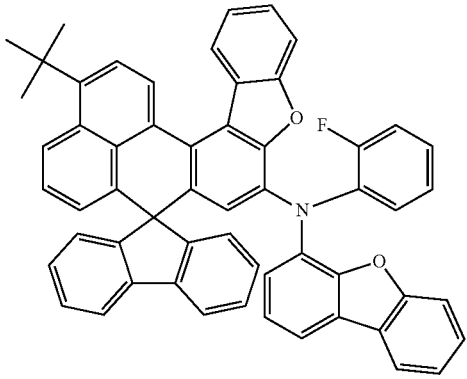
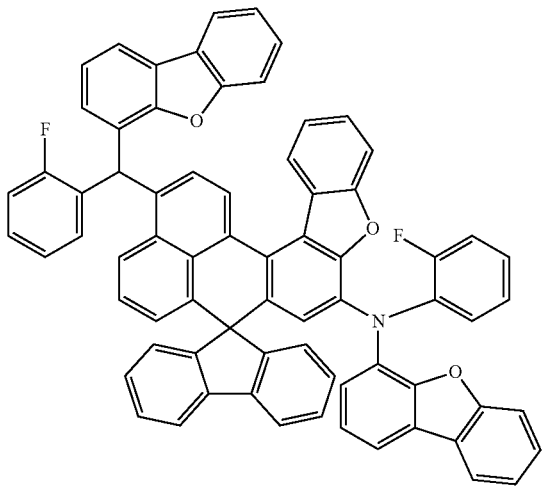
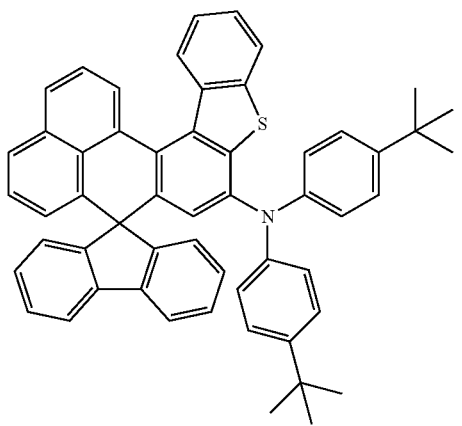
112
-continued
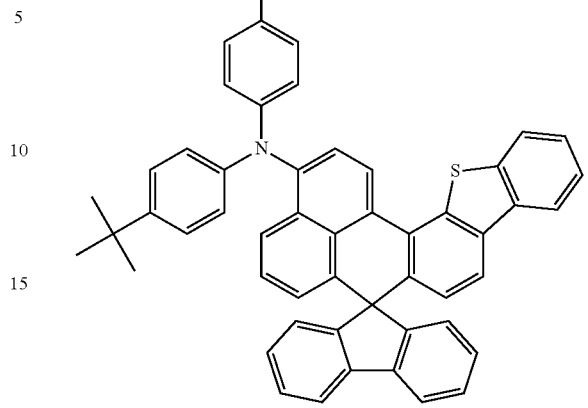
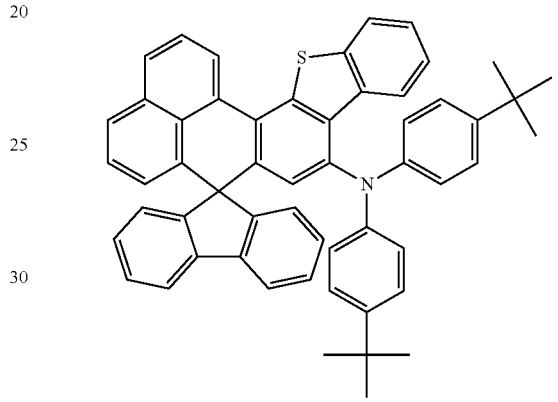
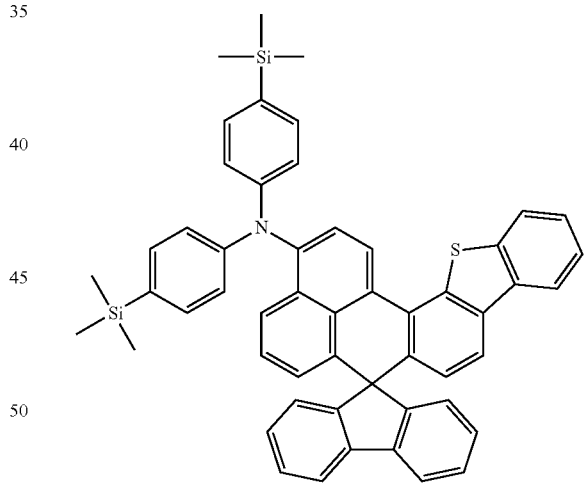
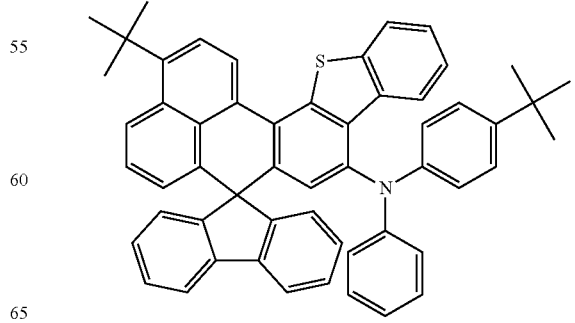

113
-continued
114
-continued
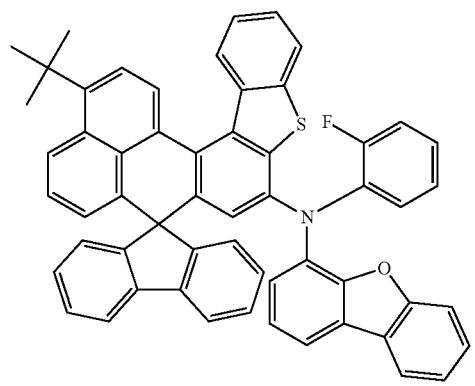
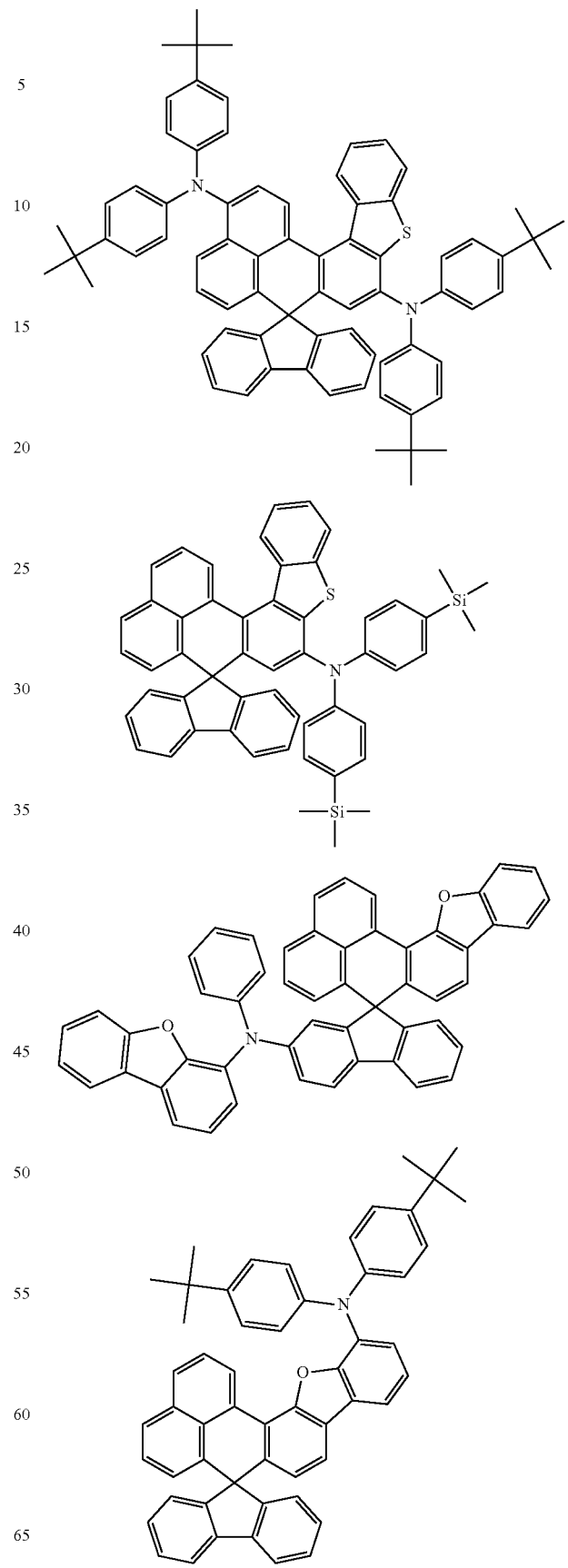

115
-continued
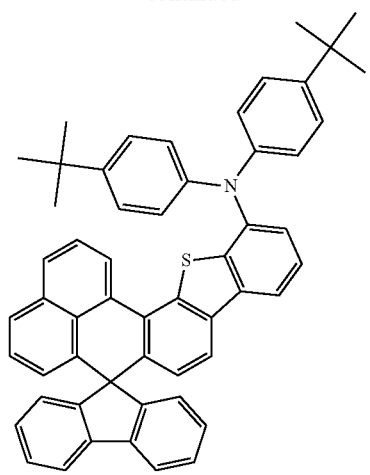
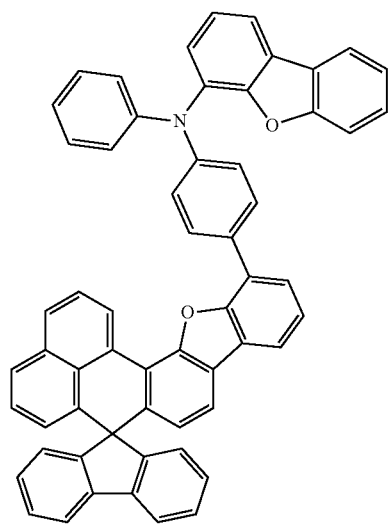
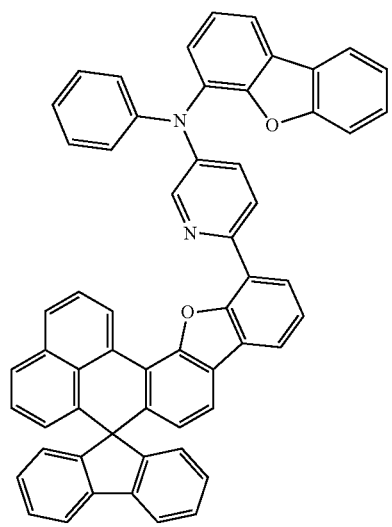
116
-continued
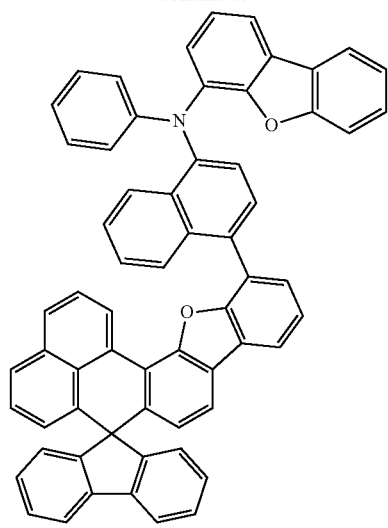
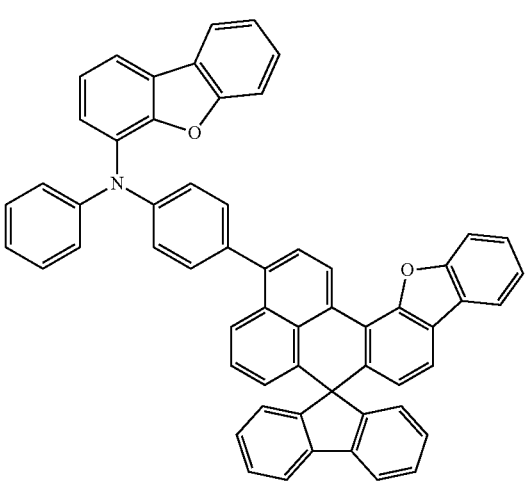
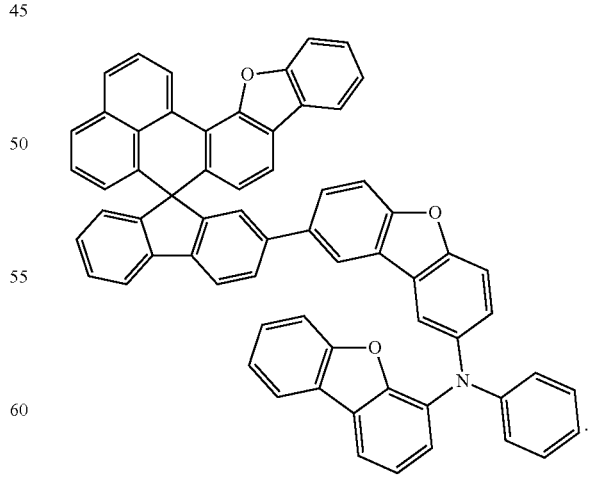
3. The organic compound of claim 1, wherein the organic compound is represented by a following chemical formula below:

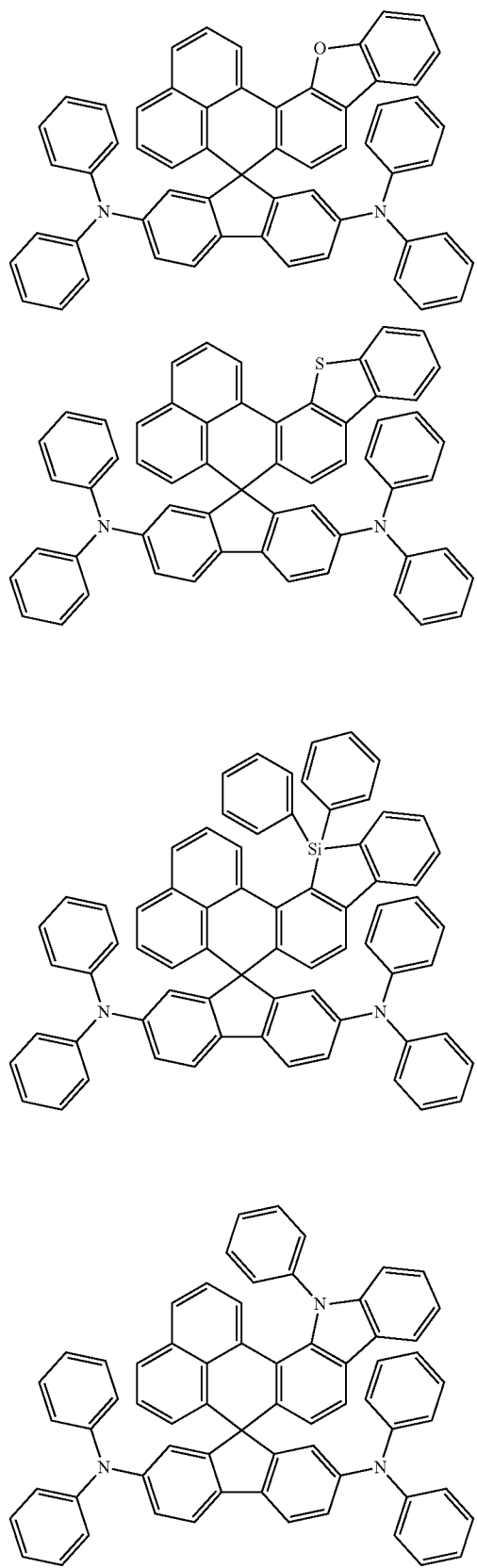
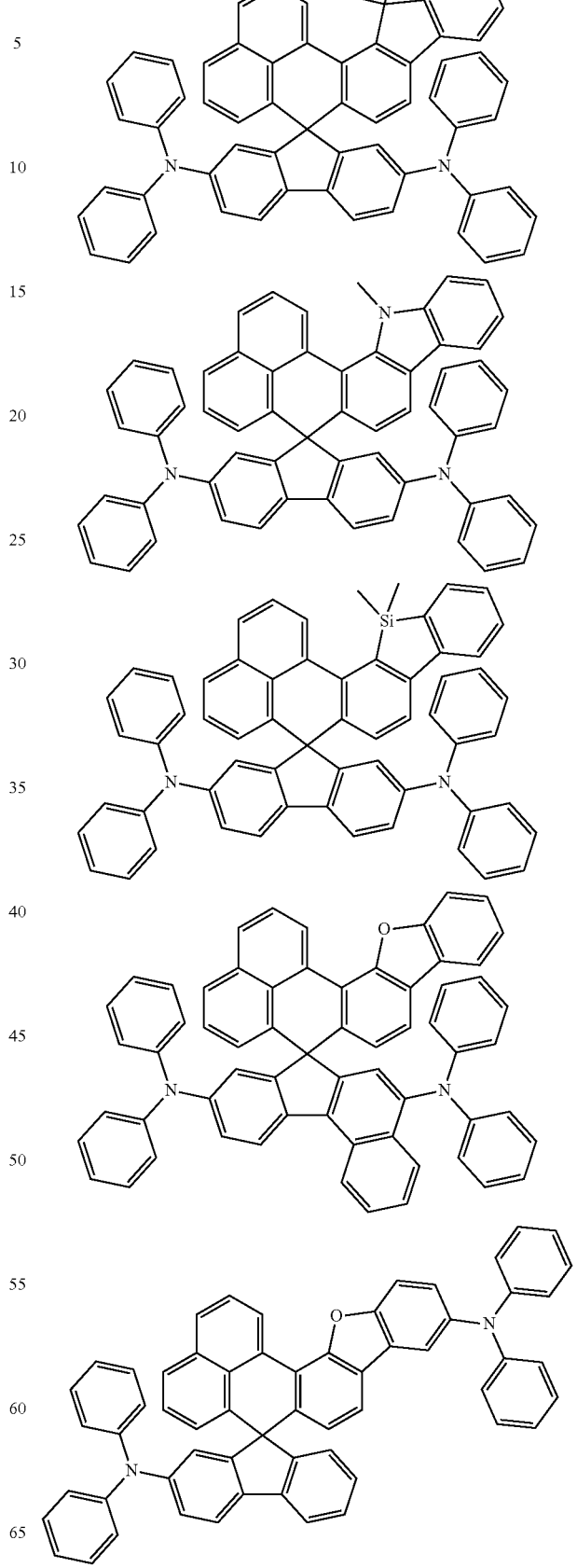

119
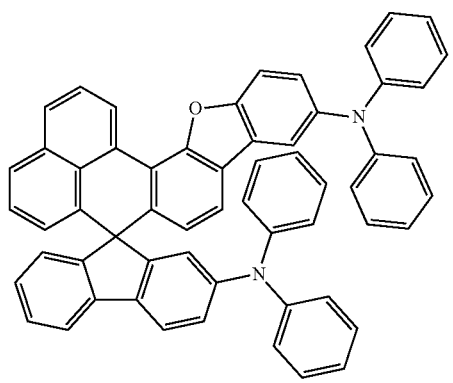
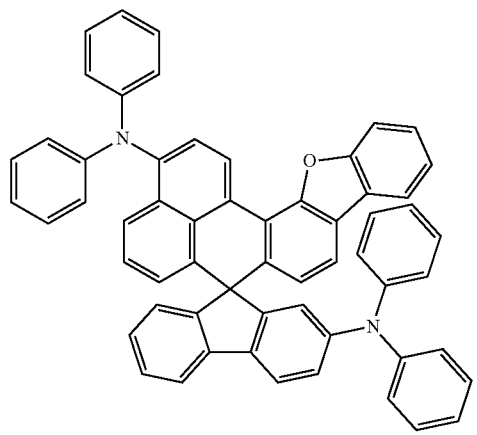
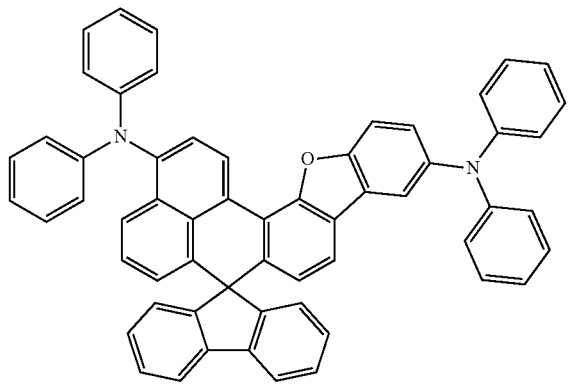
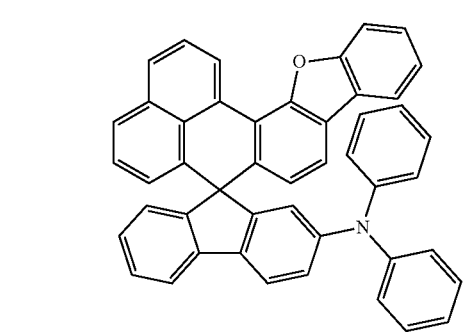
120
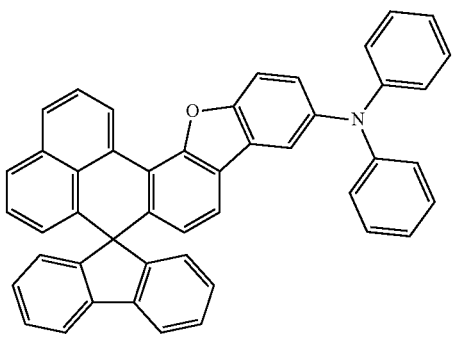
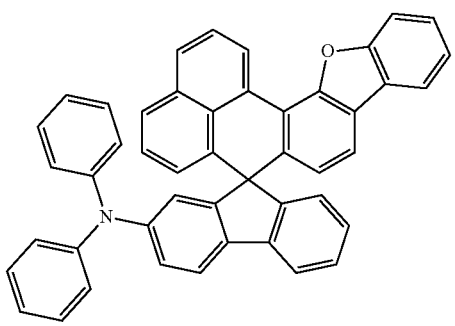
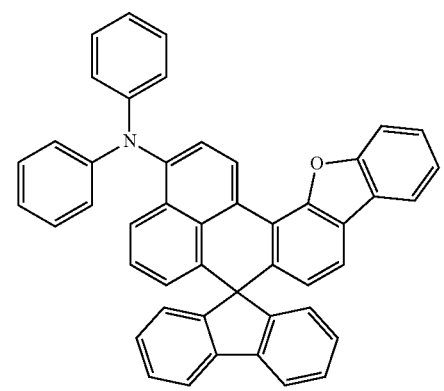
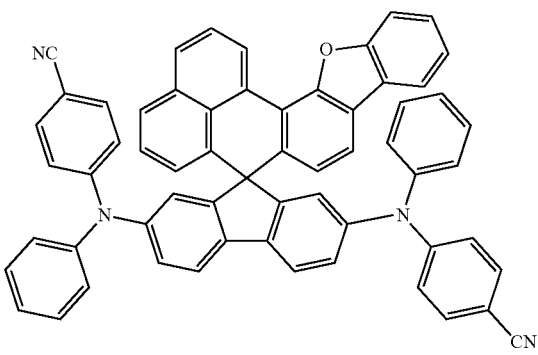

121
-continued
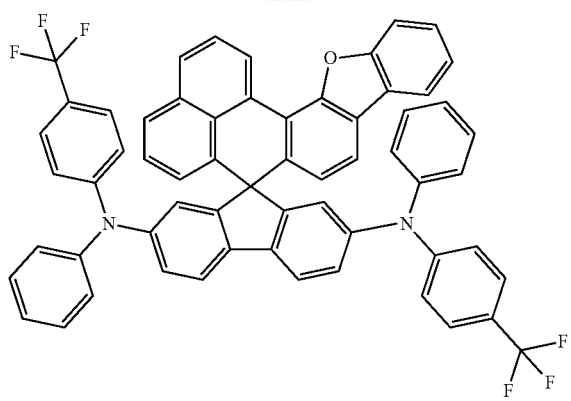
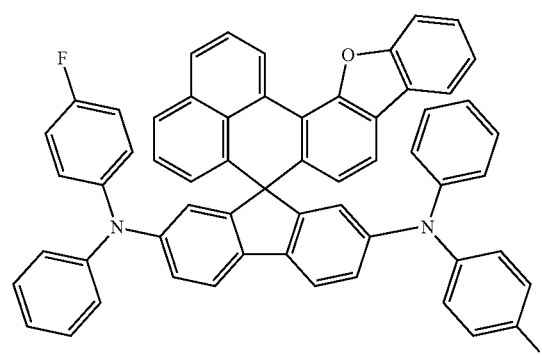
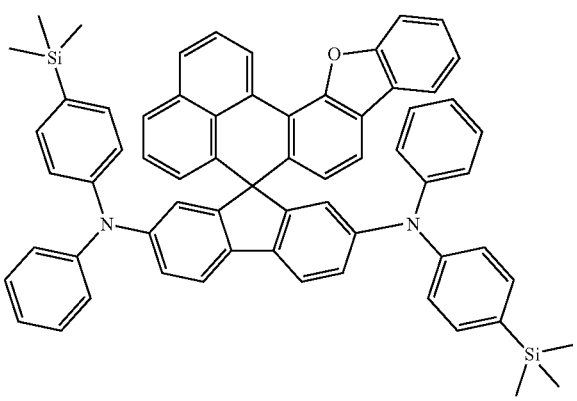
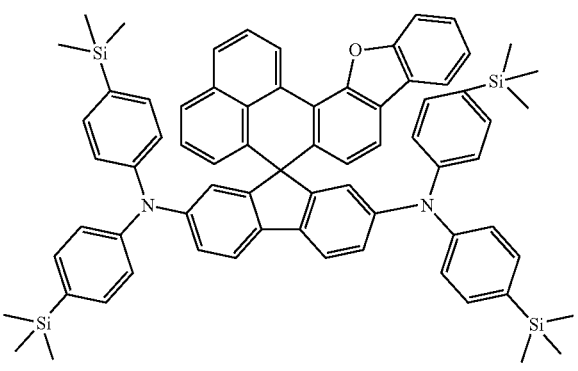
122
-continued
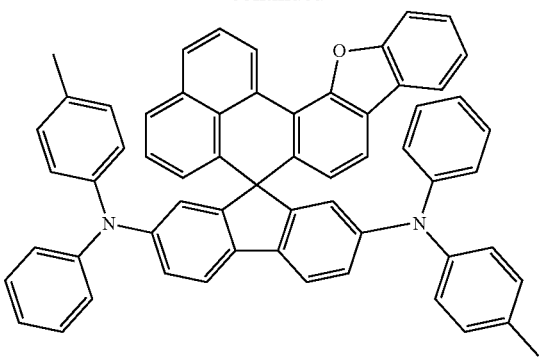
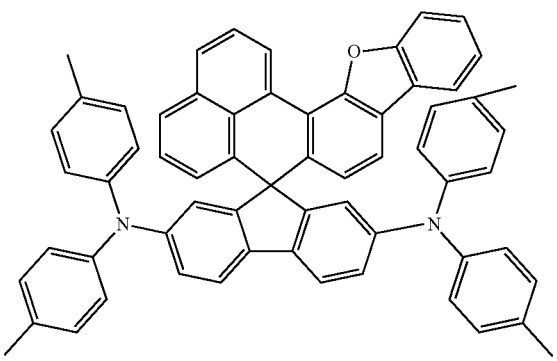
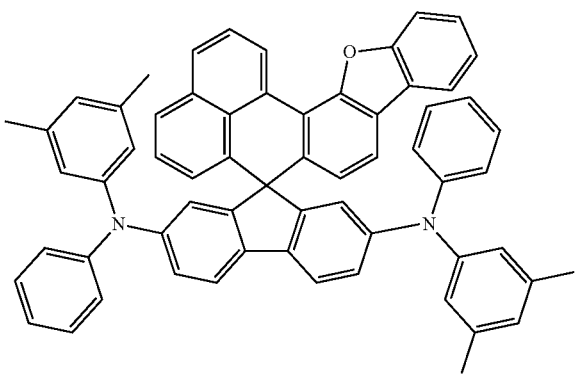
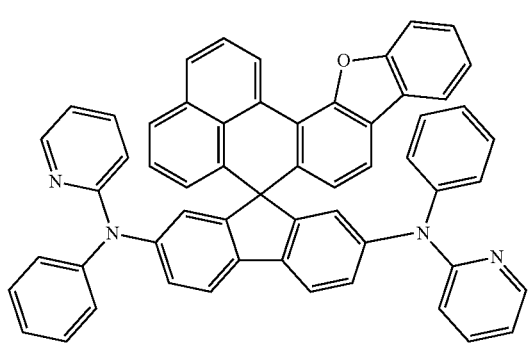

123
-continued
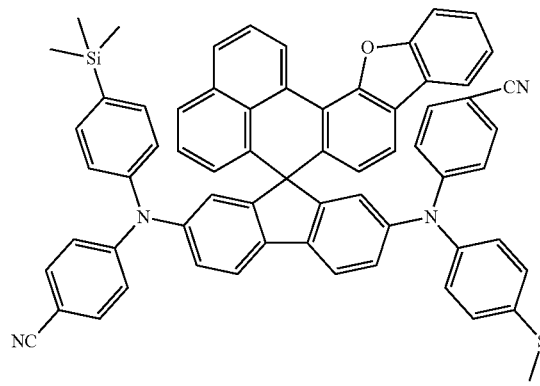
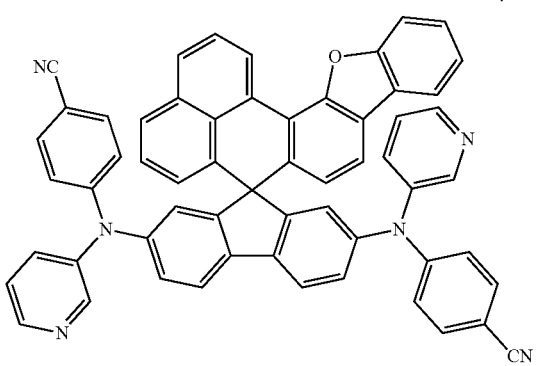
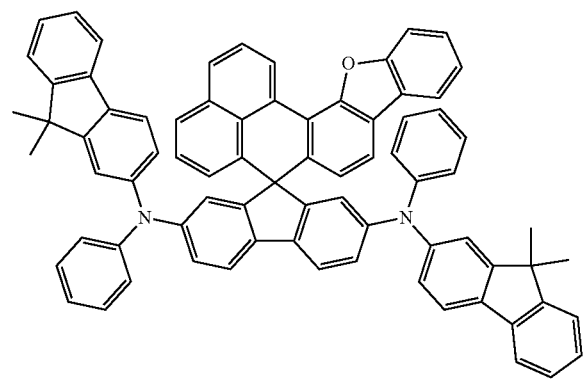
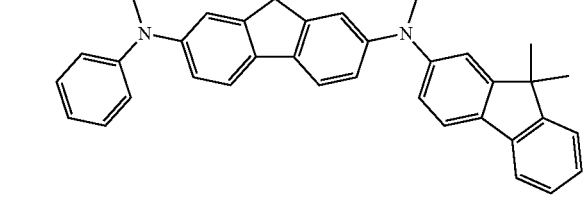
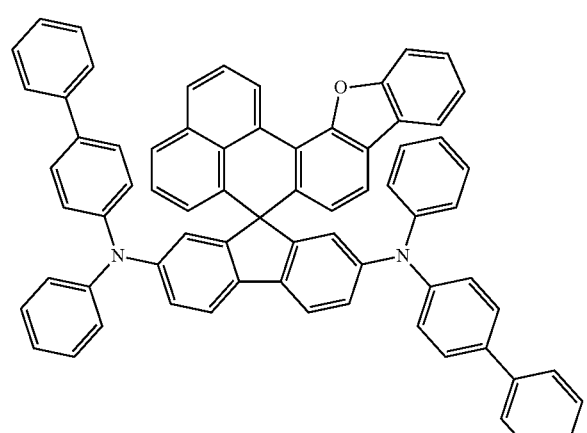
124
-continued
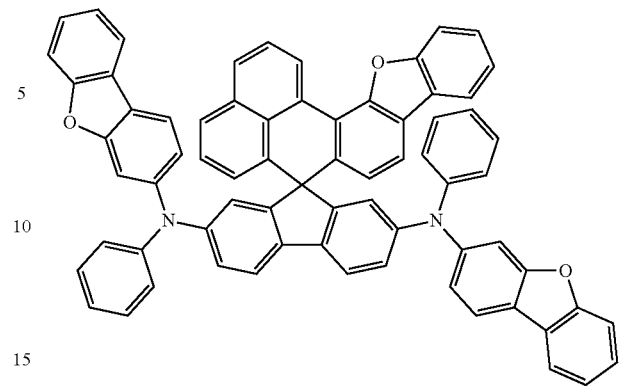
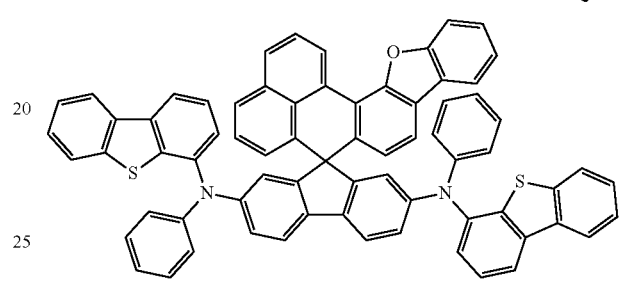
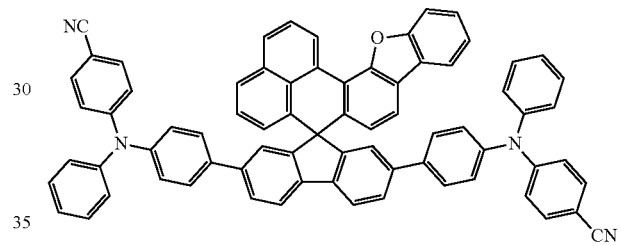
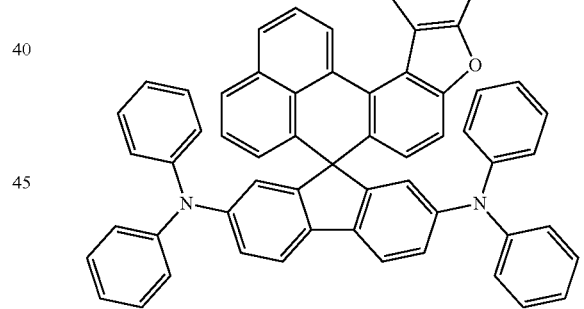
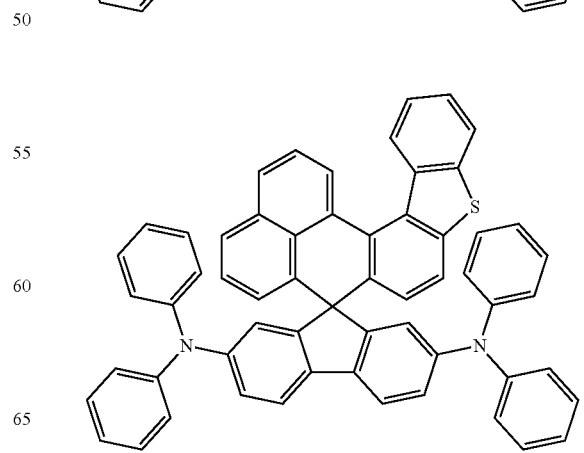

125
-continued
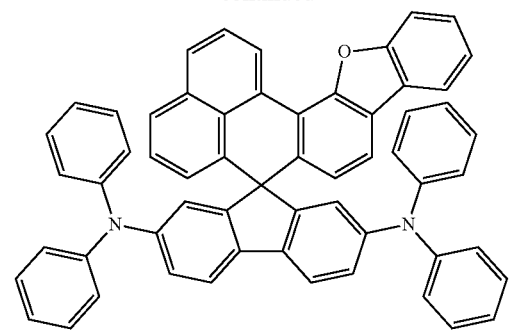
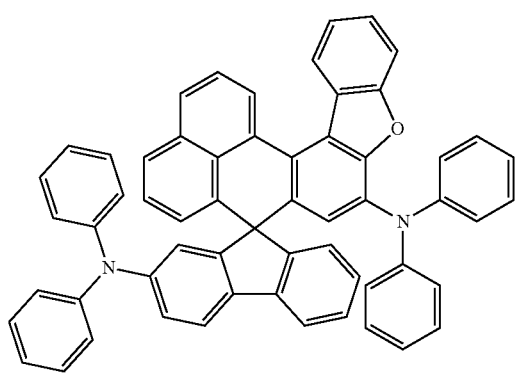
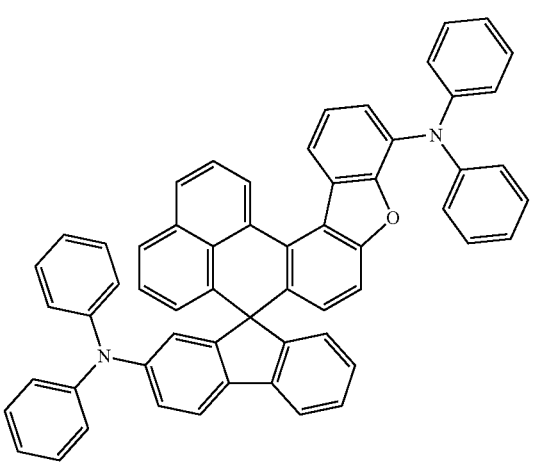
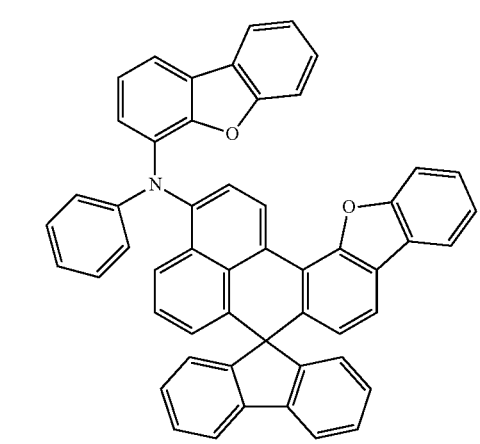
126
-continued
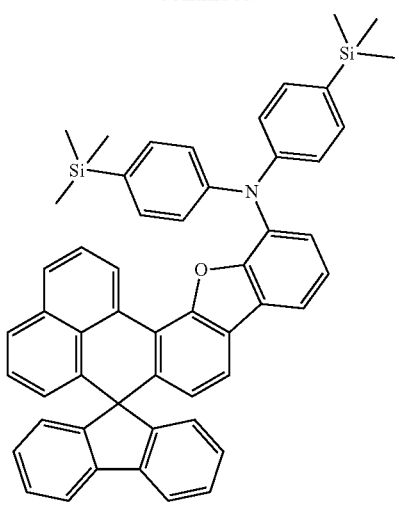
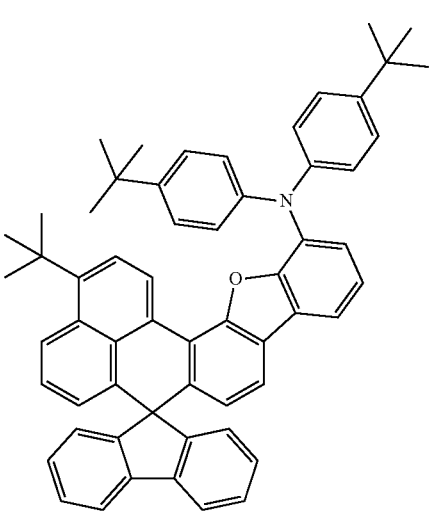
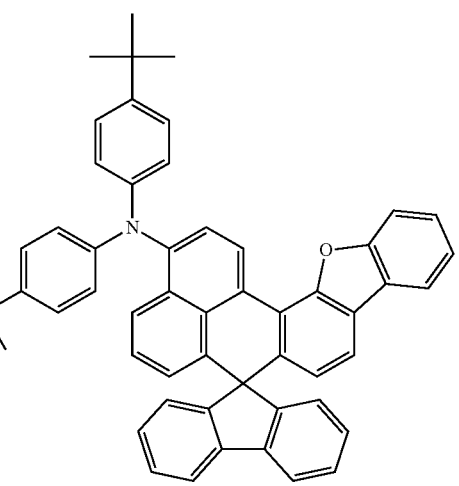

127
-continued
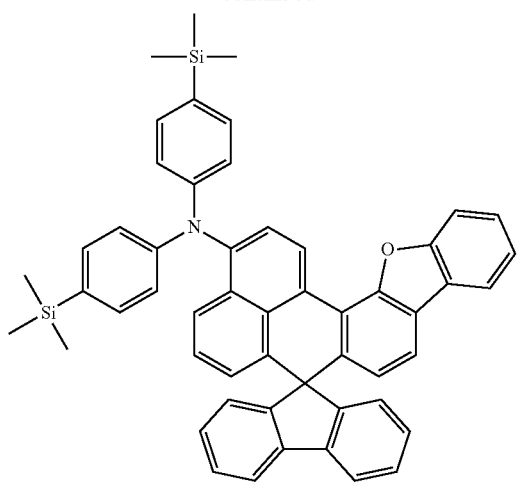
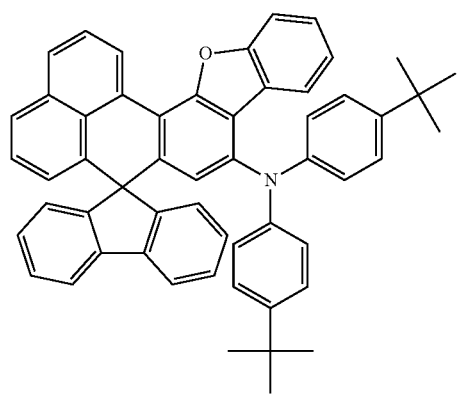
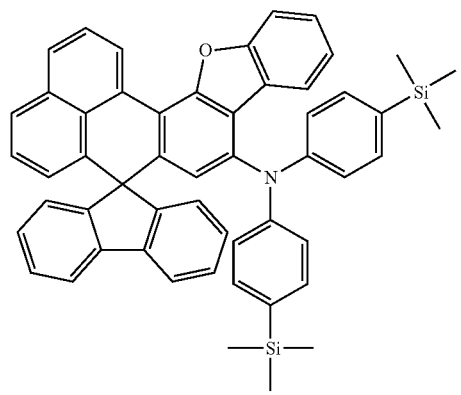
128
-continued
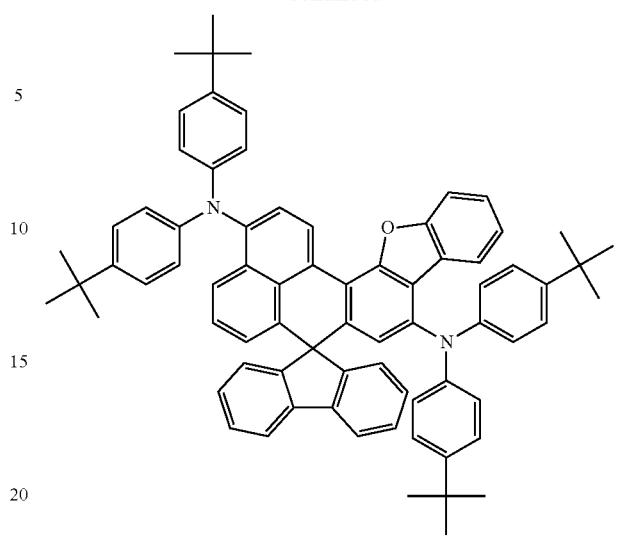
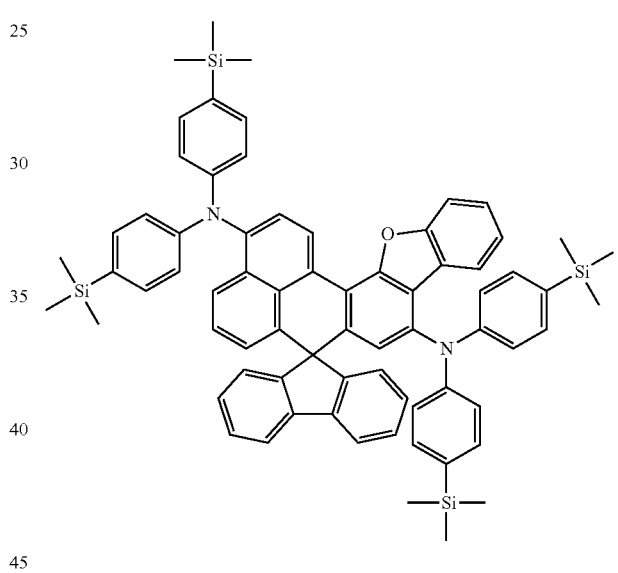
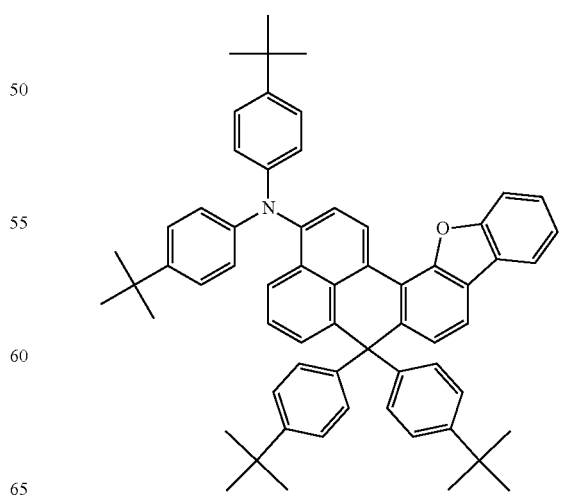

129
-continued
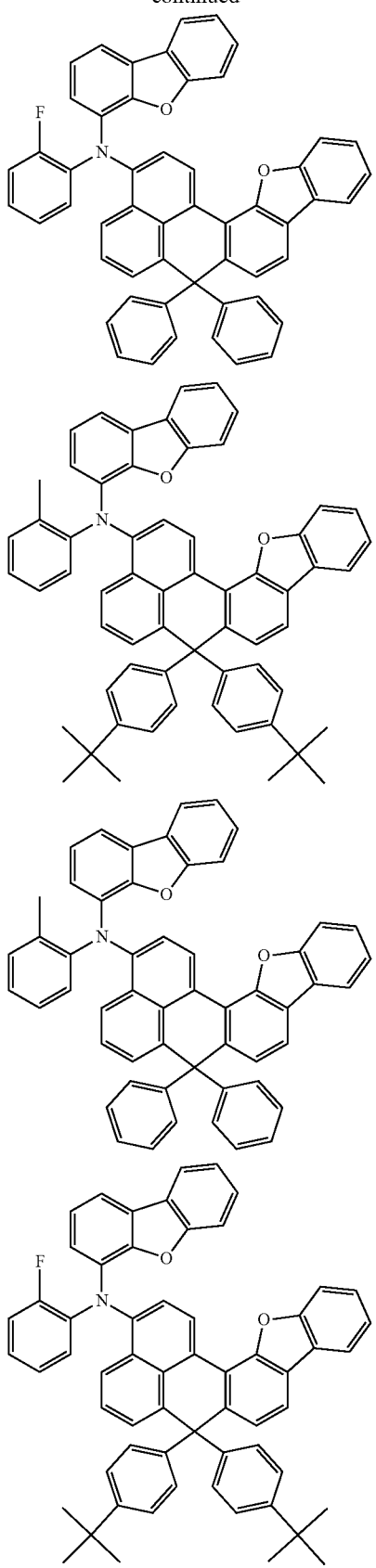
130
-continued
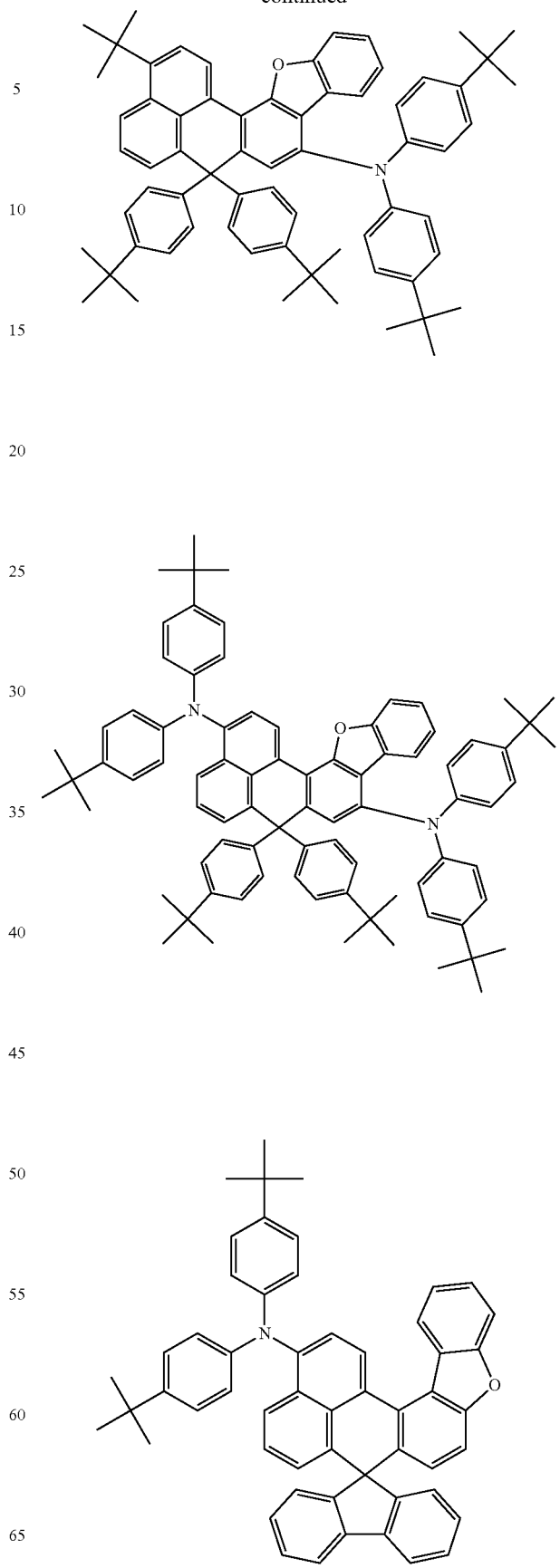

131
-continued
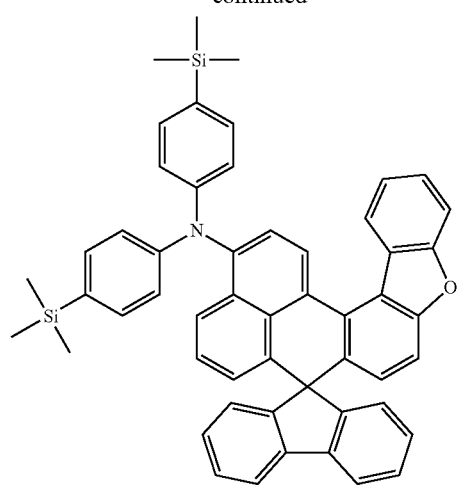
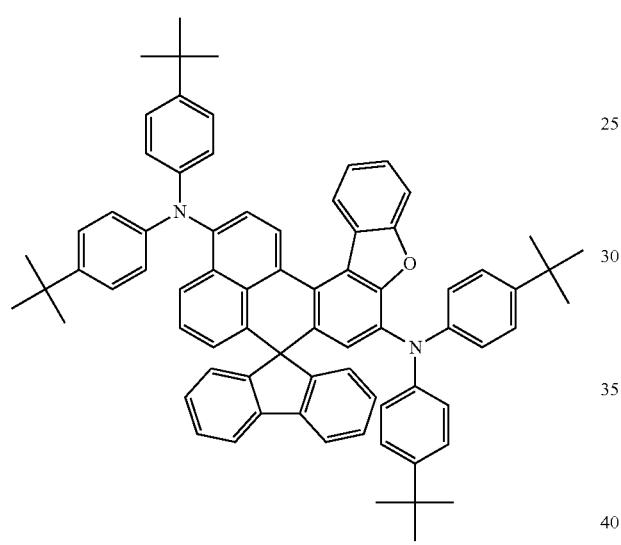
132
-continued
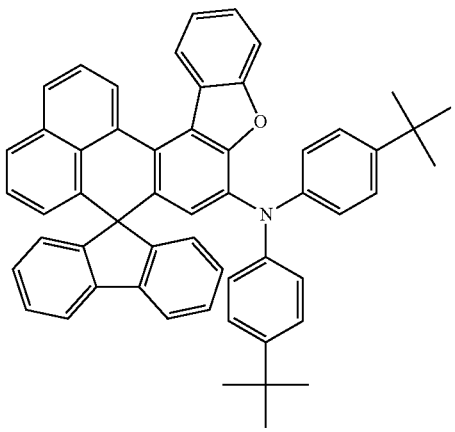
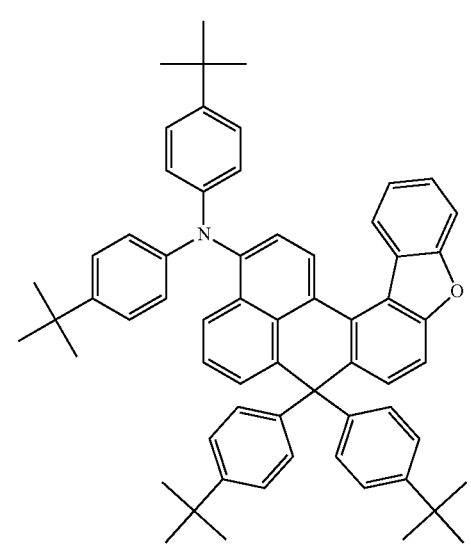
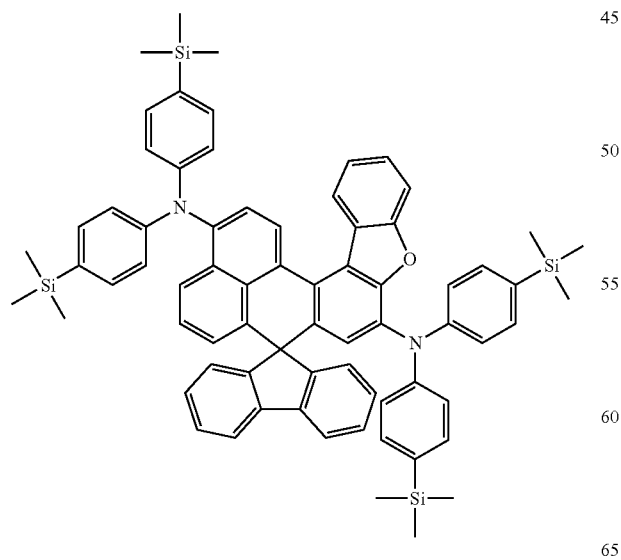

133
-continued
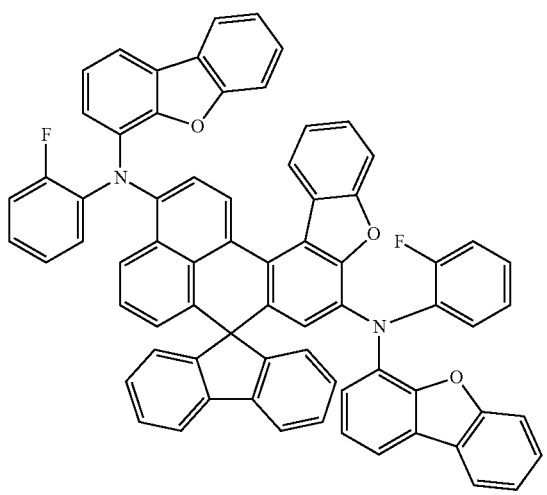
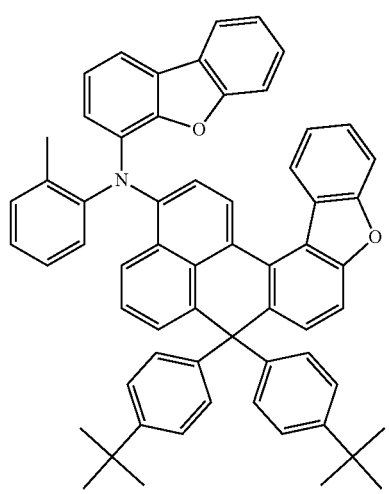
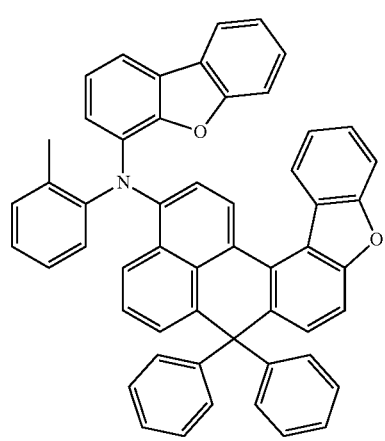
134
-continued
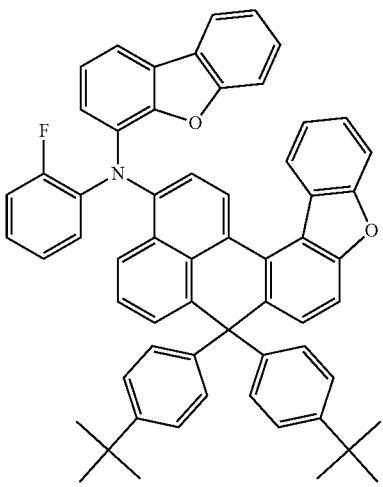
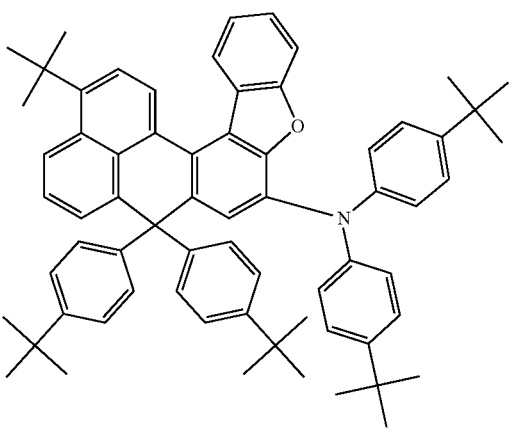
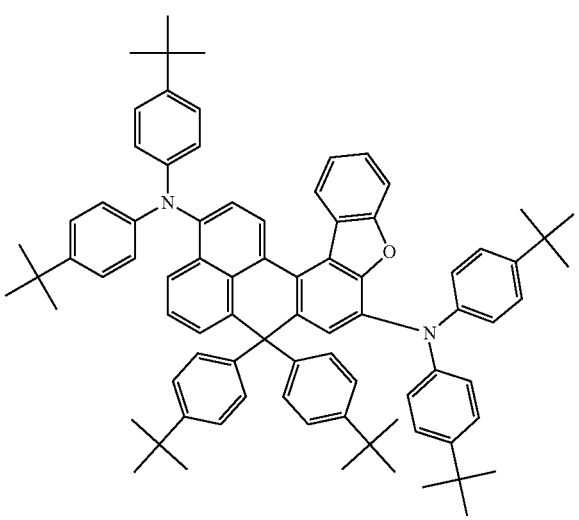

135
-continued
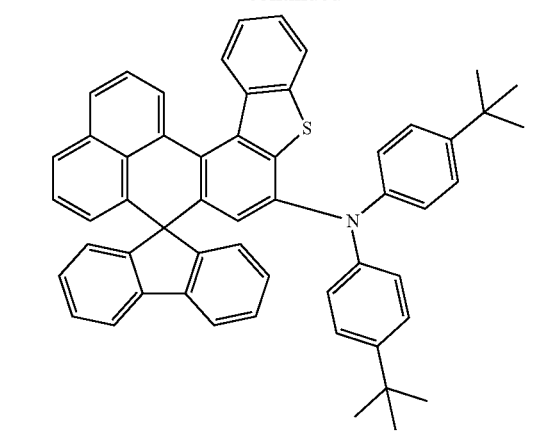
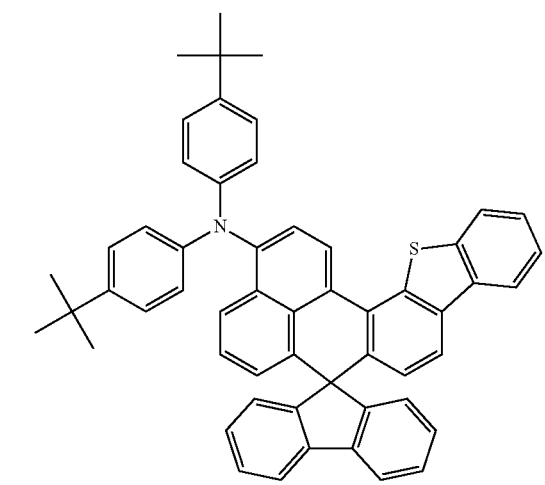
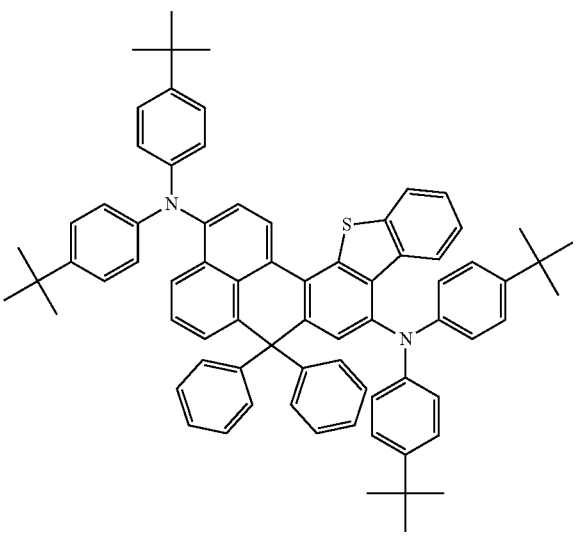
136
-continued
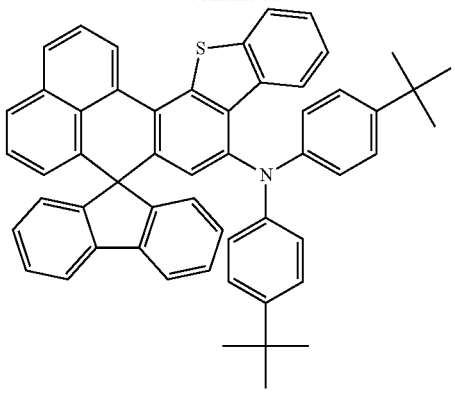
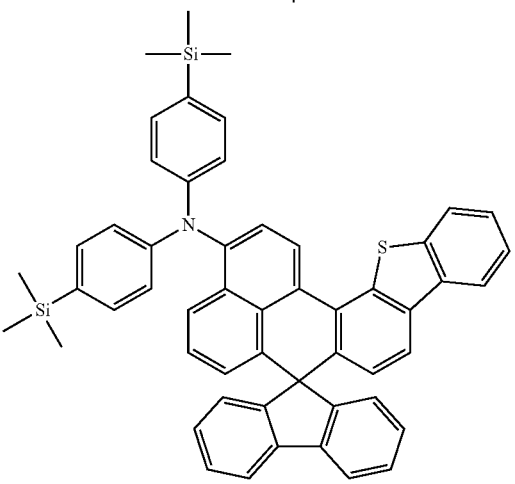
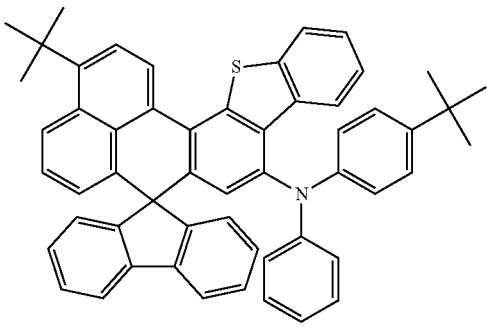
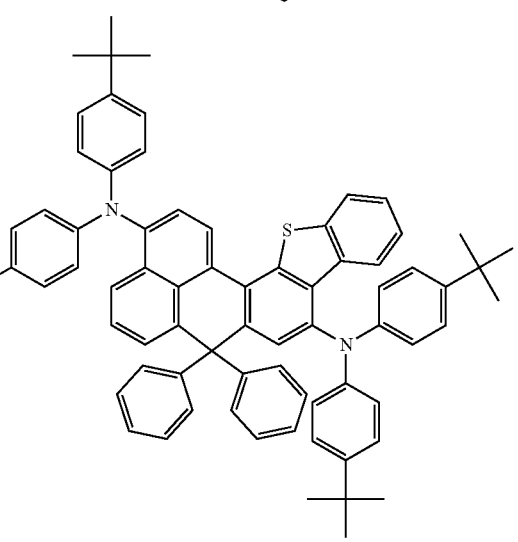

137
-continued
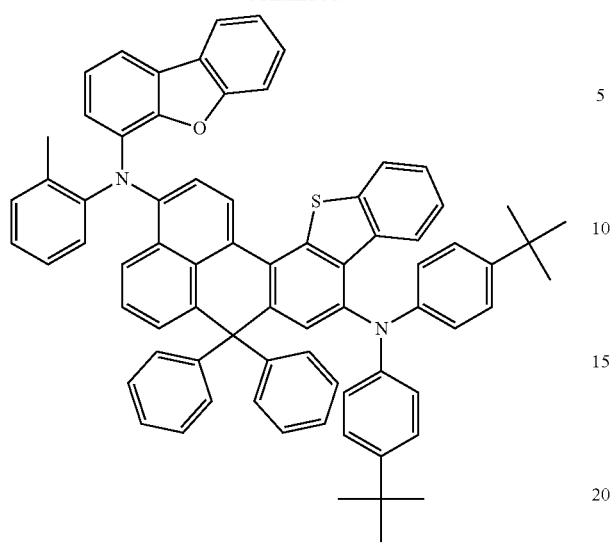
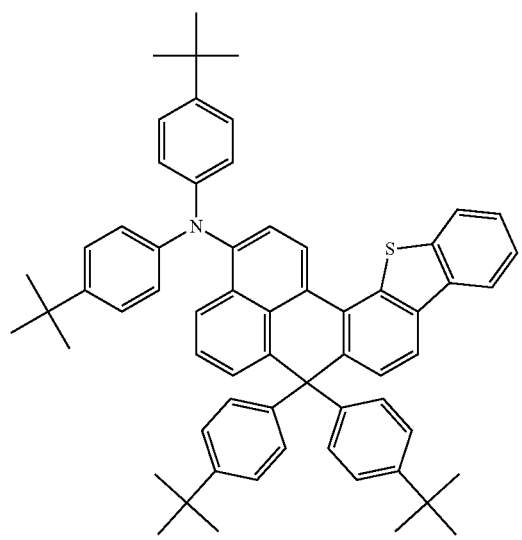
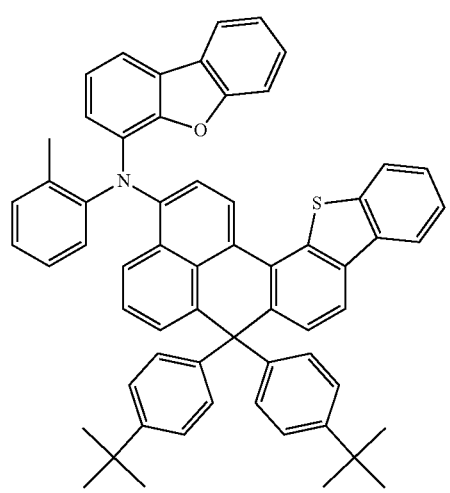
138
-continued
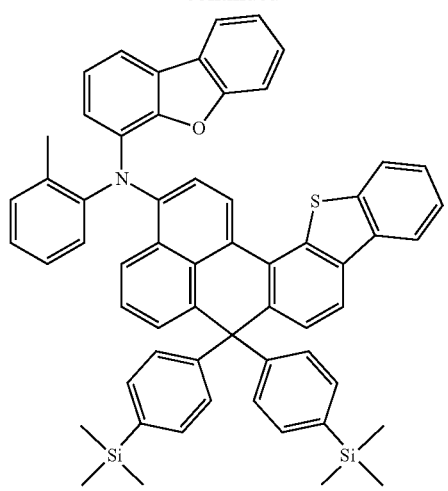
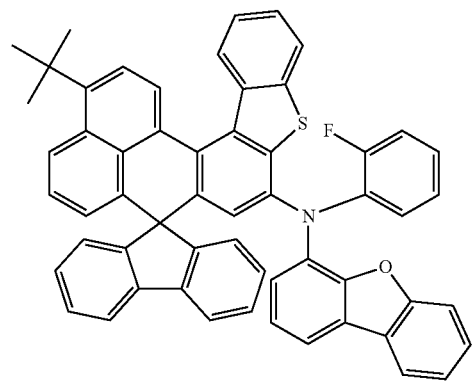
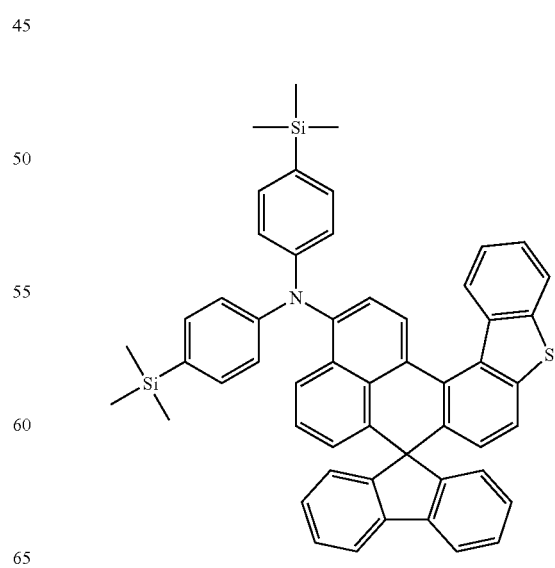

139
-continued
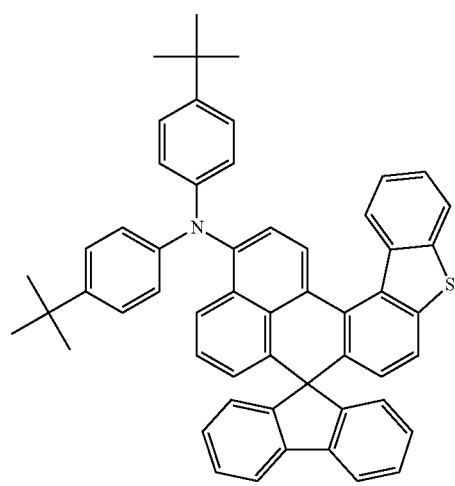
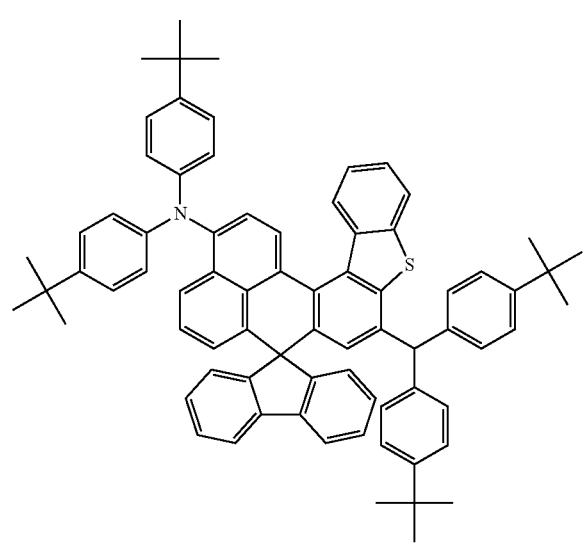
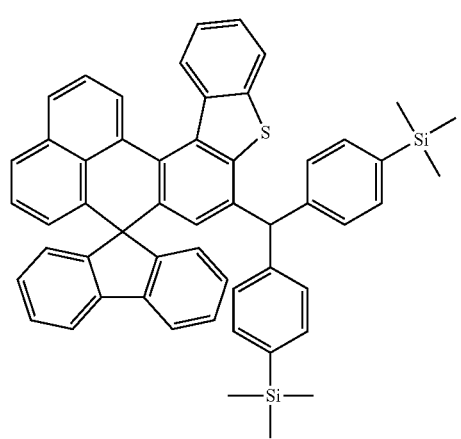
140
-continued
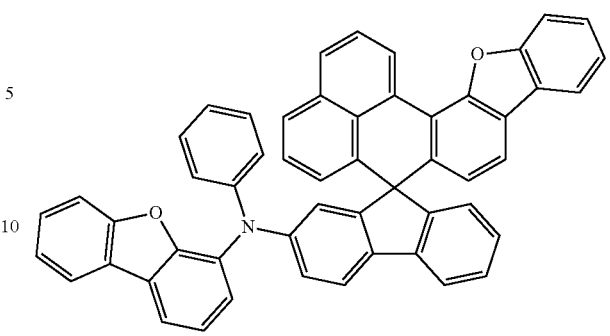
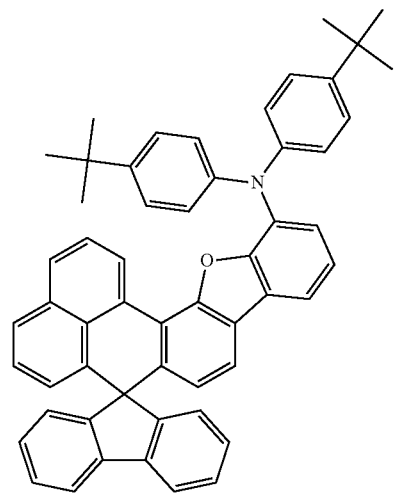
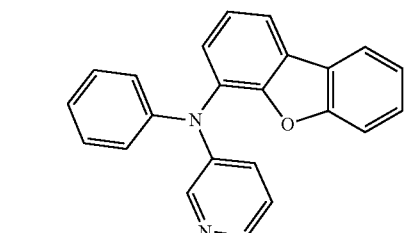
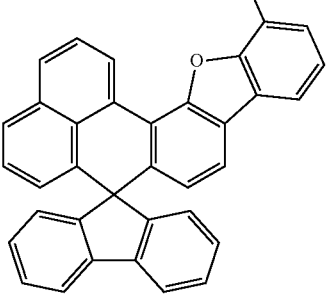

-continued

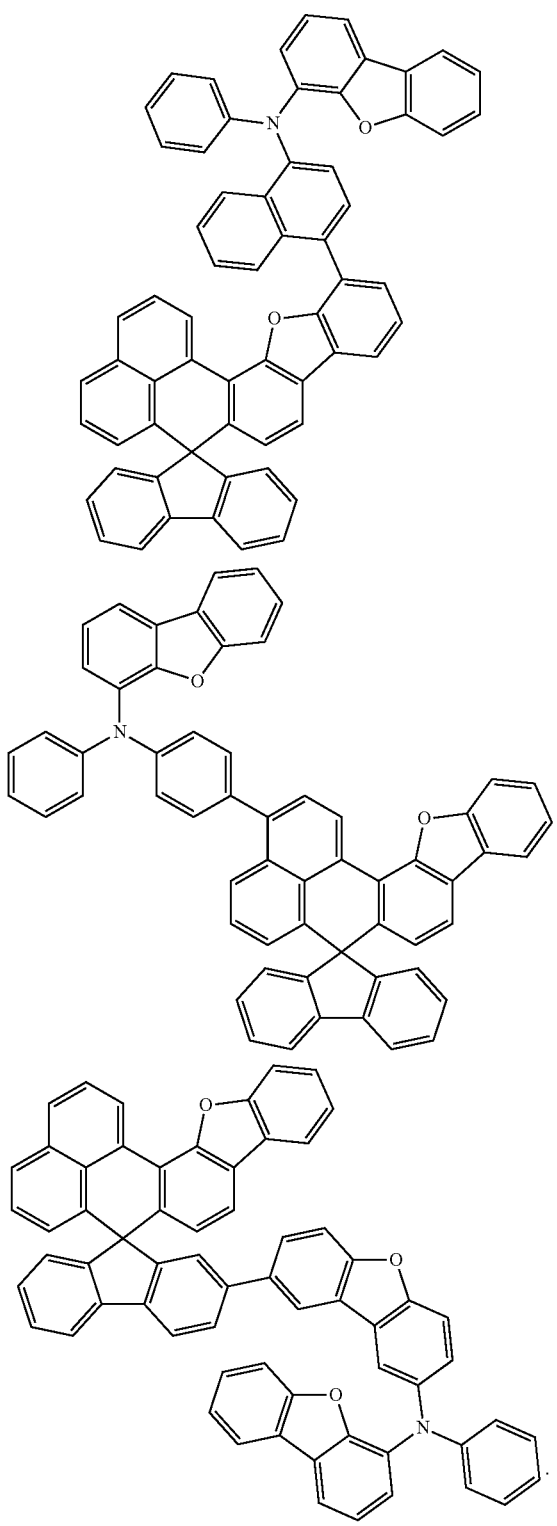

4. A light emitting diode, comprising:
a first electrode;
a second electrode facing the first electrode; and
at least one organic material layer between the first and second electrodes,
wherein the at least one organic material layer includes the organic compound of claim 1.

5. The light emitting diode of claim 4, wherein the at least one organic material layer includes at least one of an emitting material layer, a hole transporting layer and a hole injecting layer.

6. The light emitting diode of claim 4, wherein the organic compound is used as one of a host and a dopant of an emitting material layer between the first and second electrodes.

7. The light emitting diode of claim 4, wherein the organic compound is used for a hole layer between the first and second electrodes.

8. The light emitting diode of claim 7, wherein the hole layer comprises:
a hole transporting layer; and
a hole injecting layer between the hole transporting layer and the first electrode, the hole injecting layer including one of the organic compound and a hole injecting host material doped with the organic compound.

9. The light emitting diode of claim 7, wherein the hole layer comprises:
a hole transporting layer including a hole transporting host material doped with the organic compound; and
a hole injecting layer between the hole transporting layer and the first electrode.

10. The light emitting diode of claim 7, wherein the hole layer comprises:
a hole transporting layer;
a first hole injecting layer between the hole transporting layer and the first electrode, the first hole injecting layer including one of the organic compound and a hole injecting host material doped with the organic compound; and
a second hole injecting layer between the first electrode and the first injecting layer, the second hole injecting layer including a hole injecting host material.

11. The light emitting diode of claim 7, wherein the hole layer further comprises a first hole transporting layer including a hole transporting host material doped with the organic compound.

12. The light emitting diode of claim 11, wherein the hole layer further comprises a second hole transporting layer between the first hole transporting layer and the second electrode, the second hole transporting layer including a hole transporting host material.

13. An organic light emitting diode display device, comprising:
a first substrate;
a driving thin film transistor on the first substrate;
a light emitting diode connected to the driving thin film transistor, wherein the light emitting diode comprises:
a first electrode;
a second electrode facing into the first electrode; and
at least one organic material layer between the first and second electrodes,
wherein the at least one organic material layer includes the organic compound of claim 1.

* * * * *